US010000456B2

(12) United States Patent
Clark et al.

(10) Patent No.: US 10,000,456 B2
(45) Date of Patent: *Jun. 19, 2018

(54) POLYCYCLIC COMPOUNDS AS LYSOPHOSPHATIDIC ACID RECEPTOR ANTAGONISTS

(71) Applicant: AMIRA PHARMACEUTICALS, INC., Princeton, NJ (US)

(72) Inventors: Ryan Clark, San Diego, CA (US); Brian Andrew Stearns, Encinitas, CA (US); Lucy Zhao, San Diego, CA (US); Thomas Jon Seiders, San Diego, CA (US); Deborah Volkots, New York, NY (US); Jeannie M. Arruda, San Diego, CA (US)

(73) Assignee: AMIRA PHARMACEUTICALS, INC., Princeton, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/283,322

(22) Filed: May 21, 2014

(65) Prior Publication Data

US 2014/0256744 A1 Sep. 11, 2014

Related U.S. Application Data

(62) Division of application No. 12/893,902, filed on Sep. 29, 2010, now Pat. No. 8,778,983.

(60) Provisional application No. 61/247,877, filed on Oct. 1, 2009.

(51) Int. Cl.
| | |
|---|---|
| *C07D 413/04* | (2006.01) |
| *C07D 413/06* | (2006.01) |
| *C07D 413/12* | (2006.01) |
| *C07D 231/38* | (2006.01) |
| *C07D 261/08* | (2006.01) |
| *C07D 261/14* | (2006.01) |
| *C07D 417/12* | (2006.01) |
| *C07D 413/14* | (2006.01) |

(52) U.S. Cl.
CPC ......... *C07D 231/38* (2013.01); *C07D 261/08* (2013.01); *C07D 261/14* (2013.01); *C07D 413/04* (2013.01); *C07D 413/06* (2013.01); *C07D 413/12* (2013.01); *C07D 413/14* (2013.01); *C07D 417/12* (2013.01)

(58) Field of Classification Search
CPC ... C07D 413/04; C07D 413/06; C07D 413/12
USPC .......................................... 548/247; 514/378
See application file for complete search history.

(56) References Cited

U.S. PATENT DOCUMENTS

| | | | |
|---|---|---|---|
| 6,762,200 B2 | 7/2004 | Takagi | |
| 6,964,975 B2 | 11/2005 | Ueno et al. | |
| 7,094,797 B2 | 8/2006 | Horie et al. | |
| 7,115,642 B2 | 10/2006 | Singh et al. | |
| 7,135,469 B2 | 11/2006 | Pinto | |
| 7,153,880 B2 | 12/2006 | Singh et al. | |
| 7,229,987 B2 | 6/2007 | Ammenn et al. | |
| 7,285,680 B2 | 10/2007 | Habashita et al. | |
| 7,288,558 B2 | 10/2007 | Nakade et al. | |
| 7,300,917 B2 | 11/2007 | Nakade et al. | |
| 7,402,605 B2 | 7/2008 | Tani et al. | |
| 7,517,996 B2 | 4/2009 | Yamamoto et al. | |
| 7,820,682 B2 | 10/2010 | Terakado et al. | |
| 8,048,902 B2 | 11/2011 | Hutchinson et al. | |
| 8,058,300 B2 | 11/2011 | Hutchinson et al. | |
| 8,124,645 B2 | 2/2012 | Terakado et al. | |
| 8,778,983 B2 * | 7/2014 | Clark ................... | C07D 261/08 514/378 |
| 2004/0014662 A1 | 1/2004 | Lindquist et al. | |
| 2004/0167132 A1 | 8/2004 | Shankar et al. | |
| 2004/0171037 A1 | 9/2004 | Li et al. | |
| 2004/0171582 A1 | 9/2004 | Nakade et al. | |
| 2004/0192739 A1 | 9/2004 | Solow-Cordero et al. | |
| 2005/0065194 A1 | 3/2005 | Shankar et al. | |
| 2005/0101518 A1 | 5/2005 | Solow-Cordero et al. | |
| 2005/0113283 A1 | 5/2005 | Solow-Cordero et al. | |
| 2005/0261298 A1 | 11/2005 | Solow-Cordero et al. | |
| 2008/0051372 A1 | 2/2008 | Chun | |
| 2008/0064731 A1 | 3/2008 | Nakade et al. | |
| 2008/0234230 A1 | 9/2008 | Nakade et al. | |
| 2011/0082164 A1 | 4/2011 | Clark et al. | |
| 2011/0082182 A1 | 4/2011 | Buckman et al. | |

FOREIGN PATENT DOCUMENTS

| | | |
|---|---|---|
| EP | 0 702 012 | 3/1996 |
| EP | 1 258 484 | 11/2002 |
| EP | 1 340 749 | 9/2003 |
| EP | 1 550 461 | 7/2005 |
| GB | 2466121 | 6/2010 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*
Anliker, B. et al., "Cell surface receptors in lysophospholipid signaling", Seminars in Cell & Developmental Biology, vol. 15, pp. 457-465 (2004).
Castelino, F.V. et al., "Genetic deletion or pharmacologic antagonism of LPA$_1$ ameliorates dermal fibrosis in a mouse model of systemic sclerosis", Abstracts, p. S-57, 11th International Workshop on Scleroderma Research, Boston, Massachusetts, USA, Aug. 1-4, 2010.
Castelino, F.V. et al., "Genetic deletion or pharmacologic antagonism of LPA$_1$ ameliorates dermal fibrosis in a scleroderma mouse model", Arthritis & Rheumatism, accepted Jan. 18, 2011, doi:10.1002/art.30262.
Choi, J.W. et al., "Biological roles of lysophospholipid receptors revealed by genetic null mice: An update", Biochimica et Biophysica Acta, vol. 1781, pp. 531-539 (2008).
Chun, J. et al., "Lysophospholipid Receptors as Potential Drug Targets in Tissue Transplantation and Autoimmune Diseases", Current Pharmaceutical Design, vol. 12, pp. 161-171 (2006).

(Continued)

*Primary Examiner* — Patricia L Morris
(74) *Attorney, Agent, or Firm* — Hoffmann & Baron, LLP

(57) ABSTRACT

Described herein are compounds that are antagonists of lysophosphatidic receptor(s). Also described are pharmaceutical compositions and medicaments that include the compounds described herein, as well as methods of using such antagonists, alone and in combination with other compounds, for treating LPA-dependent or LPA-mediated conditions or diseases.

13 Claims, 11 Drawing Sheets

(56) References Cited

FOREIGN PATENT DOCUMENTS

| | | |
|---|---|---|
| GB | 2470833 | 12/2010 |
| JP | 11-240873 | 9/1999 |
| JP | 2003-261545 | 9/2003 |
| JP | 2006-96712 | 4/2006 |
| WO | WO 00/59902 | 10/2000 |
| WO | WO 01/60819 | 8/2001 |
| WO | WO 02/00651 | 1/2002 |
| WO | WO 02/085290 | 10/2002 |
| WO | WO 03/062392 | 7/2003 |
| WO | WO 03/097047 | 11/2003 |
| WO | WO 2004/031118 | 4/2004 |
| WO | WO 2005/012269 | 2/2005 |
| WO | WO 2005/066138 | 7/2005 |
| WO | WO 2005/123671 | 12/2005 |
| WO | WO 2006/131336 | 12/2006 |
| WO | WO 2007/007588 | 1/2007 |
| WO | WO 2007/024922 | 3/2007 |
| WO | WO 2007/096647 | 8/2007 |
| WO | WO 2007/139946 | 12/2007 |
| WO | WO 2008/024979 | 2/2008 |
| WO | WO 98/28282 | 7/2008 |
| WO | WO 2008/112201 | 9/2008 |
| WO | WO 2009/011850 | 1/2009 |
| WO | WO 2009/135590 | 11/2009 |
| WO | WO 2010/068775 | 6/2010 |
| WO | WO 2010/077882 | 7/2010 |
| WO | WO 2010/077883 | 7/2010 |
| WO | WO 2010/141761 | 12/2010 |
| WO | WO 2010/141768 | 12/2010 |
| WO | WO 2011/017350 | 2/2011 |
| WO | WO 2011/041461 | 4/2011 |
| WO | WO 2011/041462 | 4/2011 |
| WO | WO 2011/041694 | 4/2011 |
| WO | WO 2011/041729 | 4/2011 |

OTHER PUBLICATIONS

Chun, J., "Lysophospholipids in the nervous system", Prostaglandins & Other Lipid Mediators, vol. 77, pp. 46-51 (2005).
Evans, J.F. et al., "Seeing the future of bioactive lipid drug targets", Nature Chemical Biology, vol. 6, pp. 476-479 (2010).
Fukushima, N. et al., "The LPA Receptors", Prostaglandins & Other Lipid Mediators, vol. 64, pp. 21-32 (2001).
Gardell, S.E. et al., "Emerging medicinal roles for lysophospholipid signaling", Trends in Molecular Medicine, vol. 12, No. 2, pp. 65-75 (2006).
Golub, T.R. et al., "Molecular Classification of Cancer: Class Discovery and Class Prediction by Gene Expression Monitoring", Science, vol. 286, pp. 531-537 (1999).
Ishii, I. et al., "Lysophospholipid Receptors: Signaling and Biology", Annu. Rev. Biochem., vol. 73, pp. 321-354 (2004).
Kainuma, M. et al., "Design, synthesis, and evaluation of nonsteroidal farnesolid X receptor (FXR) antagonist", Bioorganic & Medicinal Chemistry, vol. 15, No. 7, pp. 2587-2600 (2007).
Lala, P.K. et al., "Role of nitric oxide in tumor progression: Lessons from experimental tumors", Cancer and Metastasis Reviews, vol. 17, pp. 91-106 (1998).
Ley, K. et al., "From lung injury to fibrosis", Nature Medicine, vol. 14, No. 1, pp. 20-21 (2008).
Mills, G.B. et al., "The Emerging Role of Lysophosphatidic Acid in Cancer", Nature Reviews: Cancer, vol. 3, pp. 582-591 (2003).
Murph, M.M. et al., "Sharpening the edges of understanding the structure/function of the LPA1 receptor: Expression in cancer and mechanisms of recognition", Biochimica et Biophysica Acta, vol. 1781, pp. 547-557 (2008).
Ohta, H. et al., "Ki16425, a Subtype-Selective Antagonist for EDG-Family Lysophosphatidic Acid Receptors", Molecular Pharmacology, vol. 64, No. 4, pp. 994-1005 (2003).

Parrill, A.L. et al., "Sphingosine 1-phosphate and lysophosphatidic acid receptors: agonist and antagonist binding and progress toward development of receptor-specific ligands", Seminars in Cell & Developmental Biology, vol. 15, pp. 467-476 (2004).
Pradère, J.-P. et al., "LPA$_1$ Receptor Activation Promotes Renal Interstitial Fibrosis", J. Am. Soc. Nephrol., vol. 18, pp. 3110-3118 (2007).
Pradère, J.-P. et al., "Lysophosphatidic acid and renal fibrosis", Biochimica et Biophysica Acta (2008), doi:10.1016/j.bbalip.2008.04.001.
Prestwich, G.D. et al., "New metabolically stabilized analogues of lysophosphatidic acid: agonists, antagonists and enzyme inhibitors", Biochemical Society Transactions, vol. 33, Part 6, pp. 1357-1361 (2005).
Sardar, V.M. et al., "Molecular basis for lysophoshatidic acid receptor antagonist selectivity", Biochimica et Biophysica Acta, vol. 1582, pp. 309-317 (2002).
Scott, I. "Lysophosphatidic acid is an important mediator of fibroblast recruitment in IPF", Thorax, vol. 63, No. 7, p. 654 (2008).
Swaney, J.S. et al., "A novel, orally activa LPA$_1$ receptor antagonist inhibits lung fibrosis in the mouse bleomycin model", British Journal of Pharmacology, vol. 160, pp. 1699-1713 (2010).
Swaney, J.S. et al., "Pharmacokinetic and Pharmacodynamic Characterization of an Oral, LPA$_1$-selective Antagonist", Journal of Pharmacology and Experimental Therapeutics, published Dec. 15, 2010, doi:10.1124/jpet.110.175901.
Tager, A.M. et al., "The lysophosphatidic acid receptor LPA$_1$ links pulmonary fibrosis to lung injury by mediating fibroblast recruitment and vascular leak", Nature Medicine, vol. 14, No. 1, pp. 45-54 (2008).
Toews, M.L. et al., "Lysophosatidic acid in airway function and disease", Biochimica et Biophysica Acta, vol. 1582, pp. 240-250 (2002).
Watanabe, N. et al., "Both Plasma Lysophosphatidic Acid and Serum Autotaxin Levels are Increased in Chronic Hepatitis C", J. Clin. Gastroenterol., vol. 41, No. 6, pp. 616-623 (2007).
Watanabe, N. et al., "Plasma lysophosphatidic acid level and serum autotaxin activity are increased in liver injury in rats in relation to its severity", Life Sciences, vol. 81, pp. 1009-1015 (2007).
Watterson, K.R. et al., "Regulation of fibroblast functions by lysophospholipid mediators: Potential roles in wound healing", Wound Repair and Regeneration, vol. 15, pp. 607-616 (2007).
Yamamoto, T. et al., "Synthesis and evaluation of isoxazole derivatives as lysophosphatidic acid (LPA) antagonists", Bioorganic & Medicinal Chemistry Letters, vol. 17, pp. 3736-3740 (2007).
Yang, A.H. et al., "In vivo roles of lysophospholipid receptors revealed by gene targeting studies in mice", Biochimica et Biophysica Acta, vol. 1582, pp. 197-203 (2002).
Yang, M. et al., "G protein-coupled lysophosphatidic acid receptors stimulate proliferation of colon cancer cells through the β-catenin pathway", Proc. Natl. Acad. Sci., vol. 102, No. 17, pp. 6027-6032 (2005).
Yokoyama, K. et al., "Stereochemical properties of lysophosphatidic acid receptor activation and metabolism", Biochimica et Biophysica Acta, vol. 1582, pp. 295-308 (2002).
Zhao, Y. et al., "Lysophosphatidic acid signaling in airway epithelium: Role in airway inflammation and remodeling", Cellular Signaling, vol. 21, pp. 367-377 (2009).
GB 0921606.0 Search Report, dated Dec. 23, 2009.
PCT/US09/068105 Search Report and Written Opinion, dated Aug. 13, 2010.
PCT/US09/068106 Search Report and Written Opinion, dated Jun. 23, 2010.
PCT/US10/37309 Search Report and Written Opinion, dated Feb. 28, 2011.
PCT/US10/37316 Search Report and Written Opinion, dated Feb. 9, 2011.
PCT/US10/44284 Search Report and Written Opinion, dated Apr. 26, 2011.
PCT/US10/50786 Search Report and Written Opinion, dated Jun. 24, 2011.
PCT/US10/50787 Search Report and Written Opinion, dated Jun. 15, 2011.

(56) References Cited

OTHER PUBLICATIONS

PCT/US10/51150 Search Report and Written Opinion, dated Jun. 21, 2011.
PCT/US10/51199 Search Report and Written Opinion, dated Jun. 15, 2011.

* cited by examiner

Compound 1

Compound 4

Compound 7

Compound 2

Compound 5

Compound 8

Compound 3

Compound 6

Compound 9

Compound 10

Compound 13

Compound 16

Compound 11

Compound 14

Compound 17

Compound 12

Compound 15

Compound 18

Compound 19

Compound 22

Compound 25

Compound 20

Compound 23

Compound 26

Compound 21

Compound 24

Compound 27

Compound 28

Compound 31

Compound 34

Compound 29

Compound 32

Compound 35

Compound 30

Compound 33

Compound 36

Compound 37

Compound 40

Compound 43

Compound 38

Compound 41

Compound 44

Compound 39

Compound 42

Compound 45

Compound 46

Compound 49

Compound 52

Compound 47

Compound 50

Compound 53

Compound 48

Compound 51

Compound 54

Compound 55

Compound 58

Compound 61

Compound 56

Compound 59

Compound 62

Compound 57

Compound 60

Compound 63

Compound 64

Compound 67

Compound 70

Compound 65

Compound 68

Compound 71

Compound 66

Compound 69

Compound 72

Compound 82

Compound 85

Compound 88

Compound 83

Compound 86

Compound 89

Compound 84

Compound 87

Compound 90

Compound 91

Compound 94

Compound 97

Compound 92

Compound 95

Compound 98

Compound 93

Compound 96

POLYCYCLIC COMPOUNDS AS LYSOPHOSPHATIDIC ACID RECEPTOR ANTAGONISTS

RELATED APPLICATIONS

This application is a divisional of U.S. Non-Provisional application Ser. No. 12/893,902, filed Sep. 29, 2010, which claims the benefit of U.S. Provisional Application No. 61/247,877, filed Oct. 1, 2009, which are hereby incorporated by reference in their entirety.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with one or more of the lysophosphatidic acid (LPA) receptors.

BACKGROUND OF THE INVENTION

Lysophospholipids are membrane-derived bioactive lipid mediators. Lysophospholipids affect fundamental cellular functions that include proliferation, differentiation, survival, migration, adhesion, invasion, and morphogenesis. These functions influence many biological processes that include, but are not limited to, neurogenesis, angiogenesis, wound healing, fibrosis, immunity, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses. Antagonists of the LPA receptors find use in the treatment of diseases, disorders or conditions in which LPA plays a role.

SUMMARY OF THE INVENTION

In one aspect, presented herein are compounds of Formula (I) that inhibit the physiological activity of lysophosphatidic acid (LPA), and therefore, are useful as agents for the treatment or prevention of diseases in which inhibition of the physiological activity of LPA is useful, such as diseases in which an LPA receptor participates, is involved in the etiology or pathology of the disease, or is otherwise associated with at least one symptom of the disease.

In one aspect, the compounds of Formula (I) are useful for the treatment of fibrosis of organs (liver, kidney, lung, heart and the like), liver diseases (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like), inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like). In one aspect, the compounds of Formula (I) are used in the treatment of fibrotic diseases or conditions.

In one aspect, described herein are compounds of Formula (I), pharmaceutically acceptable salts, solvates, and prodrugs thereof. Compounds of Formula (I) are antagonists of at least one of the LPA receptors selected from $LPA_1$, $LPA_2$, $LPA_3$, $LPA_4$, $LPA_5$ and $LPA_6$. In one embodiment, compounds of Formula (I) are antagonists of $LPA_1$. In one embodiment, compounds of Formula (I) are antagonists of $LPA_1$ and/or $LPA_3$. In some embodiments, compounds of Formula (I) are antagonists of $LPA_1$ and/or $LPA_2$. In some embodiments, compounds of Formula (I) are selective antagonists for one of the LPA receptors relative to the other LPA receptors. In some embodiments, such a selective antagonist is selective for the $LPA_1$ receptor. In some embodiments, such a selective antagonist is selective for the $LPA_2$ receptor. In some embodiments, such a selective antagonist is selective for the $LPA_3$ receptor.

Compounds of Formula (I) are used in the treatment of diseases, disorders, or conditions in which activation of at least one LPA receptor by LPA contributes to the symptomology or progression of the disease, disorder or condition. In one aspect, the methods, compounds, pharmaceutical compositions, and medicaments described herein comprise antagonists of LPA receptor(s). In one aspect, the methods, compounds, pharmaceutical compositions, and medicaments described herein comprise antagonists of $LPA_1$, $LPA_2$, or $LPA_3$, or combinations thereof.

In one aspect, provided herein is a compound of Formula (I), or a pharmaceutically acceptable salt thereof:

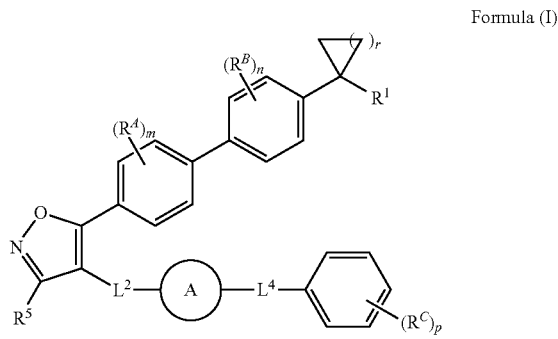

Formula (I)

wherein,
$R^1$ is $-CO_2R^D$, $-C(=O)NHSO_2R^E$, $-C(=O)N(R^D)_2$, $-CN$, or tetrazolyl;
$R^D$ is H or $C_1$-$C_6$ alkyl;
$R^E$ is $C_1$-$C_6$ alkyl or a substituted or unsubstituted phenyl;
$L^2$ is absent, $-C(=O)-$, $-N(R^D)-$, substituted or unsubstituted $C_1$-$C_4$ alkylene, or substituted or unsubstituted $C_1$-$C_4$ heteroalkylene, where if $L^2$ is substituted, then $L^2$ is substituted with $R^{12}$, where $R^{12}$ is F, $C_1$-$C_4$alkyl, $-OH$, or $-OR^D$;

ring A is a substituted or unsubstituted phenyl, or a substituted or unsubstituted monocyclic $C_1$-$C_5$ heteroarylene, where if ring A is substituted, then ring A is substituted with 1 or 2 $R^{14}$, each $R^{14}$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

$L^4$ is absent, or a substituted or unsubstituted $C_1$-$C_4$ alkylene, where if $L^4$ is substituted then $L^4$ is substituted with $R^{13}$, where $R^{13}$ is F, $C_1$-$C_4$alkyl, —OH, or —$OR^D$;

$R^5$ is H or $C_1$-$C_4$ alkyl;

each $R^A$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each $R^B$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each $R^C$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

m is 0, 1 or 2; n is 0, 1 or 2; p is 0, 1 or 2; r is 1, 2, 3, or 4.

For any and all of the embodiments, substituents are selected from among from a subset of the listed alternatives. For example, in some embodiments, $R^1$ is —$CO_2R^D$ or —C(=O)$NHSO_2R^E$. In some embodiments, $R^1$ is —$CO_2R^D$. In some embodiments, $R^1$ is —$CO_2H$. In some embodiments, $R^1$ is —C(=O)$NHSO_2R^E$. In some embodiments, $R^E$ is $C_1$-$C_6$ alkyl. In some embodiments, $R^E$ is —$CH_3$ or —$CH_2CH_3$. In some embodiments, $R^D$ is —$CH_3$ or —$CH_2CH_3$.

In some embodiments, $R^1$ is —$CO_2R^D$, or —C(=O)$NHSO_2R^E$; $L^2$ is absent, —C(=O)—, —NH—, —N($CH_3$)—, —$CH_2$—, —$CH_2CH_2$—, —CH($CH_3$)—, —$CH_2CH(CH_3)$—, —CH($CH_3$)$CH_2$—, —CH(OH)—, —CH($OR^D$)—, —$CH_2$CH(OH)—, —$CH_2$CH($OR^D$)—, —CH(OH)$CH_2$—, —CH($OR^D$)$CH_2$—, —$CH_2$NH—, —CH($CH_3$)NH—, —NHCH$_2$— or —NHCH($CH_3$)—; $L^4$ is absent, —$CH_2$—, —CH($CH_3$)—, —CH(OH)—, —$CH_2CH_2$—, —$CH_2$CH($CH_3$)—, —CH($CH_3$)$CH_2$—, —$CH_2$CH(OH)—, or —CH(OH)$CH_2$—; $R^5$ is —H, —$CH_3$ or —$CH_2CH_3$; m is 0 or 1; n is 0 or 1; r is 1, 2, or 3.

In some embodiments, $L^2$ is —NH—, —$CH_2$—, —$CH_2CH_2$—, —CH($CH_3$)—, —$CH_2$CH($CH_3$)—, —CH($CH_3$)$CH_2$—, —CH(OH)—, —$CH_2$CH(OH)—, —CH(OH) $CH_2$—, —$CH_2$NH—, —CH($CH_3$)NH—, —NHCH$_2$— or —NHCH($CH_3$)—; ring A is a substituted or unsubstituted phenyl, or a substituted or unsubstituted monocyclic $C_1$-$C_5$heteroarylene containing 1-4 N atoms, 0 or 1 O atoms and 0 or 1 S atoms, where if ring A is substituted, then ring A is substituted with 1 or 2 $R^{14}$; $L^4$ is absent, —$CH_2$—, or —CH($CH_3$)—; $R^5$ is —$CH_3$; r is 1.

In some embodiments, ring A is a substituted or unsubstituted phenyl, where if ring A is substituted, then ring A is substituted with 1 or 2 $R^{14}$.

In some embodiments, ring A is a substituted or unsubstituted monocyclic $C_1$-$C_5$heteroarylene containing 1-4 N atoms, 0 or 1 O atoms and 0 or 1 S atoms, where if ring A is substituted, then ring A is substituted with 1 or 2 $R^{14}$.

In some embodiments, ring A is a substituted or unsubstituted 5-membered monocyclic $C_1$-$C_4$heteroarylene containing 1-4 N atoms, 0 or 1 O atoms and 0 or 1 S atoms, where if ring A is substituted, then ring A is substituted with 1 or 2 $R^{14}$.

In some embodiments, ring A is a substituted or unsubstituted furanyl, a substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, or substituted or unsubstituted thiadiazolyl, where if ring A is substituted, then ring A is substituted with 1 or 2 $R^{14}$.

In some embodiments, ring A is

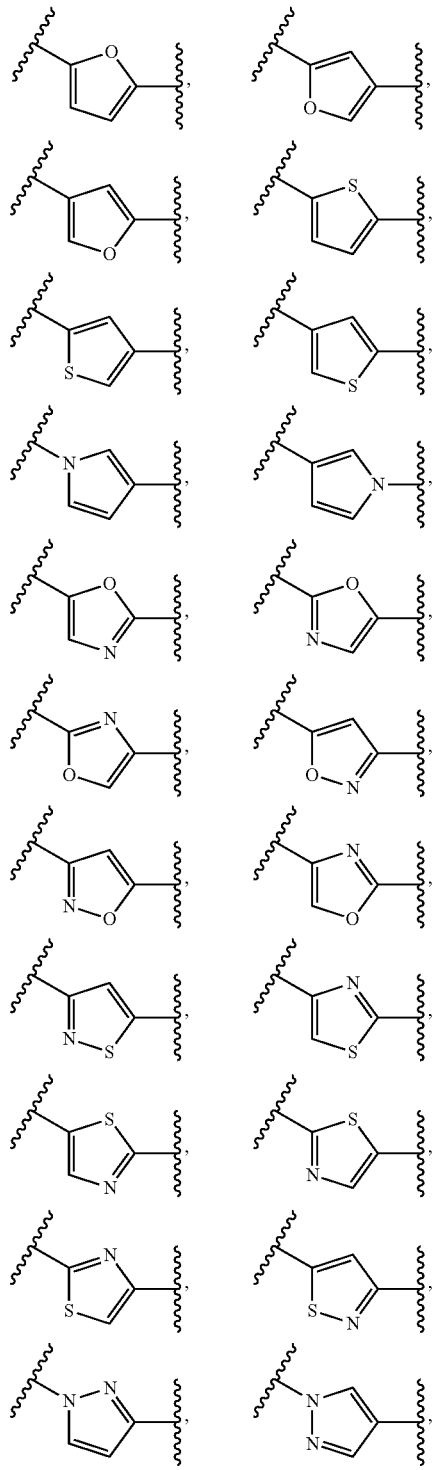

-continued
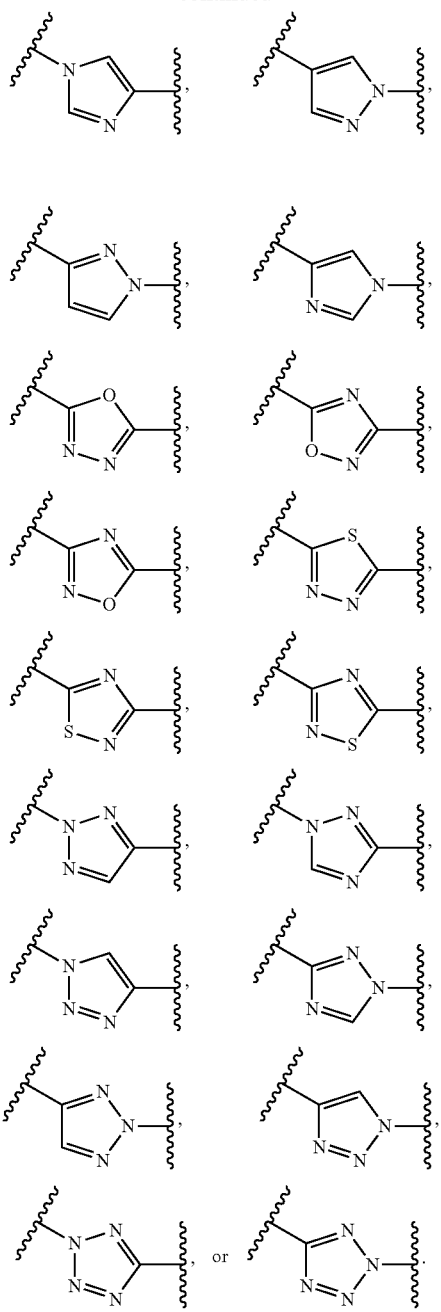
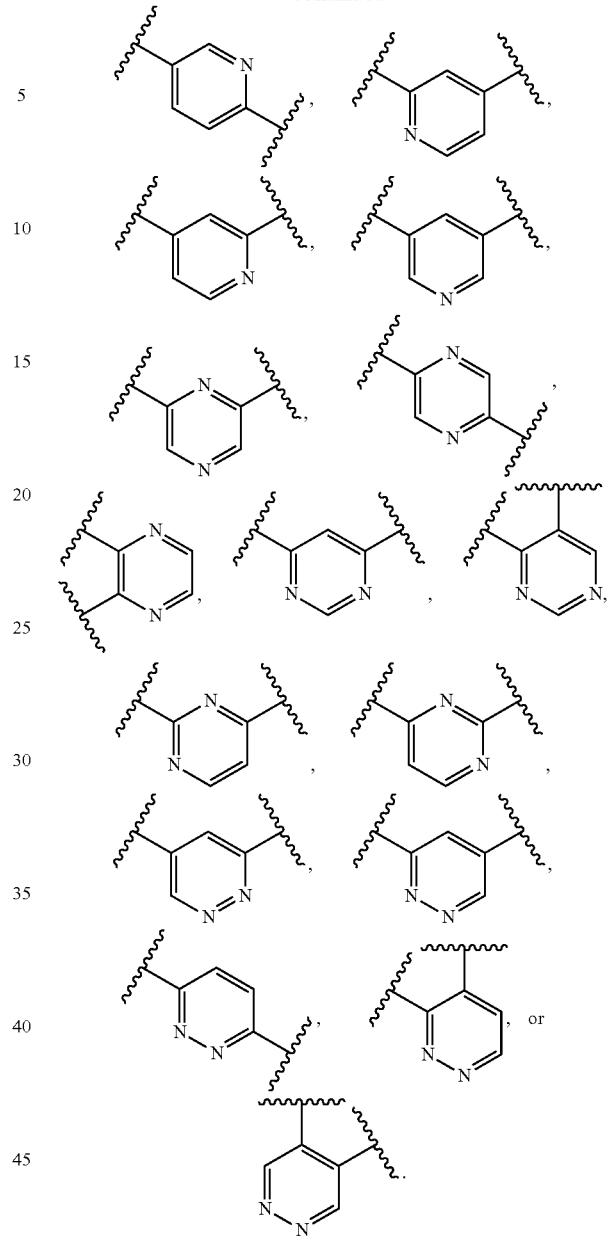
In some embodiments, ring A is a substituted or unsubstituted 6-membered monocyclic $C_3$-$C_5$heteroarylene containing 1-3 N atoms, where if ring A is substituted, then ring A is substituted with 1 or 2 $R^{14}$.
In some embodiments, ring A is
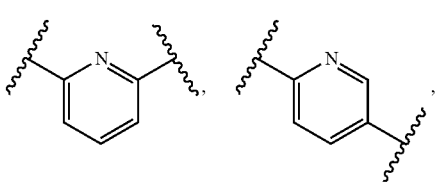
In some embodiments, the compound of Formula (I) has the structure of Formula (II):
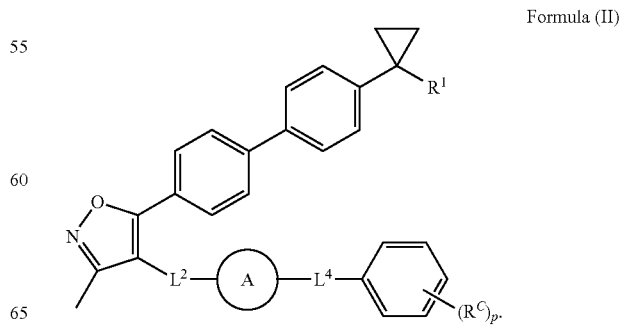
Formula (II)

In some embodiments, $R^1$ is —$CO_2R^D$, or —C(=O)NHSO$_2R^E$; $R^D$ is H or $C_1$-$C_4$ alkyl; $R^E$ is $C_1$-$C_4$ alkyl; $L^2$ is —$CH_2$—, —CH(CH$_3$)—, or —CH(OH)—; ring A is a substituted or unsubstituted 5-membered monocyclic $C_1$-$C_4$heteroarylene containing 1-4 N atoms and 0 or 1 O atoms, where if ring A is substituted, then ring A is substituted with $R^{14}$; $L^4$ is —$CH_2$— or —CH(CH$_3$)—; p is 0 or 1.

In some embodiments, $R^1$ is —$CO_2R^D$, or —C(=O)NHSO$_2R^E$; $R^D$ is H or $C_1$-$C_4$alkyl; $R^E$ is $C_1$-$C_4$alkyl; $L^2$ is —NH—, —$CH_2$—, —CH(CH$_3$)—, —CH(OH)—, —NHCH$_2$— or —NHCH(CH$_3$)—; ring A is a substituted or unsubstituted pyridinylene, where if ring A is substituted, then ring A is substituted with $R^{14}$; $L^4$ is absent, —$CH_2$—, or —CH(CH$_3$)—; p is 0 or 1.

Any combination of the groups described above for the various variables is contemplated herein. Throughout the specification, groups and substituents thereof are chosen by one skilled in the field to provide stable moieties and compounds.

In one aspect, provided are compounds presented in Tables 1 to 3 and FIGS. 1 to 11.

Compounds of Formula (I) are antagonists of at least one LPA receptor. In some embodiments, the compound of Formula (I) is an antagonist of LPA$_1$. In some embodiments, the compound of Formula (I) is an antagonist of LPA$_2$. In some embodiments, the compound of Formula (I) is an antagonist of LPA$_3$.

In some embodiments, presented herein are compounds selected from active metabolites, tautomers, solvates, pharmaceutically acceptable salts or prodrugs of a compound of Formula (I).

In some embodiments, provided is a pharmaceutical composition comprising a therapeutically effective amount of a compound of Formula (I). In some embodiments, the pharmaceutical composition also contains at least one pharmaceutically acceptable inactive ingredient.

In some embodiments, provided is a pharmaceutical composition comprising a therapeutically effective amount of a compound of Formula (I), or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents other than a compound of Formula (I).

In some embodiments, provided is a method comprising administering a compound of Formula (I) to a human with a LPA-dependent or LPA-mediated disease or condition. In some embodiments, the human is already being administered one or more additional therapeutically active agents other than a compound of Formula (I). In some embodiments, the method further comprises administering one or more additional therapeutically active agents other than a compound of Formula (I).

In some embodiments, the one or more additional therapeutically active agents other than a compound of Formula (I) are selected from: corticosteroids, immunosuppressants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase A$_1$ inhibitors, phospholipase A$_2$ inhibitors, and lysophospholipase D (lysoPLD) inhibitors, autotaxin inhibitors, decongestants, antihistamines, mucolytics, anticholinergics, antitussives, expectorants, and 13-2 agonists.

In another aspect is the use of a compound of Formula (I) in the treatment of a disease, disorder or condition in which the activity of at least one LPA receptor contributes to the pathology and/or symptoms of the disease or condition. In one embodiment of this aspect, the LPA receptor is selected from LPA$_1$, LPA$_2$, LPA$_3$, LPA$_4$, LPA$_5$ and LPA$_6$. In some embodiments, the LPA receptor is LPA$_1$ or LPA$_2$ or LPA$_3$. In some embodiments, the disease or condition is any of the diseases or conditions specified herein.

Also provided is a method of inhibiting the physiological activity of LPA in a mammal comprising administering a therapeutically effective amount of a compound of Formula (I) or a pharmaceutically acceptable salt thereof to the mammal in need thereof.

In one aspect, is a method for treating or preventing a LPA-dependent or LPA-mediated disease or condition in a mammal comprising administering a therapeutically effective amount of a compound of Formula (I).

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, is a method for treating or preventing cancer in a mammal comprising administering a therapeutically effective amount of a compound of Formula (I) or a pharmaceutically acceptable salt thereof to the mammal in need thereof.

In one aspect, is a method for treating or preventing fibrosis in a mammal comprising administering a therapeutically effective amount of a compound of Formula (I) or a pharmaceutically acceptable salt thereof to the mammal in need thereof.

In one aspect, is a method for treating or preventing lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal comprising administering a therapeutically effective amount of a compound of Formula (I) or a pharmaceutically acceptable salt thereof to the mammal in need thereof.

In one aspect, provided is a method for the treatment or prevention of organ fibrosis in a mammal comprising administering a therapeutically effective amount of a compound of Formula (I) or a pharmaceutically acceptable salt thereof to a mammal in need thereof. In some embodiments, the organ fibrosis comprises lung fibrosis, renal fibrosis, or hepatic fibrosis.

In one aspect, provided is a method of improving lung function in a mammal comprising administering a therapeutically effective amount of a compound of Formula (I) or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In one aspect, compounds disclosed herein are used to treat Raynaud's phenomenon. Raynaud's phenomenon comprises both Raynaud's disease (where the phenomenon is idiopathic) and Raynaud's syndrome, where it is caused by some other instigating factor.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulomatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NASH), metabolic and auto-immune.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formula (I). In various embodiments, each agent is administered in any order, including simultaneously.

In any of the embodiments disclosed herein, the mammal is a human.

In some embodiments, compounds provided herein are administered to a human. In some embodiments, compounds provided herein are orally administered to a human.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Figure 1:
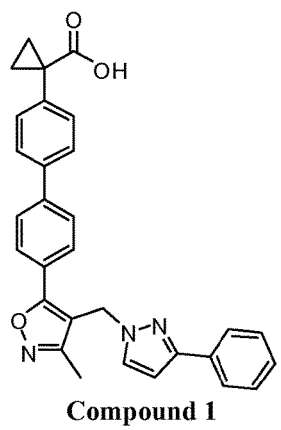
FIG. 1. Illustrative examples of compounds described herein.
Figure 1:
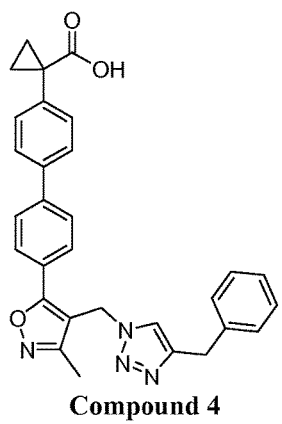
Figure 1:
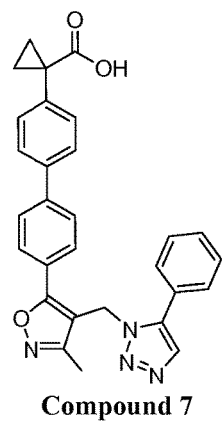
Figure 1:
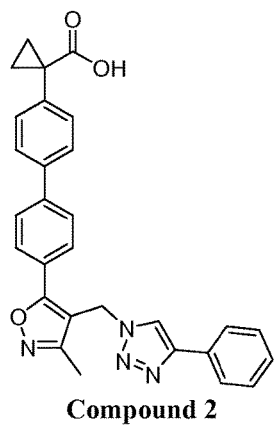
Figure 1:
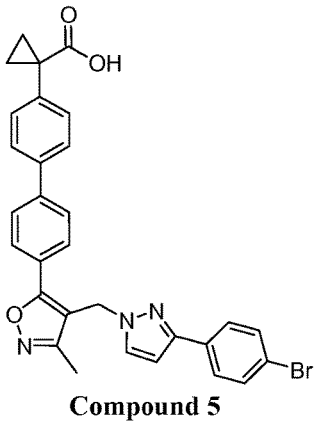
Figure 1:
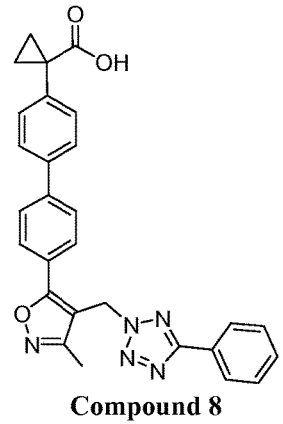
Figure 1:
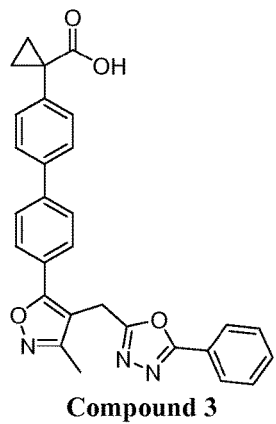
Figure 1:
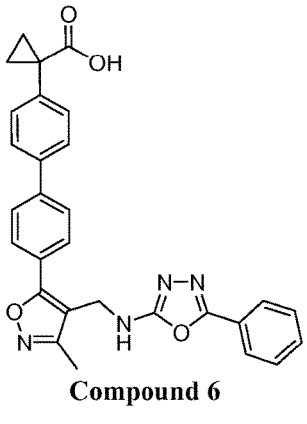

Lysophospholipids (such as lysophosphatidic acid (LPA)) affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors with LPA mediates a range of downstream signaling cascades. The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. $LPA_1$, $LPA_2$, and $LPA_3$ share high amino acid sequence similarity.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing.

Tissue injury initiates a complex series of host wound-healing responses; if successful, these responses restore normal tissue structure and function. If not, these responses can lead to tissue fibrosis and loss of function.

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF. CTGF is a profibrotic cytokine, signaling down-stream and in parallel with TGFβ.

LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterizes this fibrotic condition.

The LPA-LPA2 pathway contributes to the activation of the TGF-β pathway in pulmonary fibrosis. In some embodiments, compounds that inhibit LPA2 show efficacy in the treatment of lung fibrosis. In some embodiments, compounds that inhibit both LPA1 and LPA2 show improved efficacy in the treatment of lung fibrosis compared to compounds which inhibit only LPA1 or LPA2.

LPA and $LPA_1$ are involved in the etiology of kidney fibrosis. In mice invalidated for the $LPA_1$ receptor ($LPA_1$ (−/−), the development of renal fibrosis was significantly attenuated. Unilateral ureteral obstruction (UUO; animal model of renal fibrosis) mice treated with the LPA receptor antagonist Ki16425 closely resembled the $LPA_1$ (−/−) mice.

LPA is implicated in liver disease and fibrosis. Plasma LPA levels and serum autotoxin are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA is present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells.

LPA is implicated in myocardial infarction and cardiac fibrosis. Serum LPA levels are increased in patients following myocardial infarction (MI) and LPA stimulates proliferation and collagen production (fibrosis) by rat cardiac fibroblasts. Both LPA1 and LPA3 receptors are highly expressed in human heart tissue.

In one aspect, compounds of Formula (I) are used to treat or prevent fibrosis in a mammal. In one aspect, compounds of Formula (I) are used to treat or prevent fibrosis of an organ or tissue in a mammal.

The terms "fibrosis" or "fibrosing disorder", as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formula (I): atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, compounds of Formula (I) are used to treat a dermatological disorders in a mammal. Dermatological disorders include, but are not limited to, proliferative or inflammatory disorders of the skin such as, atopic dermatitis, bullous disorders, collagenosis, psoriasis, psoriatic lesions, dermatitis, contact dermatitis, eczema, urticaria, rosacea, wound healing, scarring, hypertrophic scarring, keloids, Kawasaki Disease, rosacea, Sjögren-Larsson Syndrome, urticaria.

LPA is released following tissue injury. $LPA_1$ plays a role in the initiation of neuropathic pain. In one aspect, compounds of Formula (I) are used in the treatment of pain in a mammal. In one aspect, the pain is acute pain or chronic pain. In another aspect, the pain is neuropathic pain. In another aspect, the pain is cancer pain. In one aspect, compounds of Formula (I) are used in the treatment of fibromyalgia.

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers.

LPA contributes to tumorigenesis by increasing motility and invasiveness of cells. LPA has been implicated in the initiation or progression of ovarian cancer. LPA is present at significant concentrations (2-80 µM) in the ascitic fluid of ovarian cancer patients. LPA receptors (LPA2 and LPA3) are also overexpressed in ovarian cancer cells as compared to normal ovarian surface epithelial cells. LPA has also been implicated in the initiation or progression of prostate cancer, breast cancer, melanoma, head and neck cancer, bowel cancer (colorectal cancer), thyroid cancer, glioblastoma, and other cancers.

LPA receptors mediate both migration of and invasion by pancreatic cancer cell lines: Ki16425 and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al., *J. Biol. Chem.*, 279:6595-6605 (2004)).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signalling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. $LPA_1$ is implicated in bone metastasis (Boucharaba et al., *Proc. Natl. Acad. Sci USA*, 103:9643-9648 (2006)).

In one aspect, a compound of Formula (I) is used in the treatment of cancer. In one aspect, compounds of Formula (I) are used in the treatment of malignant and benign proliferative disease. In one aspect, compounds of Formula (I) are used to prevent or reduce proliferation of tumor cells, invasion and metastasis of carcinomas, pleural mesothelioma or peritoneal mesothelioma, cancer pain, bone metastases. In one aspect is a method of treating cancer in a mammal, the method comprising administering to the mammal a compound of Formula (I) and a second therapeutic agent, wherein the second therapeutic agent is an anti-cancer agent. In some embodiments, radiation therapy is also used.

The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

In one aspect, LPA is a contributor to the pathogenesis of respiratory diseases. Proinflammatory effects of LPA include degranulation of mast cells, contraction of smooth-muscle cells and release of cytokines from dendritic cells. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and 11-8 has been shown to exacerbate airway inflammation and airway remodeling of asthmatics. LPA1, LPA2 and LPA3 receptors have all been shown to contribute to the LPA-induced IL-8 production.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In one aspect, the effects of LPA are mediated through $LPA_1$ and/or $LPA_3$. In one aspect, compounds of Formula (I) are used in the treatment of various allergic disorders in a mammal. In one aspect, compounds of Formula (I) are used in the treatment of respiratory diseases, disorders or conditions in a mammal. In one aspect, compounds of Formula (I) are used in the treatment of asthma in a mammal. In one aspect, compounds of Formula (I) are used in the treatment of chronic asthma in a mammal.

The term "respiratory disease", as used herein, refers to diseases affecting the organs that are involved in breathing, such as the nose, throat, larynx, eustachian tubes, trachea, bronchi, lungs, related muscles (e.g., diaphragm and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In one aspect, presented herein is the use of compounds of Formula (I) in the treatment or prevention of chronic obstructive pulmonary disease in a mammal comprising administering to the mammal at least once an effective amount of at least one compound of Formula (I). In addition, chronic obstructive pulmonary disease includes, but is not limited to, chronic bronchitis or emphysema, pulmonary hypertension, interstitial lung fibrosis and/or airway inflammation, and cystic fibrosis.

The nervous system is a major locus for $LPA_1$ expression. In one aspect, provided is a compound of Formula (I) for use in the treatment or prevention of a nervous system disorder in a mammal. The term "nervous system disorder", as used herein includes, but is not limited to, Alzheimer's Disease, cerebral edema, cerebral ischemia, stroke, multiple sclerosis, neuropathies, Parkinson's Disease, multiple sclerosis, retinal ischemia, post-surgical cognitive dysfunction, migraine, peripheral neuropathy/neuropathic pain, spinal cord injury, cerebral edema and head injury.

Angiogenesis, the formation of new capillary networks from pre-existing vasculature, is normally invoked in wound healing, tissue growth and myocardial angiogenesis after ischemic injury. Peptide growth factors and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy.

In one aspect, compounds of Formula (I) are used to treat or prevent cardiovascular disease in mammal, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formula (I) or pharmaceutical composition or medicament which includes a compound of Formula (I). In some embodiments, provided herein are methods for preventing or treating Raynaud's phenomenon.

In one aspect, provided herein are methods for reducing cardiac reperfusion injury following myocardial ischemia and/or endotoxic shock comprising administering at least once to the mammal an effective amount of at least one compound of Formula (I).

In one aspect, provided herein are methods for reducing the constriction of blood vessels in a mammal comprising administering at least once to the mammal an effective amount of at least one compound of Formula (I).

In one aspect, provided herein are methods for lowering or preventing an increase in blood pressure of a mammal comprising administering at least once to the mammal an effective amount of at least one compound of Formula (I).

LPA is associated with various inflammatory/immune diseases. In one aspect, compounds of Formula (I) are used to treat or prevent inflammation in a mammal. In one aspect, antagonists of $LPA_1$ and/or $LPA_3$ find use in the treatment or prevention of inflammatory/immune disorders in a mammal.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjögren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formula (I). In certain embodiments, the subject already has a LPA-dependent or LPA-mediated disease or condition at the time of administration, or is at risk of developing a LPA-dependent or LPA-mediated disease or condition.

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formula (I).

In certain aspects, are methods for the treatment of cystitis, including, e.g., interstitial cystitis, comprising administering at least once to the mammal a therapeutically effective amount of at least one compound of Formula (I).

In accordance with one aspect, methods described herein include the diagnosis or determination of whether or not a patient is suffering from a LPA-dependent or LPA-mediated disease or condition by administering to the subject a therapeutically effective amount of a compound of Formula (I) and determining whether or not the patient responds to the treatment.

In one aspect provided herein are compounds of Formula (I), pharmaceutically acceptable salts, pharmaceutically acceptable prodrugs, and pharmaceutically acceptable solvates thereof, which are antagonists of at least one LPA receptor (e.g., $LPA_1$, $LPA_2$, $LPA_3$) and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, adult respiratory distress syndrome, myocardial infarction, aneurysm, stroke, and cancer.

In one aspect, compounds of Formula (I) are used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of compounds of Formula (I) in the treatment or prevention of ocular inflammation and allergic conjunctivitis, vernal keratoconjunctivitis, and papillary conjunctivitis in a mammal comprising administering at least once to the mammal an effective amount of at least one compound of Formula (I).

In one aspect, presented herein is the use of compounds of Formula (I) in the treatment or prevention of Sjögren disease or inflammatory disease with dry eyes in a mammal comprising administering at least once to the mammal an effective amount of at least one compound of Formula (I).

In one aspect, LPA and LPA receptors (e.g., $LPA_1$) are involved in the pathogenesis of osteoarthritis. In one aspect, presented herein is the use of compounds of Formula (I) in the treatment or prevention of osteoarthritis in a mammal comprising administering at least once to the mammal an effective amount of at least one compound of Formula (I).

In one aspect, LPA receptors (e.g., $LPA_1$, $LPA_3$) contribute to the pathogenesis of rheumatoid arthritis. In one aspect, presented herein is the use of compounds of Formula (I) in the treatment or prevention of rheumatoid arthritis in a mammal comprising administering at least once to the mammal an effective amount of at least one compound of Formula (I).

In one aspect, LPA receptors (e.g., $LPA_1$) contribute to adipogenesis. In one aspect, presented herein is the use of compounds of Formula (I) in the promotion of adipose tissue formation in a mammal comprising administering at least once to the mammal an effective amount of at least one compound of Formula (I).

Compounds

In one aspect, provided herein is a compound having the structure of Formula (I) or a pharmaceutically acceptable salt thereof:

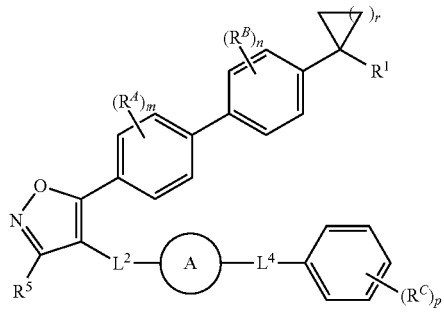

Formula (I)

wherein,
$R^1$ is $-CO_2R^D$, $-C(=O)NHSO_2R^E$, $-C(=O)N(R^D)_2$, $-CN$, or tetrazolyl;

$R^D$ is H or $C_1$-$C_6$ alkyl;
$R^E$ is $C_1$-$C_6$ alkyl or a substituted or unsubstituted phenyl;
$L^2$ is absent, $-C(=O)-$, $-N(R^D)-$, substituted or unsubstituted $C_1$-$C_4$ alkylene, or substituted or unsubstituted $C_1$-$C_4$ heteroalkylene, where if $L^2$ is substituted, then $L^2$ is substituted with $R^{12}$, where $R^{12}$ is F, $C_1$-$C_4$alkyl, $-OH$, or $-OR^D$;
ring A is a substituted or unsubstituted phenyl, or a substituted or unsubstituted monocyclic $C_1$-$C_5$heteroarylene, where if ring A is substituted, then ring A is substituted with 1 or 2 $R^{14}$, each $R^{14}$ is independently selected from halogen, $-CN$, $-OH$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
$L^4$ is absent, or a substituted or unsubstituted $C_1$-$C_4$ alkylene, where if $L^4$ is substituted then $L^4$ is substituted with $R^{13}$, where $R^{13}$ is F, $C_1$-$C_4$alkyl, $-OH$, or $-OR^D$;
$R^5$ is H or $C_1$-$C_4$ alkyl;
each $R^A$ is independently selected from halogen, $-CN$, $-OH$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
each $R^B$ is independently selected from halogen, $-CN$, $-OH$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
each $R^C$ is independently selected from halogen, $-CN$, $-OH$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
m is 0, 1 or 2; n is 0, 1 or 2; p is 0, 1 or 2; r is 1, 2, 3, or 4.

For any and all of the embodiments, substituents are selected from among from a subset of the listed alternatives. For example, in some embodiments, $R^1$ is $-CO_2R^D$ or $-C(=O)NHSO_2R^E$. In some embodiments, $R^1$ is $-CO_2R^D$. In some embodiments, $R^1$ is $-CO_2H$. In some embodiments, $R^1$ is $-C(=O)NHSO_2R^E$. In some embodiments, $R^E$ is $C_1$-$C_6$ alkyl. In some embodiments, $R^E$ is $-CH_3$ or $-CH_2CH_3$. In some embodiments, $R^D$ is H, $-CH_3$ or $-CH_2CH_3$. In some embodiments, $R^D$ is H.

In some embodiments, $R^5$ is $C_1$-$C_4$alkyl. In some embodiments, $R^5$ is H, $-CH_3$, or $-CH_2CH_3$. In some embodiments, $R^5$ is $-CH_3$, or $-CH_2CH_3$. In some embodiments, $R^5$ is $-CH_3$. In some embodiments, $R^5$ is H.

In some embodiments, $L^2$ is absent, $-C(=O)-$, $-N(R^D)-$, substituted or unsubstituted $C_1$-$C_4$ alkylene, or substituted or unsubstituted $C_1$-$C_4$ heteroalkylene, where if $L^2$ is substituted, then $L^2$ is substituted with $R^{12}$. In some embodiments, $L^2$ is $-N(R^D)-$, substituted or unsubstituted $C_1$-$C_2$ alkylene, or substituted or unsubstituted $C_1$-$C_2$ heteroalkylene, where if $L^2$ is substituted, then $L^2$ is substituted with $R^{12}$. In some embodiments, $L^2$ is $-N(H)-$, $-N(CH_3)-$, substituted or unsubstituted methylene, or substituted or unsubstituted ethylene, where if $L^2$ is substituted, then $L^2$ is substituted with $R^{12}$. In some embodiments, $L^2$ is $-N(H)-$. In some embodiments, $L^2$ is substituted or unsubstituted methylene, where if $L^2$ is substituted, then $L^2$ is substituted with $R^{12}$.

In some embodiments, $L^2$ is selected from a bond, $C_1$-$C_4$ alkylene, $-C(=O)-$, $-CH(OH)-$, $-CH(OR^D)-$, $-CH_2CH(OH)-$, $-CH_2CH(OR^D)-$, $-CH_2S-$, $-CH_2S(O)-$, $-CH_2S(O)_2-$, $-SCH_2-$, $-S(O)CH_2-$, $-S(O)_2CH_2-$, $-CH_2O-$, $-OCH_2-$, $-S(O)_2CH_2-$, $-N(H)-$, $-CH_2N(H)-$, or $-N(H)CH_2-$.

In some embodiments, $L^2$ is absent, $-C(=O)-$, $-NH-$, $-N(CH_3)-$, $-CH_2-$, $-CH_2CH_2-$, $-CH(CH_3)-$, $-CH_2CH(CH_3)-$, $-CH(CH_3)CH_2-$, $-CH(OH)-$, $-CH(OR^D)-$, $-CH_2CH(OH)-$, $-CH_2CH(OR^D)-$, $-CH(OH)CH_2-$, $-CH(OR^D)CH_2-$, $-CH_2NH-$, $-CH(CH_3)NH-$, $-NHCH_2-$ or $-NHCH$ (CH$_3$)—. In some embodiments, L$^2$ is —NH—, —N(CH$_3$)—, —CH$_2$—, —CH(CH$_3$)—, —CH(OH)—, —CH(OR$^D$)—, —CH$_2$NH—, —CH(CH$_3$)NH—, —NHCH$_2$— or —NHCH(CH$_3$)—. In some embodiments, L$^2$ is —NH—, —N(CH$_3$)—, —CH$_2$NH—, —CH(CH$_3$)NH—, —NHCH$_2$— or —NHCH(CH$_3$)—. In some embodiments, L$^2$ is —NH—. In some embodiments, L$^2$ is —CH$_2$—, —CH(CH$_3$)—, —CH(OH)—, —CH(OR$^D$)—, —CH$_2$NH—, —CH(CH$_3$)NH—, —NHCH$_2$— or —NHCH(CH$_3$)—. In some embodiments, L$^2$ is —CH$_2$—, —CH(CH$_3$)—, —CH(OH)—, or —CH(OR$^D$)—. In some embodiments, L$^2$ is —CH$_2$— or —CH(OH)—. In some embodiments, L$^2$ is —CH(OH)—. In some embodiments, L$^2$ is —CH$_2$—.

In some embodiments, R$^{12}$ is F, —CH$_3$, —CH$_2$CH$_3$, —OH, —OCH$_3$, or —OCH$_2$CH$_3$. In some embodiments, R$^{12}$ is —CH$_3$, or —OH.

In some embodiments, R$^1$ is —CO$_2$R$^D$, or —C(=O)NHSO$_2$R$^E$; L$^2$ is absent, —C(=O)—, —NH—, —N(CH$_3$)—, —CH$_2$—, —CH$_2$CH$_2$—, —CH(CH$_3$)—, —CH$_2$CH(CH$_3$)—, —CH(CH$_3$)CH$_2$—, —CH(OH)—, —CH(OR$^D$)—, —CH$_2$CH(OH)—, —CH$_2$CH(OR$^D$)—, —CH(OH)CH$_2$—, —CH(OR$^D$)CH$_2$—, —CH$_2$NH—, —CH(CH$_3$)NH—, —NHCH$_2$— or —NHCH(CH$_3$)—; L$^4$ is absent, —CH$_2$—, —CH(CH$_3$)—, —CH(OH)—, —CH$_2$CH$_2$—, —CH$_2$CH(CH$_3$)—, —CH(CH$_3$)CH$_2$—, —CH$_2$CH(OH)—, or —CH(OH)CH$_2$—; R$^5$ is —H, —CH$_3$ or —CH$_2$CH$_3$.

In some embodiments, each R$^A$ is independently selected from halogen, —OH, —CH$_3$, —CH$_2$CH$_3$, —CF$_3$, —OCF$_3$, —OCH$_3$ and —OCH$_2$CH$_3$. In some embodiments, each R$^A$ is halogen, —OH, —CH$_3$, —CH$_2$CH$_3$, —CF$_3$, —OCF$_3$, —OCH$_3$ or —OCH$_2$CH$_3$.

In some embodiments, each R$^B$ is independently selected from halogen, —OH, —CH$_3$, —CH$_2$CH$_3$, —CF$_3$, —OCF$_3$, —OCH$_3$ and —OCH$_2$CH$_3$. In some embodiments, each R$^B$ is halogen, —OH, —CH$_3$, —CH$_2$CH$_3$, —CF$_3$, —OCF$_3$, —OCH$_3$ or —OCH$_2$CH$_3$.

In some embodiments, each R$^C$ is halogen, —OH, —CH$_3$, —CH$_2$CH$_3$, —CF$_3$, —OCF$_3$, —OCH$_3$, —OCH$_2$CH$_3$, —CH$_2$OCH$_3$, —CH$_2$OCH$_2$CH$_3$, or —CH$_2$N(CH$_3$)$_2$. In some embodiments, each R$^C$ is independently selected from halogen, —OH, —CH$_3$, —CH$_2$CH$_3$, —CF$_3$, —OCF$_3$, —OCH$_3$ and —OCH$_2$CH$_3$.

In some embodiments, m is 0 or 1; n is 0 or 1; r is 1, 2, or 3.

In some embodiments, m is 0 or 1. In some embodiments, m is 0. In some embodiments, n is 0 or 1. In some embodiments, n is 0. In some embodiments, r is 1, 2, or 3. In some embodiments, r is 1 or 2. In some embodiments, r is 1.

In some embodiments, ring A is a substituted or unsubstituted phenyl, or a substituted or unsubstituted monocyclic C$_1$-C$_5$heteroarylene, where if ring A is substituted, then ring A is substituted with 1 or 2 R$^{14}$.

In some embodiments, ring A is a substituted or unsubstituted phenyl, or a substituted or unsubstituted monocyclic C$_1$-C$_5$heteroarylene containing 1-4 N atoms, 0 or 1 O atoms and 0 or 1 S atoms, where if ring A is substituted, then ring A is substituted with 1 or 2 R$^{14}$.

In some embodiments, ring A is a substituted or unsubstituted monocyclic C$_1$-C$_5$heteroarylene containing 1-4 N atoms, 0 or 1 O atoms and 0 or 1 S atoms, where if ring A is substituted, then ring A is substituted with 1 or 2 R$^{14}$.

In some embodiments, ring A is a substituted or unsubstituted 5-membered monocyclic C$_1$-C$_4$heteroarylene containing 1-4 N atoms, 0 or 1 O atoms and 0 or 1 S atoms, where if ring A is substituted, then ring A is substituted with 1 or 2 R$^{14}$.

In some embodiments, ring A is a substituted or unsubstituted 6-membered monocyclic C$_3$-C$_5$heteroarylene containing 1-3 N atoms, where if ring A is substituted, then ring A is substituted with 1 or 2 R$^{14}$.

In some embodiments, ring A is a substituted or unsubstituted monocyclic ring wherein the groups -L$^2$- and -L$^4$- are in a 1,2-relationship on ring A (i.e., an ortho relationship).

In some embodiments, ring A is a substituted or unsubstituted monocyclic ring wherein the groups -L$^2$- and -L$^4$- are in a 1,3-relationship on ring A (i.e., a meta relationship).

In some embodiments, ring A is a substituted or unsubstituted monocyclic ring wherein the groups -L$^2$- and -L$^4$- are in a 1,4-relationship on ring A (i.e., a para relationship).

In some embodiments, ring A is unsubstituted or monosubstituted with R$^{14}$. In some embodiments, ring A is unsubstituted. In some embodiments, ring A is monosubstituted with R$^{14}$.

In some embodiments, L$^4$ is absent, or a substituted or unsubstituted methylene, or substituted or unsubstituted ethylene, where if L$^4$ is substituted, then L$^4$ is substituted with R$^{13}$. In some embodiments, L$^4$ is absent. In some embodiments, L$^4$ is a substituted or unsubstituted methylene, where if L$^4$ is substituted, then L$^4$ is substituted with R$^{13}$. In some embodiments, L$^4$ is a substituted or unsubstituted ethylene, where if L$^4$ is substituted, then L$^4$ is substituted with R$^{13}$.

In some embodiments, R$^{13}$ is F, —CH$_3$, —CH$_2$CH$_3$, —OH, —OCH$_3$, or —OCH$_2$CH$_3$. In some embodiments, R$^{13}$ is —CH$_3$.

In some embodiments, L$^4$ is absent, —CH$_2$—, or —CH(CH$_3$)—.

In some embodiments, L$^2$ is —NH—, —CH$_2$—, —CH$_2$CH$_2$—, —CH(CH$_3$)—, —CH$_2$CH(CH$_3$)—, —CH(CH$_3$)CH$_2$—, —CH(OH)—, —CH$_2$CH(OH)—, —CH(OH)CH$_2$—, —CH$_2$NH—, —CH(CH$_3$)NH—, —NHCH$_2$— or —NHCH(CH$_3$)—; ring A is a substituted or unsubstituted phenyl, or a substituted or unsubstituted monocyclic C$_1$-C$_5$heteroarylene containing 1-4 N atoms, 0 or 1 O atoms and 0 or 1 S atoms, where if ring A is substituted, then ring A is substituted with 1 or 2 R$^{14}$; L$^4$ is absent, —CH$_2$—, or —CH(CH$_3$)—; R$^5$ is —CH$_3$; r is 1.

In some embodiments, ring A is a substituted or unsubstituted phenyl, where if ring A is substituted, then ring A is substituted with 1 or 2 R$^{14}$.

In some embodiments, ring A is a substituted or unsubstituted monocyclic C$_1$-C$_5$heteroarylene containing 1-4 N atoms, 0 or 1 O atoms and 0 or 1 S atoms, where if ring A is substituted, then ring A is substituted with 1 or 2 R$^{14}$.

In some embodiments, ring A is a substituted or unsubstituted 5-membered monocyclic C$_1$-C$_4$heteroarylene containing 1-4 N atoms, 0 or 1 O atoms and 0 or 1 S atoms, where if ring A is substituted, then ring A is substituted with 1 or 2 R$^{14}$.

In some embodiments, ring A is a substituted or unsubstituted furanyl, a substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, or substituted or unsubstituted thiadiazolyl, where if ring A is substituted, then ring A is substituted with 1 or 2 $R^{14}$.

In some embodiments, each $R^{14}$ is independently selected from halogen, —CN, —OH, —$CH_3$, —$CH_2CH_3$, —$CF_3$, —$OCF_3$, —$OCH_3$ and —$OCH_2CH_3$. In some embodiments, each $R^{14}$ is halogen, —CN, —OH, —$CH_3$, —$CH_2CH_3$, —$CF_3$, —$OCF_3$, —$OCH_3$ or —$OCH_2CH_3$. In some embodiments, each $R^{14}$ is independently selected from halogen, —OH, and —$CH_3$. In some embodiments, $R^{14}$ is halogen, —OH, or —$CH_3$. In some embodiments, each $R^{14}$ is independently selected from halogen and —$CH_3$.

In some embodiments, ring A is

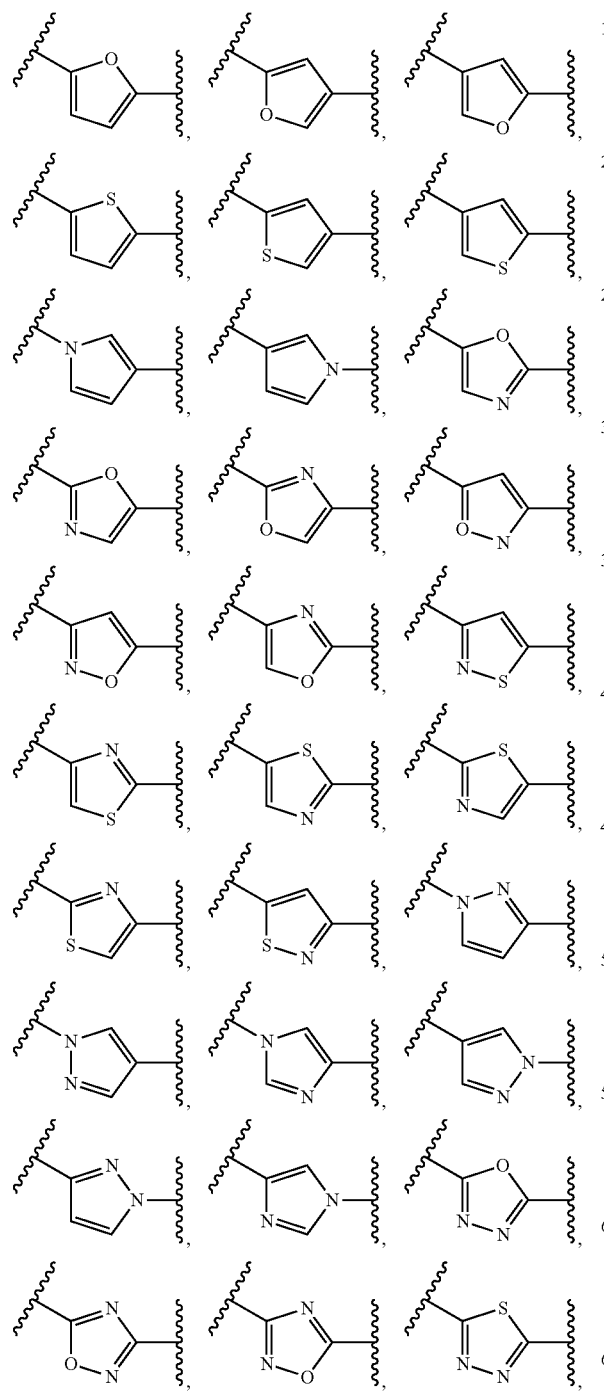

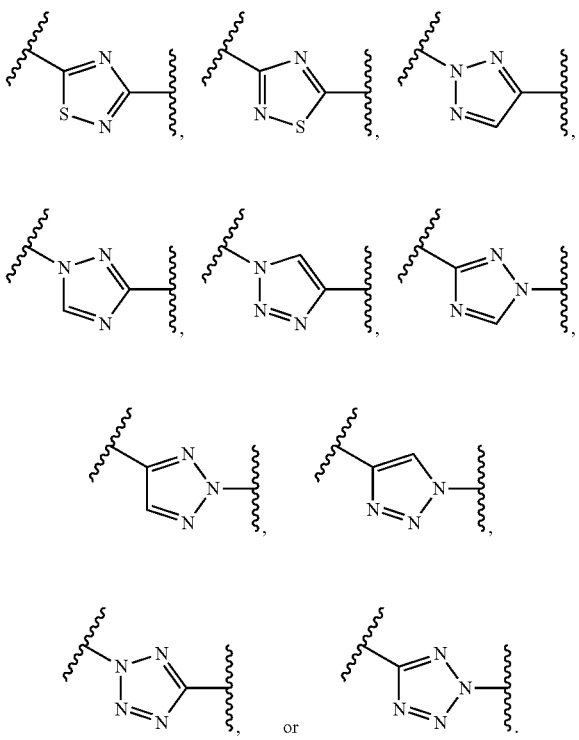

In some embodiments, ring A is a substituted or unsubstituted 6-membered monocyclic $C_3$-$C_5$heteroarylene containing 1-3 N atoms, where if ring A is substituted, then ring A is substituted with 1 or 2 $R^{14}$.

In some embodiments, ring A is a substituted or unsubstituted pyridinylene, a substituted or unsubstituted pyridazinylene, a substituted or unsubstituted pyrimidinylene, a substituted or unsubstituted pyrazinylene, or a substituted or unsubstituted triazinylene, where if ring A is substituted, then ring A is substituted with 1 or 2 $R^{14}$.

In some embodiments, ring A is a substituted or unsubstituted pyridinylene, where if ring A is substituted, then ring A is substituted with 1 or 2 $R^{14}$.

In some embodiments, ring A is

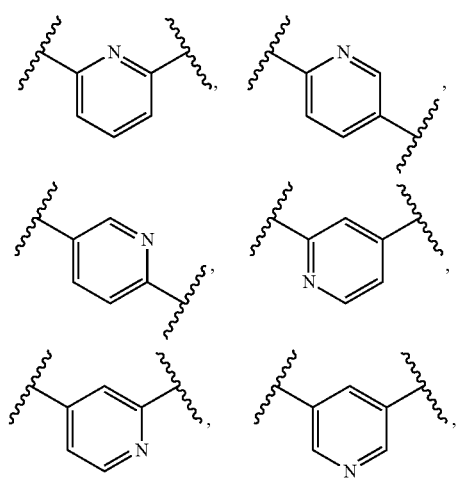

-continued

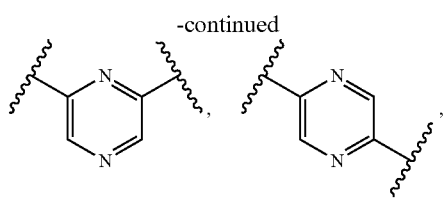

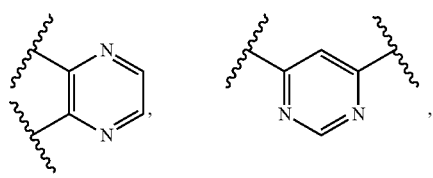

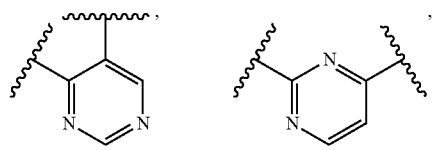

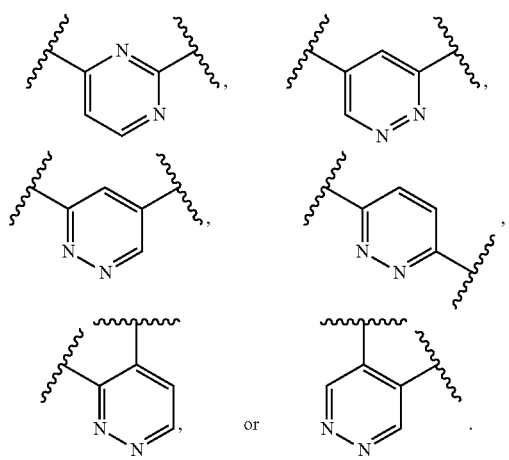

In some embodiments, the compound of Formula (I) has the structure of Formula (II):

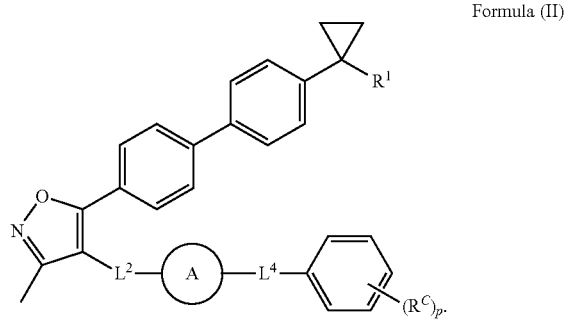

Formula (II)

In some embodiments, $R^1$ is —$CO_2R^D$, or —C(=O)NHSO$_2R^E$; $R^D$ is H or $C_1$-$C_4$ alkyl; $R^E$ is $C_1$-$C_4$ alkyl; $L^2$ is —$CH_2$—, —$CH(CH_3)$—, or —$CH(OH)$—; ring A is a substituted or unsubstituted 5-membered monocyclic $C_1$-$C_4$heteroarylene containing 1-4 N atoms and 0 or 1 O atoms, where if ring A is substituted, then ring A is substituted with $R^{14}$, $R^{14}$ is halogen, —CN, —OH, —$CH_3$, —$CH_2CH_3$, —$CF_3$, —$OCF_3$, —$OCH_3$ or —$OCH_2CH_3$; $L^4$ is —$CH_2$— or —$CH(CH_3)$—; p is 0 or 1.

In some embodiments, $R^1$ is —$CO_2R^D$, or —C(=O)NHSO$_2R^E$; $R^D$ is H or $C_1$-$C_4$alkyl; $R^E$ is $C_1$-$C_4$alkyl; $L^2$ is —NH—, —$CH_2$—, —$CH(CH_3)$—, —$CH(OH)$—, —$NHCH_2$— or —$NHCH(CH_3)$—; ring A is a substituted or unsubstituted pyridinylene, where if ring A is substituted, then ring A is substituted with $R^{14}$, $R^{14}$ is halogen, —CN, —OH, —$CH_3$, —$CH_2CH_3$, —$CF_3$, —$OCF_3$, —$OCH_3$ or —$OCH_2CH_3$; $L^4$ is absent, —$CH_2$—, or —$CH(CH_3)$—; p is 0 or 1.

In some embodiments, p is 0, 1 or 2. In some embodiments, p is 0 or 1. In some embodiments, p is 0. In some embodiments, p is 1.

In some embodiments, is phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2-bromophenyl, 3-bromophenyl, 2,4-dichlorophenyl, 2-hydroxyphenyl, 3-hydroxyphenyl, 4-hydroxyphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, 4-methylphenyl, 2-cyanophenyl, 3-cyanophenyl, or 4-cyanophenyl.

In some embodiments, -$L^2$- is as described in Table(s) 1, 2 and/or 3.

In some embodiments, -$L^4$- is as described in Table(s) 1, 2 and/or 3.

In some embodiments, ring A is as described in Table(s)$_1$, Table 2 and/or 3.

In some embodiments, is $R^2$ as defined in Table(s) 1, 2 and/or 3.

Any combination of the groups described above for the various variables is contemplated herein. Throughout the specification, groups and substituents thereof are chosen by one skilled in the field to provide stable moieties and compounds.

Figure 2:
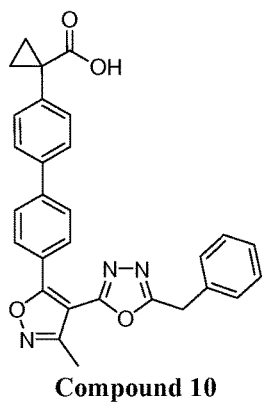
FIG. 2. Illustrative examples of compounds described herein.
Figure 2:
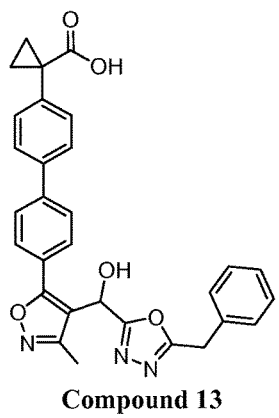
Figure 2:
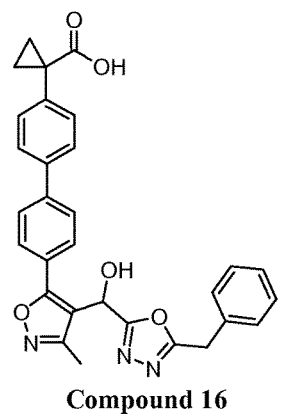
Figure 2:
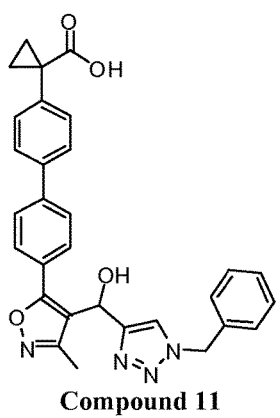
Figure 2:
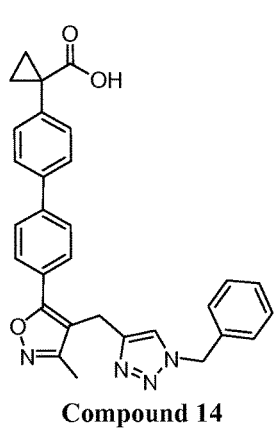
Figure 2:
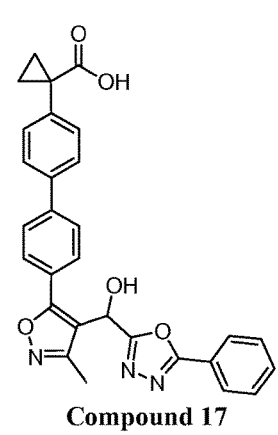
Figure 2:
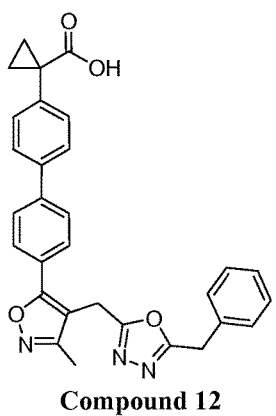
Figure 2:
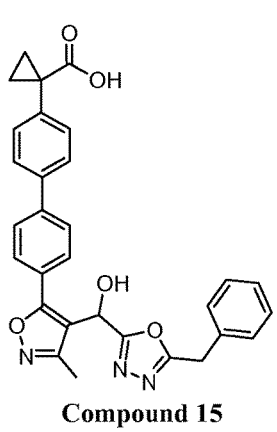
Figure 2:
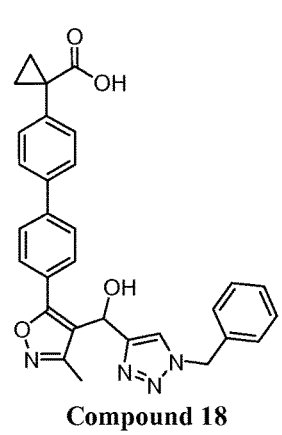
Figure 3:
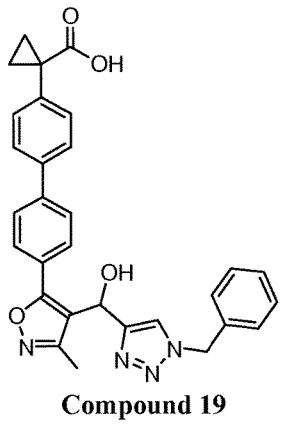
FIG. 3. Illustrative examples of compounds described herein.
Figure 3:
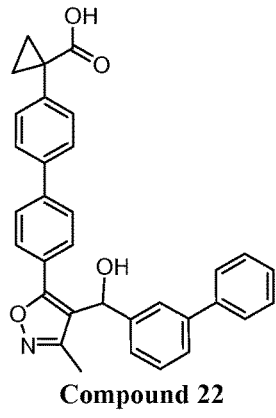
Figure 3:
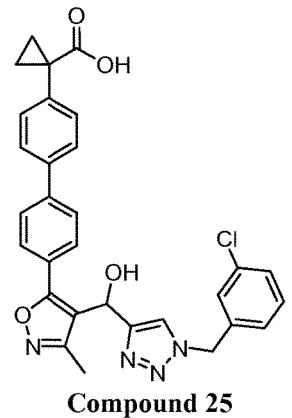
Figure 3:
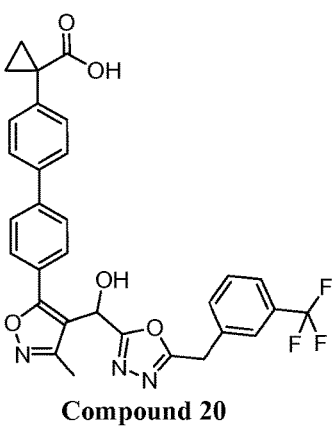
Figure 3:
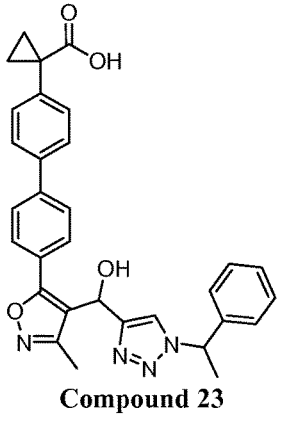
Figure 3:
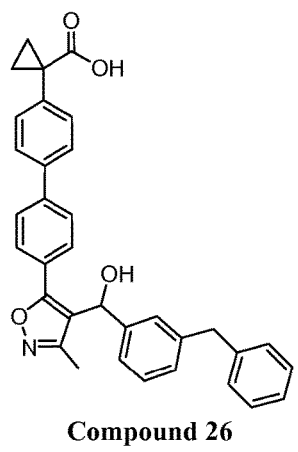
Figure 3:
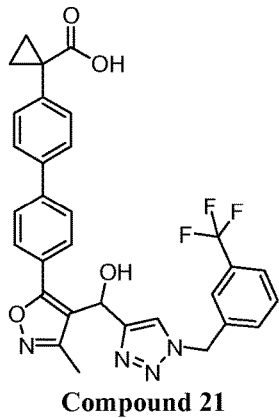
Figure 3:
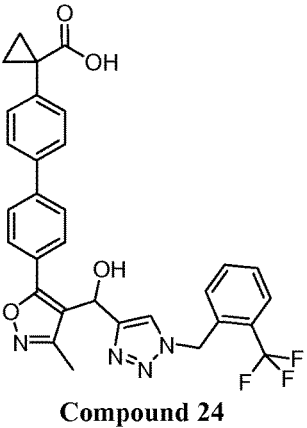
Figure 3:
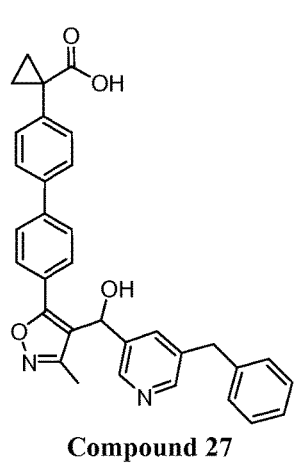
Figure 4:
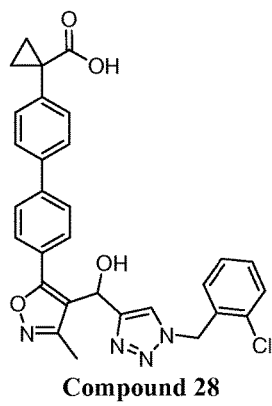
FIG. 4. Illustrative examples of compounds described herein.
Figure 4:
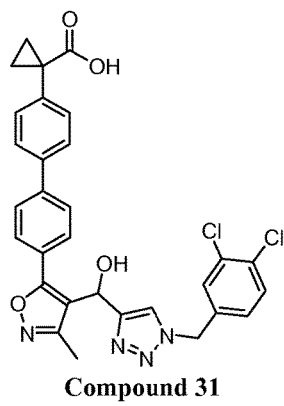
Figure 4:
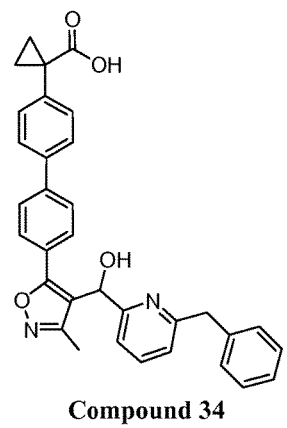
Figure 4:
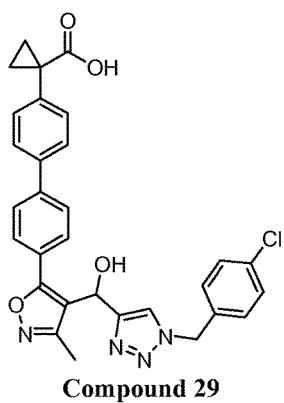
Figure 4:
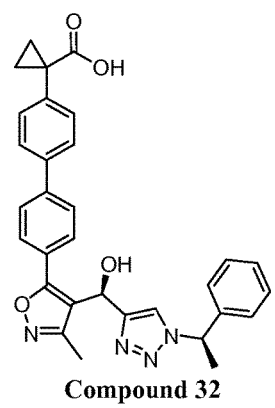
Figure 4:
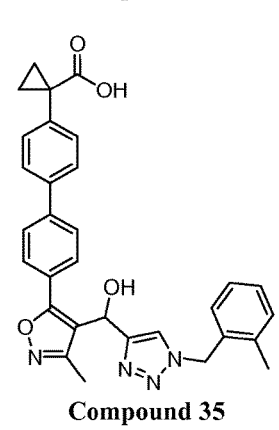
Figure 4:
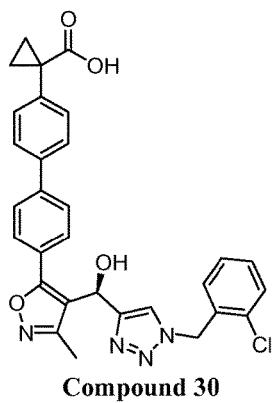
Figure 4:
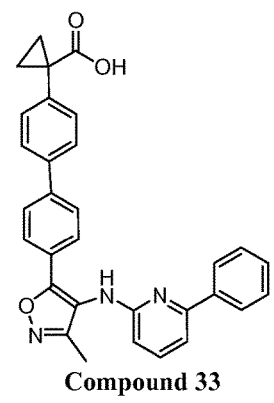
Figure 4:
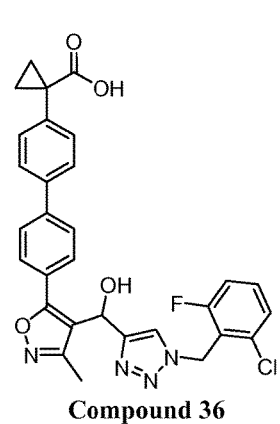
Figure 5:
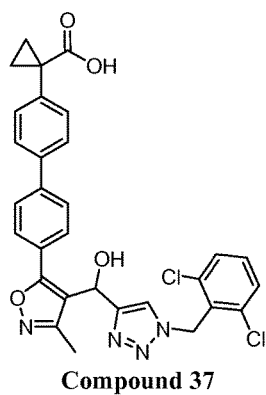
FIG. 5. Illustrative examples of compounds described herein.
Figure 5:
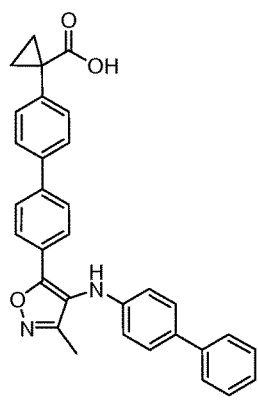
Figure 5:
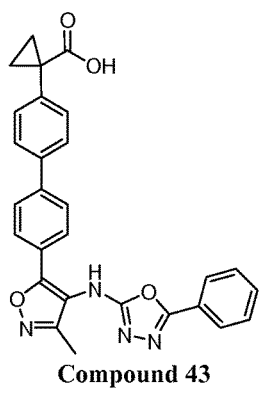
Figure 5:
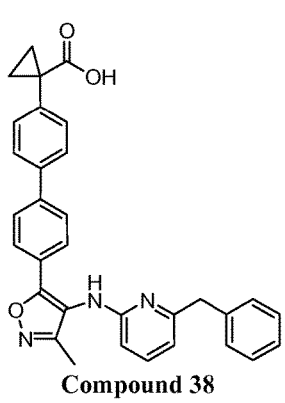
Figure 5:
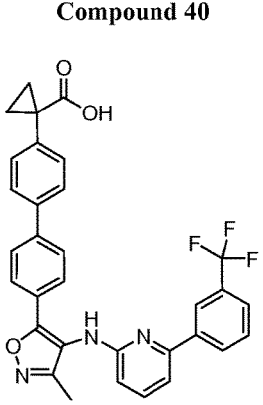
Figure 5:
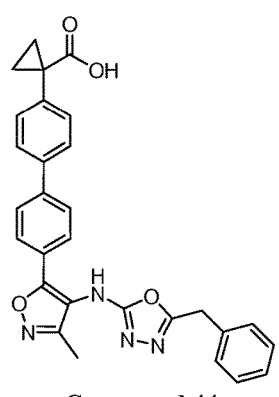
Figure 5:
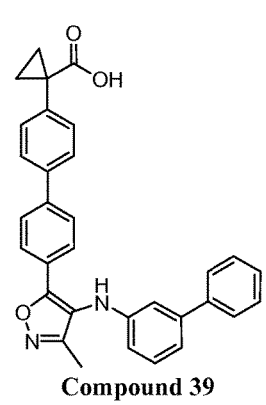
Figure 5:
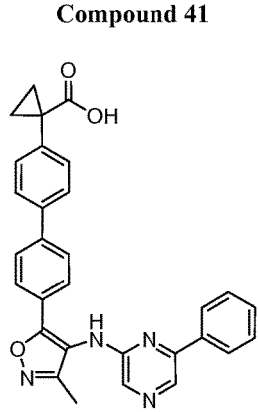
Figure 5:
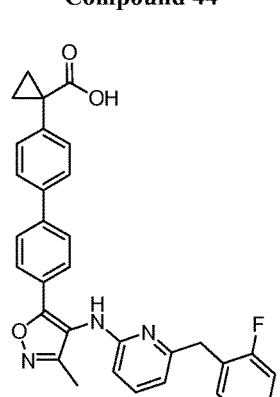
Figure 6:
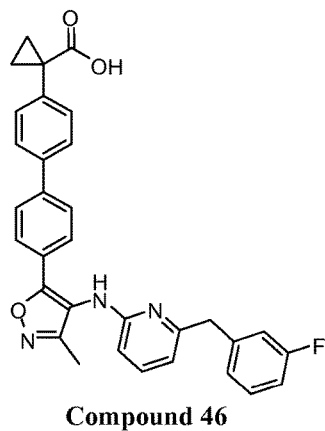
FIG. 6. Illustrative examples of compounds described herein.
Figure 6:
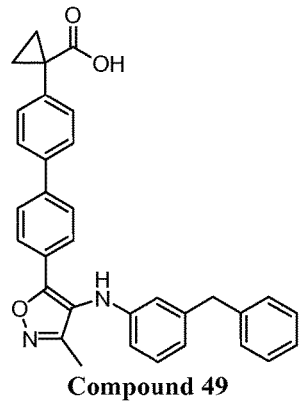
Figure 6:
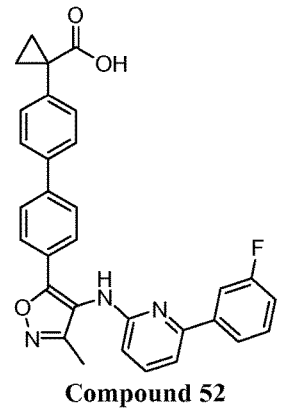
Figure 6:
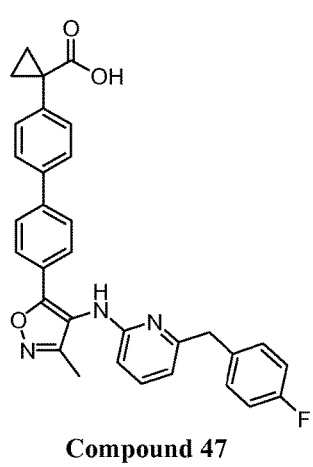
Figure 6:
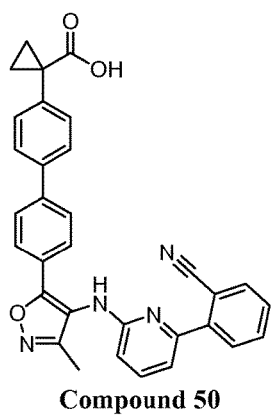
Figure 6:
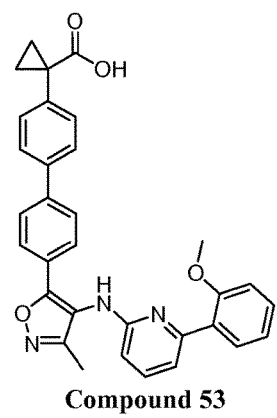
Figure 6:
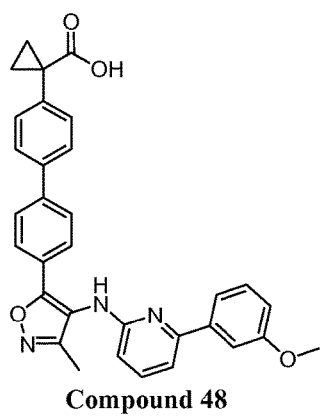
Figure 6:
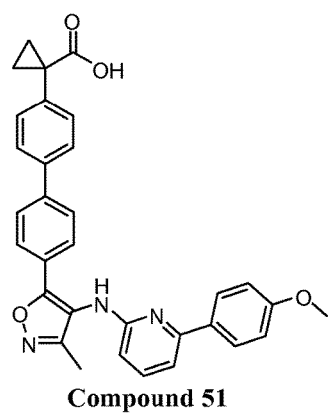
Figure 6:
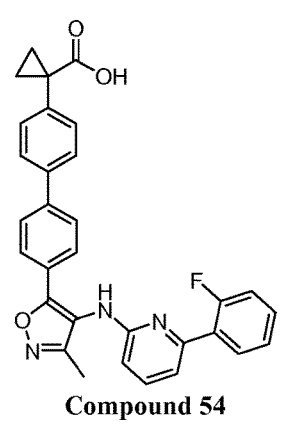
Figure 7:
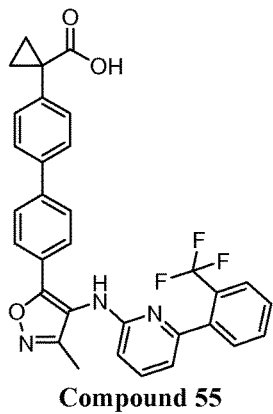
FIG. 7. Illustrative examples of compounds described herein.
Figure 7:
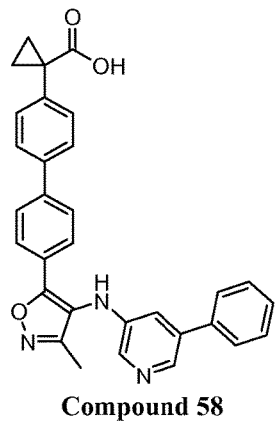
Figure 7:
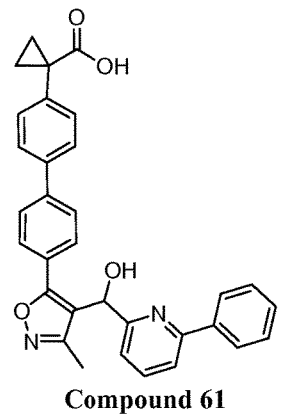
Figure 7:
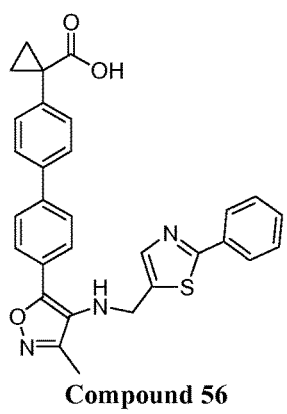
Figure 7:
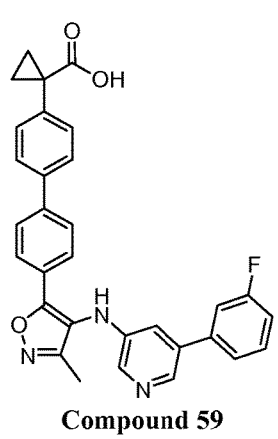
Figure 7:
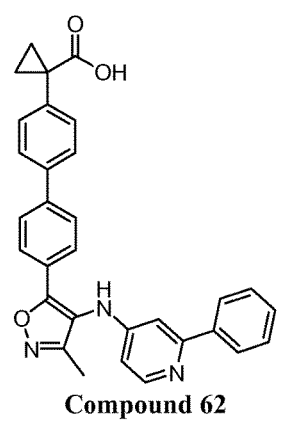
Figure 7:
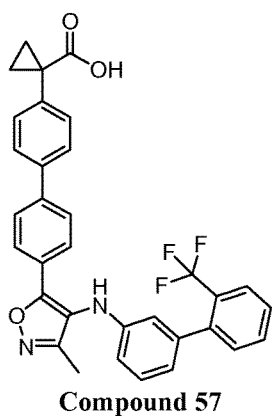
Figure 7:
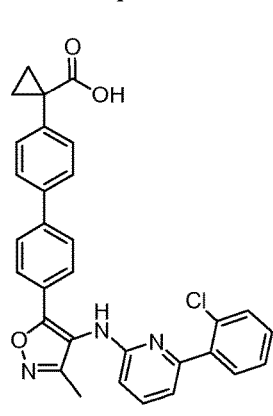
Figure 7:
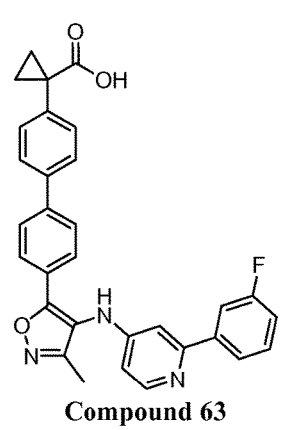
Figure 8:
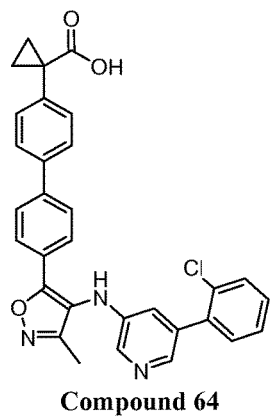
FIG. 8. Illustrative examples of compounds described herein.
Figure 8:
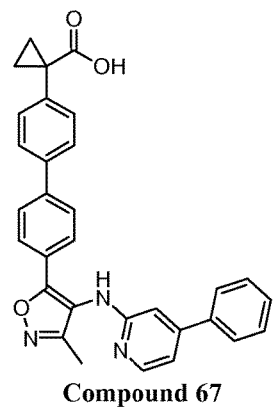
Figure 8:
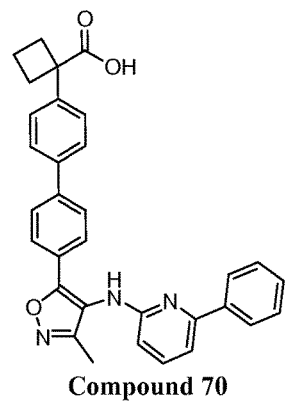
Figure 8:
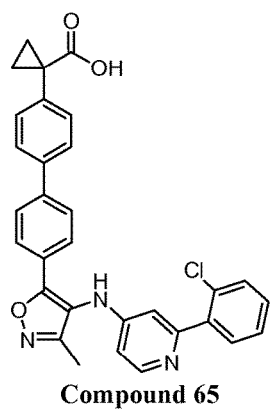
Figure 8:
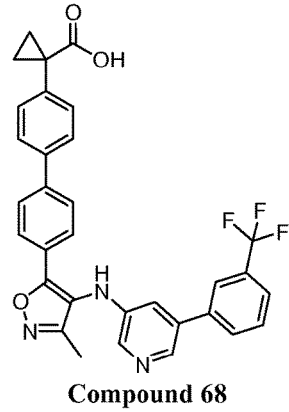
Figure 8:
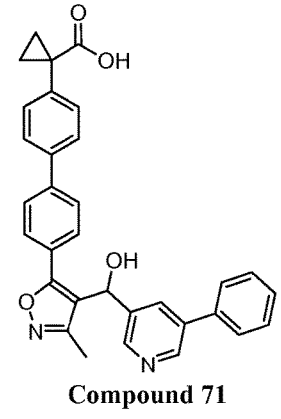
Figure 8:
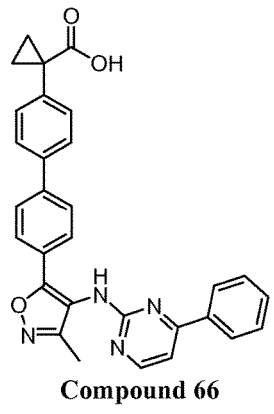
Figure 8:
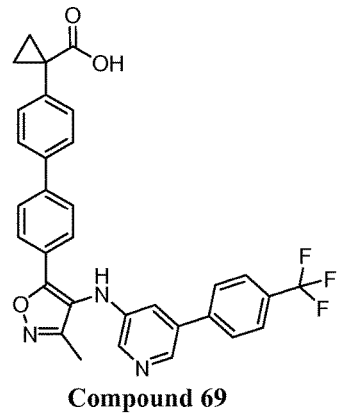
Figure 8:
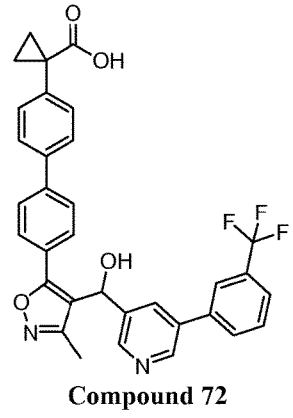
Figure 9:
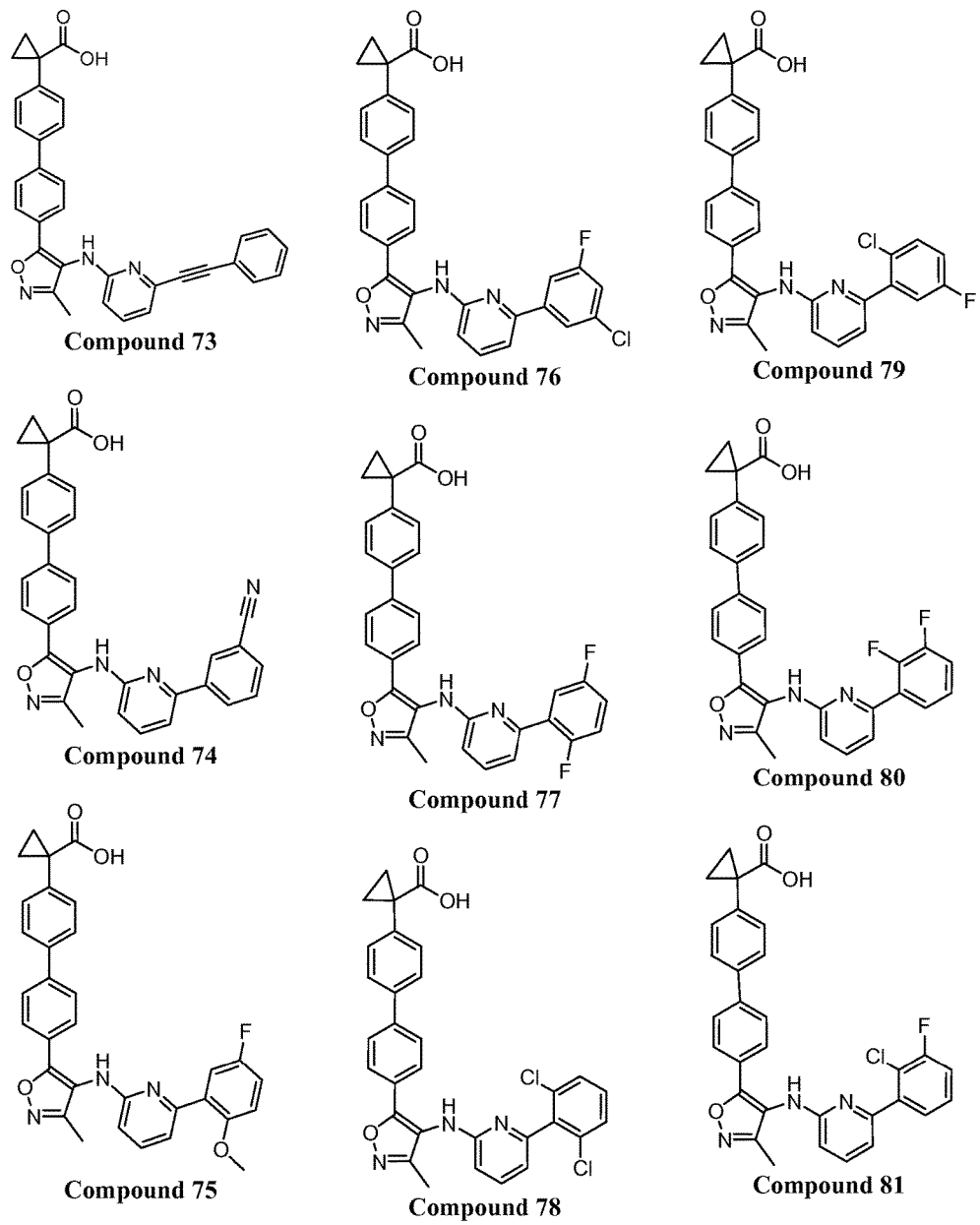
FIG. 9. Illustrative examples of compounds described herein.
Figure 10:
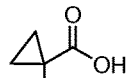
FIG. 10. Illustrative examples of compounds described herein.
Figure 10:
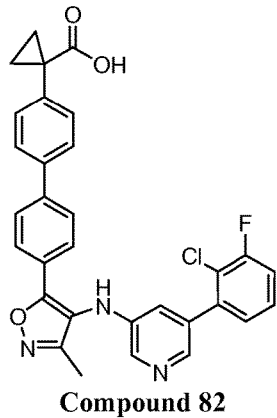
Figure 10:
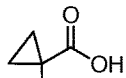
Figure 10:
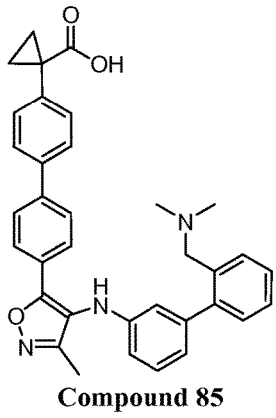
Figure 10:
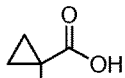
Figure 10:
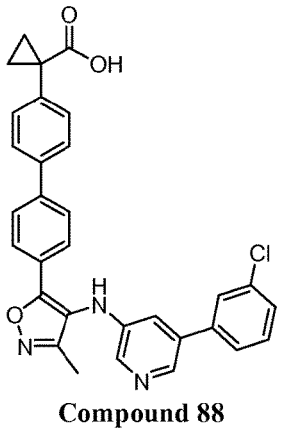
Figure 10:
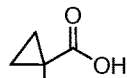
Figure 10:
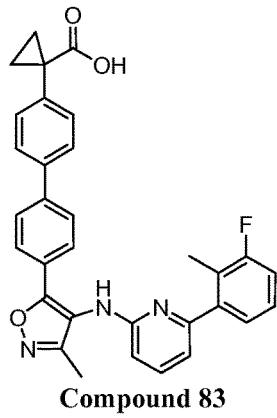
Figure 10:
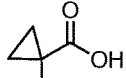
Figure 10:
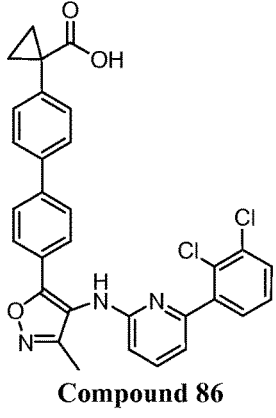
Figure 10:
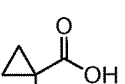
Figure 10:
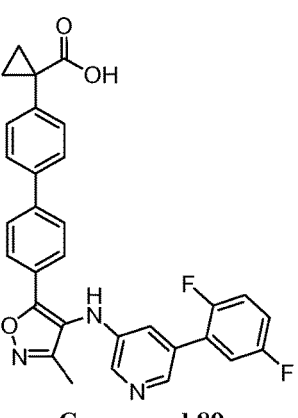
Figure 10:
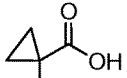
Figure 10:
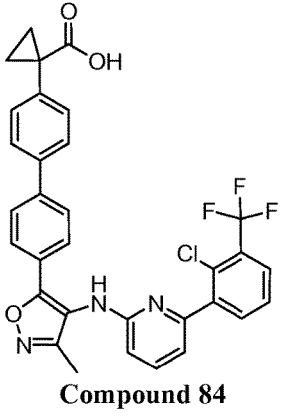
Figure 10:
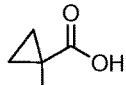
Figure 10:
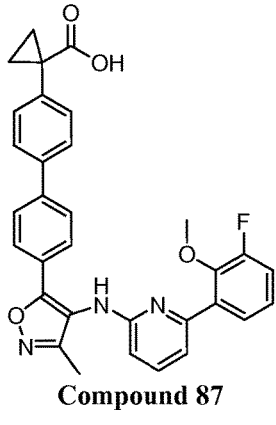
Figure 10:
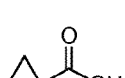
Figure 10:
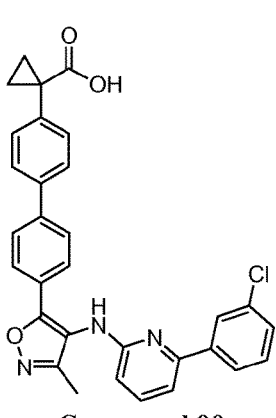
Figure 11:
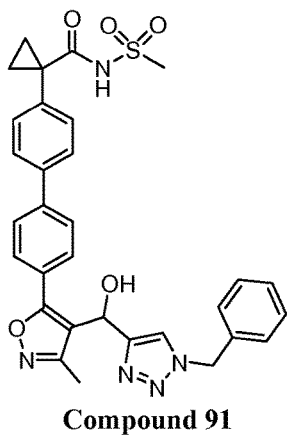
FIG. 11. Illustrative examples of compounds described herein.
Figure 11:
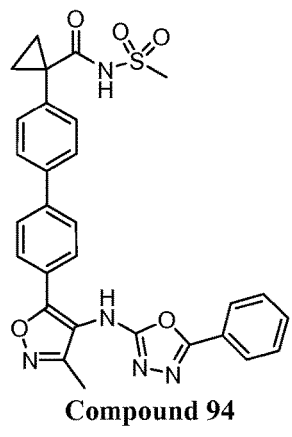
Figure 11:
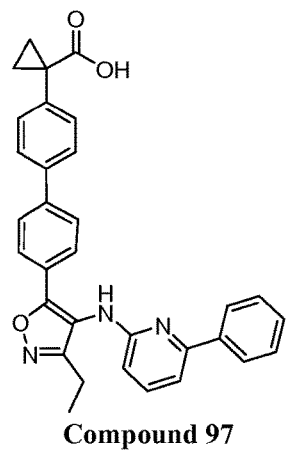
Figure 11:
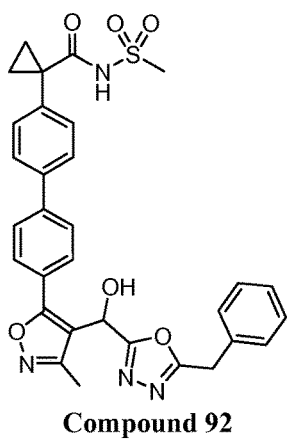
Figure 11:
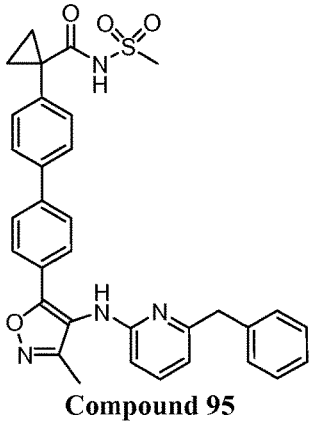
Figure 11:
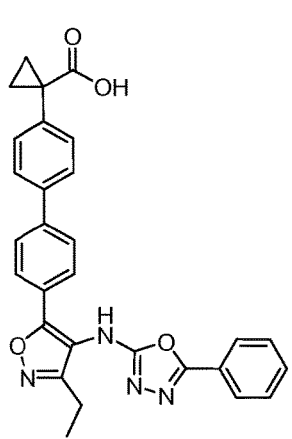
Figure 11:
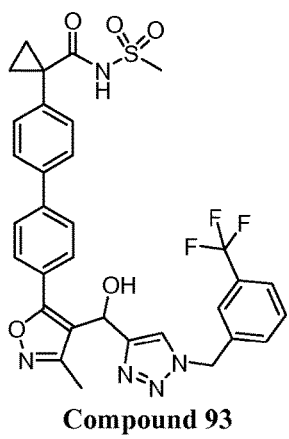
Figure 11:
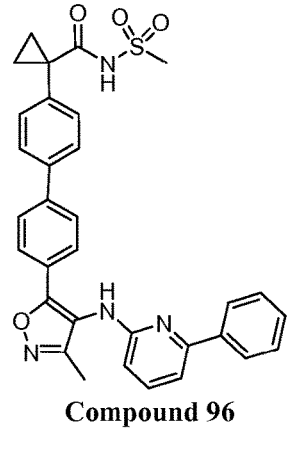

In some embodiments, compounds of Formula (I) include, but are not limited to, those described in Tables 1 to 3 and FIGS. 1 to 11.

TABLE 1

[Structure: 3-methyl-isoxazole with 5-position attached to biphenyl, biphenyl terminal position attached to cyclopropane-CO₂H (with subscript r); isoxazole 4-position bears -L²-A-L⁴-R²]

| Cmpd No | r | L² | A | L⁴ | R² | M + H* |
|---|---|---|---|---|---|---|
| 1 | 1 | —CH₂— | Pyrazol-1,3-diyl | — | Phenyl | 476 |
| 2 | 1 | —CH₂— | [1,2,3]Triazol-1,4-diyl | — | Phenyl | 477 |
| 3 | 1 | —CH₂— | [1,3,4]Oxadiazol-2,5-diyl | — | Phenyl | 478 |
| 4 | 1 | —CH₂— | [1,2,3]Triazol-1,4-diyl | —CH₂— | Phenyl | 491 |
| 5 | 1 | —CH₂— | Pyrazol-1,3-diyl | — | 4-Bromo-phenyl | 554 |
| 6 | 1 | —CH₂—NH— | [1,3,4]Oxadiazol-2,5-diyl | — | Phenyl | 493 |
| 7 | 1 | —CH₂— | [1,2,3]Triazol-1,5-diyl | — | Phenyl | 477 |
| 8 | 1 | —CH₂— | Tetrazol-2,5-diyl | — | Phenyl | 478 |
| 9 | 1 | —CH₂— | Pyrazol-1,4-diyl | — | Phenyl | 476 |
| 10 | 1 | — | [1,3,4]Oxadiazol-2,5-diyl | —CH₂— | Phenyl | 478 |
| 11 | 1 | —CH(OH) | 1H-[1,2,3]Triazol-1,4-diyl | —CH₂— | Phenyl | 507 |
| 12 | 1 | —CH₂— | [1,3,4]Oxadiazol-2,5-diyl | —CH₂— | Phenyl | 492 |
| 13 | 1 | —CH(OH)— | [1,3,4]Oxadiazol-2,5-diyl | —CH₂— | Phenyl | 508 |
| 14 | 1 | —CH₂— | 1H-[1,2,3]Triazol-1,4-diyl | —CH₂— | Phenyl | 491 |
| 15 | 1 | (S)—CH(OH)— | [1,3,4]Oxadiazol-2,5-diyl | —CH₂— | Phenyl | 508 |
| 16 | 1 | (R)—CH(OH)— | [1,3,4]Oxadiazol-2,5-diyl | —CH₂— | Phenyl | 508 |
| 17 | 1 | —CH(OH)— | [1,3,4]Oxadiazol-2,5-diyl | — | Phenyl | 494 |
| 18 | 1 | (S)—CH(OH)— | 1H-[1,2,3]Triazol-1,4-diyl | —CH₂— | Phenyl | 507 |
| 19 | 1 | (R)—CH(OH)— | 1H-[1,2,3]Triazol-1,4-diyl | —CH₂— | Phenyl | 507 |
| 20 | 1 | —CH(OH)— | [1,3,4]Oxadiazol-2,5-diyl | —CH₂— | 4-Trifluoromethyl-phenyl | 576 |
| 21 | 1 | —CH(OH)— | 1H-[1,2,3]Triazol-1,4-diyl | —CH₂— | 3-Trifluoromethyl-phenyl | 575 |
| 22 | 1 | —CH(OH)— | Phenyl-1,3-diyl | — | Phenyl | 502 |
| 23 | 1 | —CH(OH)— | 1H-[1,2,3]Triazol-1,4-diyl | —CH(CH₃)— | Phenyl | 521 |
| 24 | 1 | —CH(OH)— | 1H-[1,2,3]Triazol-1,4-diyl | —CH₂— | 2-Trifluoromethyl-phenyl | |
| 25 | 1 | —CH(OH)— | 1H-[1,2,3]Triazol-1,4-diyl | —CH₂— | 3-Chloro-phenyl | 541 |
| 26 | 1 | —CH(OH)— | Phenyl-1,3-diyl | —CH₂— | Phenyl | 516 |
| 27 | 1 | —CH(OH)— | Pyridine-3,5-diyl | —CH₂— | Phenyl | 517 |
| 28 | 1 | —CH(OH)— | 1H-[1,2,3]Triazol-1,4-diyl | —CH₂— | 2-Chloro-phenyl | 541 |
| 29 | 1 | —CH(OH)— | 1H-[1,2,3]Triazol-1,4-diyl | —CH₂— | 4-Chloro-phenyl | 541 |
| 30 | 1 | (R)—CH(OH)— | 1H-[1,2,3]Triazol-1,4-diyl | —CH₂— | 2-Chloro-phenyl | 541 |
| 31 | 1 | —CH(OH)— | 1H-[1,2,3]Triazol-1,4-diyl | —CH₂— | 3,4-Dichloro-phenyl | |
| 32 | 1 | (R)—CH(OH)— | 1H-[1,2,3]Triazol-1,4-diyl | —CH(CH₃)— (R) | Phenyl | 521 |
| 33 | 1 | —NH— | Pyridine-2,6-diyl | — | Phenyl | 488 |
| 34 | 1 | —CH(OH)— | Pyridine-2,6-diyl | —CH₂— | Phenyl | 517 |
| 35 | 1 | —CH(OH)— | 1H-[1,2,3]Triazol-1,4-diyl | —CH₂— | 2-Methyl-phenyl | 521 |
| 36 | 1 | —CH(OH)— | 1H-[1,2,3]Triazol-1,4-diyl | —CH₂— | 2-Chloro-6-fluoro-phenyl | 559 |

TABLE 1-continued

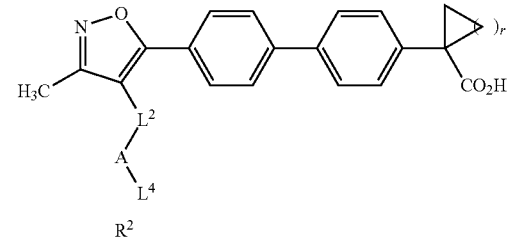

| Cmpd No | r | L² | A | L⁴ | R² | M + H* |
|---|---|---|---|---|---|---|
| 37 | 1 | —CH(OH)— | 1H-[1,2,3]Triazol-1,4-diyl | —CH₂— | 2,6-Dichloro-phenyl | 575 |
| 38 | 1 | —NH— | Pyridine-2,6-diyl | —CH₂— | Phenyl | 502 |
| 39 | 1 | —NH— | Phenyl-1,3-diyl | — | Phenyl | 487 |
| 40 | 1 | —NH— | Phenyl-1,4-diyl | — | Phenyl | 487 |
| 41 | 1 | —NH— | Pyridine-2,6-diyl | — | 3-Trifluoromethyl-phenyl | 556 |
| 42 | 1 | —NH— | Pyrazine-2,6-diyl | — | Phenyl | 489 |
| 43 | 1 | —NH— | [1,3,4]Oxadiazol-2,5-diyl | — | Phenyl | 479 |
| 44 | 1 | —NH— | [1,3,4]Oxadiazol-2,5-diyl | —CH₂— | Phenyl | 493 |
| 45 | 1 | —NH— | Pyridine-2,6-diyl | —CH₂— | 2-Fluoro-phenyl | 520 |
| 46 | 1 | —NH— | Pyridine-2,6-diyl | —CH₂— | 3-Fluoro-phenyl | 520 |
| 47 | 1 | —NH— | Pyridine-2,6-diyl | —CH₂— | 4-Fluoro-phenyl | 520 |
| 48 | 1 | —NH— | Pyridine-2,6-diyl | — | 3-Methoxy-phenyl | 518 |
| 49 | 1 | —NH— | Phenyl-1,3-diyl | —CH₂— | Phenyl | 501 |
| 50 | 1 | —NH— | Pyridine-2,6-diyl | — | 2-Cyano-phenyl | 513 |
| 51 | 1 | —NH— | Pyridine-2,6-diyl | — | 4-Methoxy-phenyl | 518 |
| 52 | 1 | —NH— | Pyridine-2,6-diyl | — | 3-Fluoro-phenyl | 506 |
| 53 | 1 | —NH— | Pyridine-2,6-diyl | — | 2-Methoxy-phenyl | 518 |
| 54 | 1 | —NH— | Pyridine-2,6-diyl | — | 2-Fluoro-phenyl | 506 |
| 55 | 1 | —NH— | Pyridine-2,6-diyl | — | 2-Trifluoromethyl-phenyl | 556 |
| 56 | 1 | —NHCH₂— | 1,3-Thiazole-2,5-diyl | — | Phenyl | 508 |
| 57 | 1 | —NH— | Phenyl-1,3-diyl | — | 2-Trifluoromethyl-phenyl | 555 |
| 58 | 1 | —NH— | Pyridine-3,5-diyl | — | Phenyl | 488 |
| 59 | 1 | —NH— | Pyridine-3,5-diyl | — | 3-Fluoro-phenyl | 506 |
| 60 | 1 | —NH— | Pyridine-2,6-diyl | — | 2-Chloro-phenyl | 522 |
| 61 | 1 | —CH(OH)— | Pyridine-2,6-diyl | — | Phenyl | 503 |
| 62 | 1 | —NH— | Pyridine-2,4-diyl | — | Phenyl | 488 |
| 63 | 1 | —NH— | Pyridine-2,4-diyl | — | 3-Fluoro-phenyl | 506 |
| 64 | 1 | —NH— | Pyridine-3,5-diyl | — | 2-Chloro-phenyl | 522 |
| 65 | 1 | —NH— | Pyridine-2,4-diyl | — | 2-Chloro-phenyl | 522 |
| 66 | 1 | —NH— | Pyrimidine-2,6-diyl | — | Phenyl | 489 |
| 67 | 1 | —NH— | Pyridine-2,4-diyl | — | Phenyl | 488 |
| 68 | 1 | —NH— | Pyridine-3,5-diyl | — | 3-Trifluoromethyl-phenyl | |
| 69 | 1 | —NH— | Pyridine-3,5-diyl | — | 4-Trifluoromethyl-phenyl | 556 |
| 70 | 2 | —NH— | Pyridine-2,6-diyl | — | Phenyl | 502 |
| 71 | 1 | —CH(OH)— | Pyridine-3,5-diyl | — | Phenyl | 503 |
| 72 | 1 | —CH(OH)— | Pyridine-3,5-diyl | — | 3-Trifluoromethyl-phenyl | 571 |
| 73 | 1 | —NH— | Pyridine-2,6-diyl | —C≡C— | Phenyl | 512 |
| 74 | 1 | —NH— | Pyridine-2,6-diyl | — | 3-Cyano-phenyl | 513 |
| 75 | 1 | —NH— | Pyridine-2,6-diyl | — | 5-Fluoro-2-methoxy-phenyl | 536 |
| 76 | 1 | —NH— | Pyridine-2,6-diyl | — | 3-Chloro-5-fluoro-phenyl | 540 |
| 77 | 1 | —NH— | Pyridine-2,6-diyl | — | 2,5-Difluoro-phenyl | 524 |
| 78 | 1 | —NH— | Pyridine-2,6-diyl | — | 2,6-Difluoro-phenyl | 556 |
| 79 | 1 | —NH— | Pyridine-2,6-diyl | — | 2-Chloro-5-fluoro-phenyl | 540 |

TABLE 1-continued

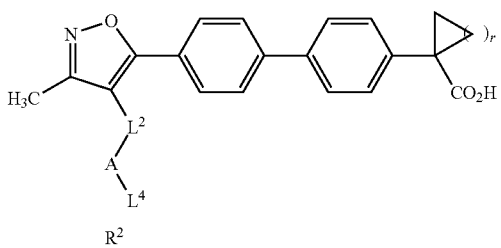

| Cmpd No | r | L² | A | L⁴ | R² | M + H* |
|---|---|---|---|---|---|---|
| 80 | 1 | —NH— | Pyridine-2,6-diyl | — | 2,3-Difluoro-phenyl | 524 |
| 81 | 1 | —NH— | Pyridine-2,6-diyl | — | 2-Chloro-3-fluoro-phenyl | 540 |
| 82 | 1 | —NH— | Pyridine-3,5-diyl | — | 2-Chloro-3-fluoro-phenyl | 540 |
| 83 | 1 | —NH— | Pyridine-2,6-diyl | — | 3-Fluoro-2-methyl-phenyl | 520 |
| 84 | 1 | —NH— | Pyridine-2,6-diyl | — | 2-Chloro-3-trifluoromethyl-phenyl | 590 |
| 85 | 1 | —NH— | Phenyl-1,3-diyl | — | 2-(Dimethylamino)-methyl-phenyl | 544 |
| 86 | 1 | —NH— | Pyridine-2,6-diyl | — | 2,3-Dichloro-phenyl | 556 |
| 87 | 1 | —NH— | Pyridine-2,6-diyl | — | 3-Fluoro-2-methoxy-phenyl | 536 |
| 88 | 1 | —NH— | Pyridine-3,5-diyl | — | 3-Chloro-phenyl | 522 |
| 89 | 1 | —NH— | Pyridine-3,5-diyl | — | 2,5-Difluoro-phenyl | 524 |
| 90 | 1 | —NH— | Pyridine-2,6-diyl | — | 3-Chloro-phenyl | 522 |

*mass spectrometric data

TABLE 2

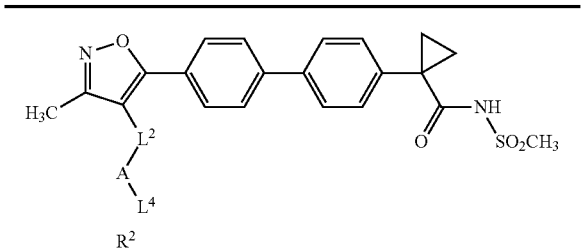

| Cmpd No | L² | A | L⁴ | R² | M + H* |
|---|---|---|---|---|---|
| 91 | —CH(OH)— | [1,2,3]Triazol-1,4-diyl | —CH₂— | Phenyl | 584 |
| 92 | —CH(OH)— | [1,3,4]Oxadiazol-2,5-diyl | —CH₂— | Phenyl | 585 |
| 93 | —CH(OH)— | [1,2,3]Triazol-1,4-diyl | —CH₂— | 3-Trifluoromethyl-phenyl | 652 |
| 94 | —NH— | [1,3,4]Oxadiazol-2,5-diyl | — | Phenyl | 556 |
| 95 | —NH— | Pyridine-2,6-diyl | —CH₂— | Phenyl | 579 |
| 96 | —NH— | Pyridine-2,6-diyl | — | Phenyl | 565 |

*mass spectrometric data

TABLE 3

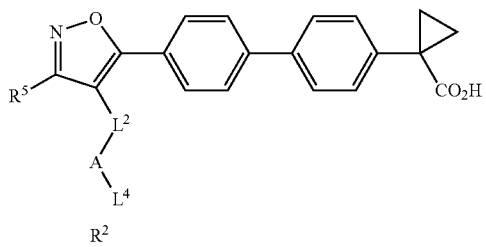

| Cmpd No | L² | A | L⁴ | R² | R⁵ | M + H* |
|---|---|---|---|---|---|---|
| 97 | —NH— | Pyridine-2,6-diyl | — | Phenyl | —CH₂CH₃ | 502 |
| 98 | —NH— | [1,3,4]Oxadiazol-2,5-diyl | — | Phenyl | —CH₂CH₃ | 493 |

*mass spectrometric data

Synthesis of Compounds

Compounds of Formula (I) described herein are synthesized using standard synthetic techniques or using methods known in the art in combination with methods described herein. In additions, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, *Advanced Organic*

Chemistry, 4th Edition, Wiley (1992); Carey et al., *Advanced Organic Chemistry*, 4th Edition, Vols. A and B, Plenum (2000, 2001), and Greene et al., *Protective Groups in Organic Synthesis*, 3rd Edition, Wiley (1999). General methods for the preparation of compounds can be modified by the use of appropriate reagents and conditions for the introduction of the various moieties found in the formulae as provided herein.

In some embodiments, the synthesis of compounds of Formula (I) begins with the synthetic steps outlined in Scheme 1.

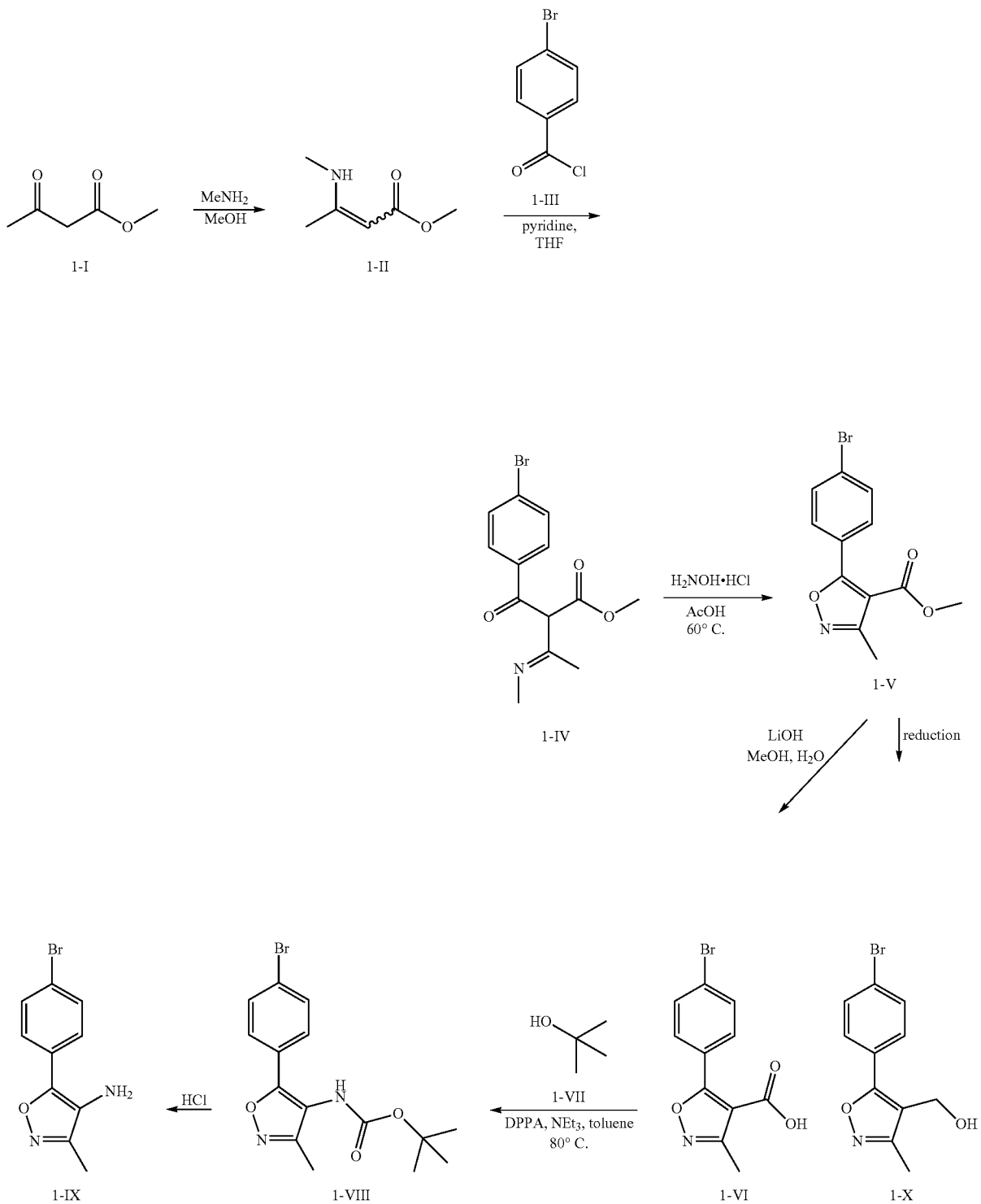

In one aspect, the synthesis of compounds of Formula (I) described herein begins with the reaction of an alkyl acetoacetate with methylamine to provide a compound of structure 1-II. Compounds of structure 1-II are reacted with a substituted or unsubstituted 4-halo-benzoyl chloride (structure 1-III) to provide compounds of structure 1-IV. Treatment of compounds of structure 1-IV with hydroxylamine and acetic acid provides isoxazoles of structure 1-V. Hydrolysis of the ester group of isoxazoles of structure 1-V provides carboxylic acids of structure 1-VI. A Curtius rearrangement of carboxylic acids of structure 1-VI in the presence of hydroxy compounds of structure 1-VII provides carbamate compounds of structure 1-VIII. Deprotection of the tert-butoxycarbonyl group provides amines of structure 1-IX which are further functionalized into compounds of Formula (I). In some embodiments, compounds of 1-V are reduced to the alcohol and then further functionalized into compounds of Formula (I).

In some embodiments, compounds are prepared as outlined in Scheme 2.

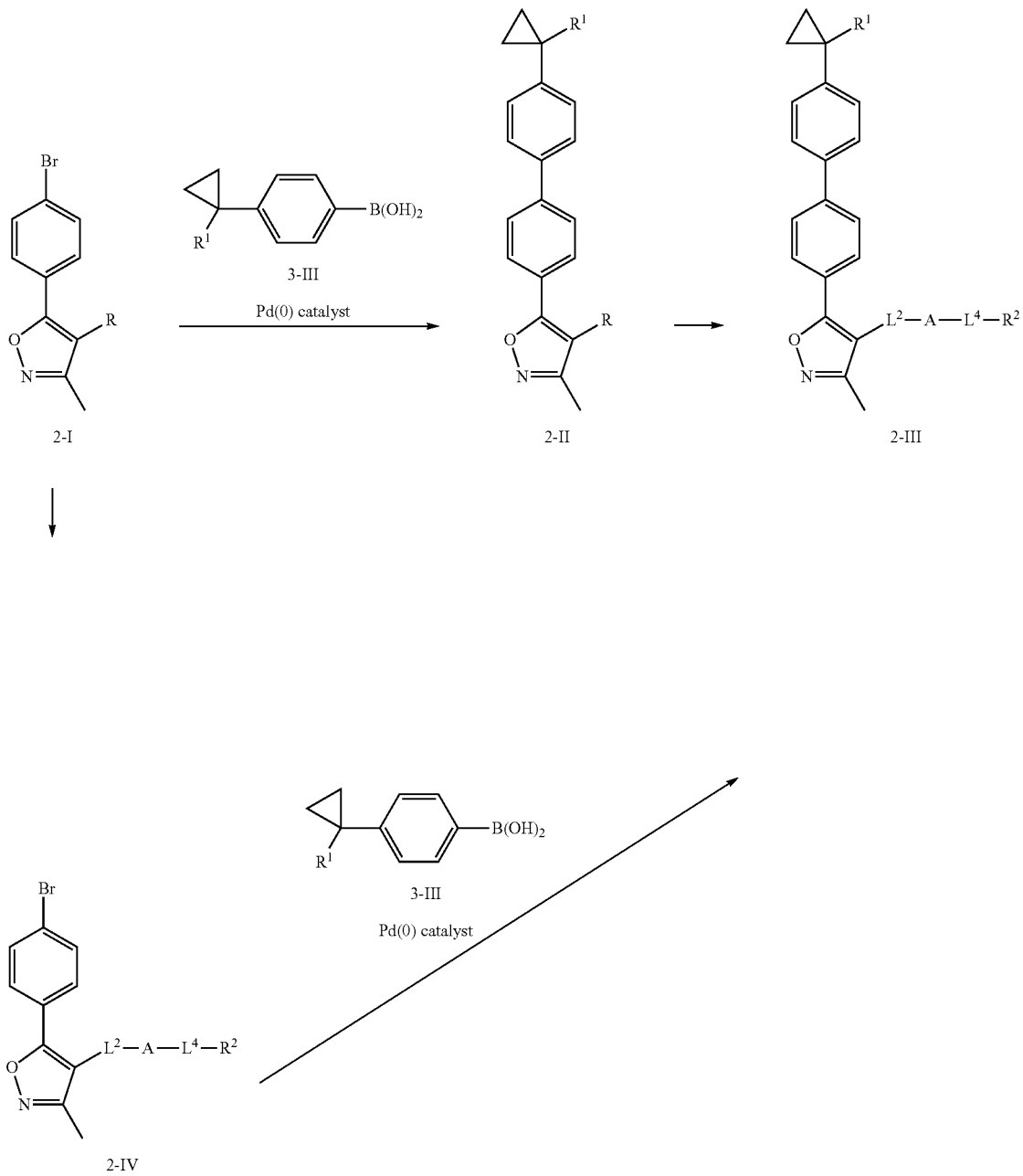

In some embodiments, compounds of structure 2-I are subjected to a palladium-catalyzed coupling with boronic acid derivatives 3-III to provide compounds of structure 2-II. In some embodiments, R is —NH$_2$, —NHCO$_2$alkyl, —CO$_2$alkyl, —CH$_2$OH, —CH$_2$CN, —CH$_2$Br, —C(=O)H, —CH$_2$N3, —CO$_2$NHNH$_2$, —CH$_2$CO$_2$NHNH$_2$ or any other suitable group that can be transformed to provide L$^2$ as described herein. Compounds of structure 2-II are then utilized to provide compounds of structure 2-III. Alternatively, compounds of structure 2-I are derivatized to provide compounds of structure 2-IV, which are subsequently coupled with compound 3-III to provide compounds of structure 2-III. R$^2$ in Scheme 2 is a substituted or unsubstituted phenyl.

Suitable reactions for transforming 2-1 to 2-IV or 2-II to 2-III include, but are not limited to, nucleophilic displacement reactions (where R includes a suitable leaving group), organometallic chemical reactions, reductive amination reactions, cycloaddition reactions (e.g., Huisgen-Sharpless cycloaddition), and the like.

In some embodiments, compounds of Formula (I) are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene et al., *Protective Groups in Organic Synthesis*, 3rd Edition, John Wiley & Sons, New York, N.Y. (1999), and Kocienski, *Protective Groups*, Thieme Verlag, New York, N.Y. (1994), which are incorporated herein by reference for such disclosure.

Further Forms of Compounds

In one aspect, compounds of Formula (I) possess one or more stereocenters and each stereocenter exists independently in either the R or S configuration. The compounds presented herein include all diastereomeric, and enantiomeric forms. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), amorphous phases, and/or pharmaceutically acceptable salts of compounds having the structure of Formula (I), as well as metabolites and active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In some embodiments, sites on the aromatic ring portion of compounds of Formula (I) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a deuterium, a halogen, or an alkyl group.

In another embodiment, the compounds described herein are labeled isotopically or by another other means, including, but not limited to, the use of chromophores or fluorescent moieties, bioluminescent labels, or chemiluminescent labels.

In one aspect, substitution with isotopes such as deuterium affords certain therapeutic advantages resulting from greater metabolic stability, such as, for example, increased in vivo half-life or reduced dosage requirements.

"Pharmaceutically acceptable", as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

In some embodiments, pharmaceutically acceptable salts are obtained by reacting a compound of Formula (I) with acids. Pharmaceutically acceptable salts are also obtained by reacting a compound of Formula (I) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid (e.g., hydrochloric acid, hydrobromic acid, sulfuric acid, phosphoric acid, and the like); or with an organic acid (e.g., acetic acid, propionic acid, glycolic acid, pyruvic acid, lactic acid, malonic acid, succinic acid, malic acid, maleic acid, fumaric acid, trifluoroacetic acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, salicylic acid, stearic acid, muconic acid, butyric acid, phenylacetic acid, phenylbutyric acid, valproic acid, and the like); (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, a sodium salt of the compound of Formula (I) is prepared.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Compounds described herein, such as compounds of Formula (I), may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound.

Certain Terminology

Unless otherwise stated, the following terms used in this application, including the specification and claims, have the definitions given below. It must be noted that, as used in the specification and the appended claims, the singular forms "a", "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes", and "included", is not limiting. The section headings used herein are for organizational purposes only and are not to be construed as limiting the subject matter described.

An "alkyl" refers to an aliphatic hydrocarbon. The alkyl may be saturated or unsaturated. The alkyl, whether saturated or unsaturated, is a branched alkyl or straight chain alkyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like.

The term "alkylene" refers to a divalent alkyl radical. Any of the above mentioned monovalent alkyl groups may be an alkylene by abstraction of a second hydrogen atom from the alkyl. In one aspect, an alkelene is a $C_1$-$C_6$alkylene. In another aspect, an alkylene is a $C_1$-$C_4$alkylene. Typical alkylene groups include, but are not limited to, methylene, ethylene, propylene and butylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

An "alkoxy" group refers to a (alkyl)O— group, where alkyl is as defined herein.

"Cycloalkyl" refers to cyclopropyl, cyclopropenyl, cyclobutyl, cyclobutenyl, cyclopentyl, cyclopentenyl, cyclohexyl, or cyclohexenyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom.

The term "heteroalkyl" refers to an alkyl group in which one or more skeletal atoms of the alkyl are selected from an atom other than carbon, e.g., oxygen, nitrogen (e.g., NH or Nalkyl), sulfur, or combinations thereof. In some embodiments, one aspect, heteroalkyl refers to an alkyl group in which one of the skeletal atoms of the alkyl is oxygen. In some embodiments, one aspect, heteroalkyl refers to an alkyl group in which one of the skeletal atoms of the alkyl is NH or Nalkyl.

The term "heteroalkylene" refers to an alkylene group in which one or more skeletal atoms of the alkyl are selected from an atom other than carbon, e.g., oxygen, nitrogen (e.g., NH or Nalkyl), sulfur, or combinations thereof. In one aspect, a heteroalkylene is a $C_1$-$C_6$heteroalkylene. In another aspect, a heteroalkylene is a $C_1$-$C_4$heteroalkylene. Exemplary heteroalkylenes include, but are not limited to, —$OCH_2$—, —$OCH(CH_3)$—, —$OC(CH_3)_2$—, —$OCH_2CH_2$—, —$CH_2O$—, —$CH(CH_3)O$—, —$C(CH_3)_{2-O}$—, —$CH_2CH_2O$—, —$CH_2OCH_2$—, —$CH_2OCH_2CH_2$—, —$CH_2CH_2OCH_2$—, —$SCH_2$—, —$SCH(CH_3)$—, —$SC(CH_3)_2$—, —$SCH_2CH_2$—, —$CH_2S$—, —$CH(CH_3)S$—, —$C(CH_3)_2S$—, —$CH_2CH_2S$—, —$CH_2SCH_2$—, —$CH_2SCH_2CH_2$—, —$CH_2CH_2SCH_2$—, —$SO_2CH_2$—, —$SO_2CH(CH_3)$—, —$SO_2C(CH_3)_2$—, —$SO_2CH_2CH_2$—, —$CH_2SO_2$—, —$CH(CH_3)SO_2$—, —$C(CH_3)_2SO_2$—, —$CH_2CH_2SO_2$—, —$CH_2SO_2CH_2$—, —$CH_2SO_2CH_2CH_2$—, —$CH_2CH_2SO_2CH_2$—, —$NHCH_2$—, —$NHCH(CH_3)$—, —$NHC(CH_3)_2$—, —$NHCH_2CH_2$—, —$CH_2NH$—, —$CH(CH_3)NH$—, —$C(CH_3)_2NH$—, —$CH_2CH_2NH$—, —$CH_2NHCH_2$—, —$CH_2NHCH_2CH_2$—, —$CH_2CH_2NHCH_2$—, and the like.

The terms "heteroaryl" or, alternatively, "heteroaromatic" refers to an aryl group that includes one or more ring heteroatoms selected from nitrogen, oxygen and sulfur. Monocyclic heteroaryls include, but are not limited to, furanyl, thienyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, or triazinyl. In one aspect, a heteroaryl contains 0-4 N atoms. In another aspect, a heteroaryl contains 1-3 N atoms. In another aspect, a heteroaryl contains 0-3 N atoms, 0-1 O atoms, and 0-1 S atoms. In one aspect, monocyclic heteroaryl is a $C_1$-$C_5$heteroaryl. In one aspect, monocyclic heteroaryl is a 5-membered or 6-membered heteroaryl. Depending on the structure, a heteroaryl group can be a monoradical or a diradical (i.e., a heteroarylene group).

The term "heteroarylene" refers to a divalent heteroaryl radical. Any of the above mentioned monovalent heteroaryl groups may be a heteroarylene by abstraction of a second hydrogen atom from the heteroaryl group. The divalent heteroaryl radical may be attached through two carbon atoms, or through one carbon atom and one heteroatom, or through two heteroatoms.

The term "optionally substituted" or "substituted" means that the referenced group may be substituted with one or more additional group(s) individually and independently selected from halogen, —CN, —$NH_2$, —OH, —$NH(CH_3)$, —$N(CH_3)_2$, alkyl, cycloalkyl, fluoroalkyl, heteroalkyl, alkoxy, fluoroalkoxy, —S-alkyl, or —$S(=O)_2$alkyl. In some embodiments, an optional substituent is selected from halogen, —CN, —$NH_2$, —OH, —$NH(CH_3)$, —$N(CH_3)_2$, —$CH_3$, —$CH_2CH_3$, —$CF_3$, —$CH_2CF_3$, —$OCH_3$, —$OCH_2CH_3$, —$OCF_3$ and —$OCH_2CF_3$. In some embodiments, substituted groups are substituted with one or two of the preceding groups. In some embodiments, substituted groups are substituted with one of the preceding groups.

The term "acceptable" with respect to a formulation, composition or ingredient, as used herein, means having no persistent detrimental effect on the general health of the subject being treated.

The term "modulate", as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator", as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist", as used herein, refers to a molecule such as a compound, a drug, an enzyme activator or a hormone modulator that binds to a specific receptor and triggers a response in the cell. An agonist mimics the action of an endogenous ligand (such as LPA, prostaglandin, hormone or neurotransmitter) that binds to the same receptor.

The term "antagonist", as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

The term "LPA-dependent", as used herein, refers to conditions or disorders that would not occur, or would not occur to the same extent, in the absence of LPA.

The term "LPA-mediated", as used herein, refers to refers to conditions or disorders that might occur in the absence of LPA but can occur in the presence of LPA.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount", as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans, chimpanzees, apes, monkey, cattle, horses, sheep, goats, swine, rabbits, dogs, cats, rodents, rats, mice guinea pigs, and the like. In one embodiment, the mammal is a human.

The terms "treat", "treating" or "treatment", as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations and Routes of Administration

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in *Remington: The Science and Practice of Pharmacy*, Nineteenth Edition, Mack Publishing Company, Easton, Pa. (1995); Hoover, J. E., *Remington's Pharmaceutical Sciences*, Mack Publishing Co., Easton, Pa. (1975); Liberman, H. A. et al., eds., *Pharmaceutical Dosage Forms*, Marcel Decker, New York, N.Y. (1980); and *Pharmaceutical Dosage Forms and Drug Delivery Systems*, Seventh Edition, Lippincott Williams & Wilkins (1999), herein incorporated by reference for such disclosure.

A pharmaceutical composition, as used herein, refers to a mixture of a compound of Formula (I) with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I) are administered orally.

In some embodiments, the compounds of Formula (I) are administered topically. In such embodiments, the compound of Formula (I) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I) are administered topically to the skin.

In another aspect, the compounds of Formula (I) are administered by inhalation.

In another aspect, the compounds of Formula (I) are formulated for intranasal administration. Such formulations include nasal sprays, nasal mists, and the like.

In another aspect, the compounds of Formula (I) are formulated as eye drops.

In any of the aforementioned aspects are further embodiments in which the effective amount of the compound of Formula (I) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I) is formulated for use as an aerosol, a mist or a powder.

For buccal or sublingual administration, the compositions may take the form of tablets, lozenges, or gels formulated in a conventional manner.

In some embodiments, compounds of Formula (I) are prepared as transdermal dosage forms.

In one aspect, a compound of Formula (I) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I) are used in the preparation of medicaments for the treatment of LPA-dependent or LPA-mediated diseases or conditions. In addition, a method for treating any of the diseases or conditions described herein in a subject in need of such treatment, involves administration of pharmaceutical compositions that include at least one compound of Formula (I) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Patient Selection

In any of the aforementioned aspects involving the prevention or treatment of LPA-mediated diseases or conditions are further embodiments comprising identifying patients by screening for LPA receptor gene SNPs. Patients can be further selected based on increased LPA receptor expression in the tissue of interest. LPA receptor expression are determined by methods including, but not limited to, northern blotting, western blotting, quantitative PCR (qPCR), flow cytometry, autoradiography (using a small molecule radioligand or PET ligand). In some embodiments, patients are selected based on the concentration of serum or tissue LPA measured by mass spectrometry. In some embodiments, patients are selected based on a combination of the above markers (increased LPA concentrations and increased LPA receptor expression).

Combination Treatments

In certain instances, it is appropriate to administer at least one compound of Formula (I) in combination with another therapeutic agent.

In one specific embodiment, a compound of Formula (I) is co-administered with a second therapeutic agent, wherein the compound of Formula (I) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In another embodiment described herein, methods for treatment of proliferative disorders, including cancer, comprises administration to a mammal a compound of Formula (I) in combination with one or more anti-cancer agents and/or radiation therapy.

In one aspect, compounds of Formula (I) are to treat or reduce fibrosis in a mammal. In one aspect, compounds of Formula (I) are administered in combination with one or more immunosuppressants. In some embodiments, a compound of Formula (I) is administered with corticosteroids.

In yet another embodiment described herein, methods for treating LPA-dependent or LPA-mediated conditions or diseases, such as the therapy of respiratory disorders (e.g., pulmonary fibrosis, asthma, COPD, rhinitis), comprises administration to a patient compounds, pharmaceutical compositions, or medicaments described herein in combination with at least one agent used in the treatment of respiratory conditions.

In some embodiments, compounds of Formula (I) are administered to a patient in combination with anti-inflammatory agents.

In one embodiment, compounds of Formula (I) are administered to a patient in combination with inhaled corticosteroids.

EXAMPLES

These Examples are provided for illustrative purposes only and not to limit the scope of the claims provided herein.

Example 1

Synthesis of 1-[4'-(4-Amino-3-methyl-isoxazol-5-yl)-biphenyl-4-yl]-cyclopropanecarboxylic acid ethyl ester Step 1: 3-Methylamino-but-2-enoic acid methyl ester: To a solution of methyl acetoacetate (29.4 g, 253 mmol) in MeOH (30 mL) was added methylamine (33 wt % in EtOH; 48 mL, 385 mmol) dropwise at room temperature. The reaction was stirred for 1 hour, and then concentrated and dried to give the title compound as a white crystalline solid.

Step 2: 2-(4-Bromo-benzoyl)-3-oxo-butyric acid methyl ester: To 3-methylamino-but-2-enoic acid methyl ester (5.0 g, 39.1 mmol) in THF (100 mL) was added pyridine (3.7 mL, 47 mmol). The mixture was cooled to 0° C., and 4-bromobenzoyl chloride (8.55 g, 39.1 mmol) in THF (30 mL) was added dropwise over 2 minutes. The reaction was warmed to room temperature over 1 hour and stirred overnight. Aqueous workup provided the title compound.

Step 3: 5-(4-Bromo-phenyl)-3-methyl-isoxazole-4-carboxylic acid methyl ester: To a mixture of 2-(4-bromo-benzoyl)-3-oxo-butyric acid methyl ester (11 g, 39 mmol) in acetic acid (50 mL) was added hydroxylamine hydrochloride (2.66 g, 39 mmol), and the reaction was stirred at 115° C. for 1 hour. After cooling, aqueous workup provided the title compound, which was used directly in the hydrolysis step.

Step 4: 5-(4-Bromo-phenyl)-3-methyl-isoxazole-4-carboxylic acid: 5-(4-Bromo-phenyl)-3-methyl-isoxazole-4-carboxylic acid methyl ester (39 mmol) in MeOH (50 mL) and $H_2O$ (10 mL) was treated with lithium hydroxide (2 g, 48 mmol), and the reaction was stirred at 60° C. for 1 hour. The mixture was acidified, and standard workup provided the title compound.

Step 5: [5-(4-Bromo-phenyl)-3-methyl-isoxazol-4-yl]-carbamic acid tert-butyl ester: 5-(4-Bromo-phenyl)-3-methyl-isoxazole-4-carboxylic acid (1.6 g, 6.0 mmol), diphenylphosphoryl azide (1.6 g, 6.0 mmol), and triethylamine (1.3 mL, 9.3 mmol) were combined in t-BuOH and refluxed overnight. After cooling, the mixture was concentrated, and the residue was partitioned between EtOAc and $H_2O$. The organic layer was separated and concentrated, and the residue was purified by silica gel chromatography (16-18% EtOAc in hexanes) to give the title compound.

Step 6: 1-(4-Bromo-phenyl)-cyclopropanecarbonitrile: Potassium hydroxide (14.3 g, 255 mmol) was dissolved in $H_2O$ (5 mL) and toluene (40 mL). 4-Bromophenylacetonitrile (5.0 g, 25.5 mmol) and tetrabutylammonium bromide (0.41 g, 1.3 mmol) was added, followed by 1,2-dibromoethane (3.25 mL, 38 mmol) dropwise over 10 minutes. The reaction was stirred at room temperature for 2 hours and then worked-up to give the title compound.

Step 7: 1-(4-Bromo-phenyl)-cyclopropanecarboxylic acid: 1-(4-Bromo-phenyl)-cyclopropanecarbonitrile (5 g, 22.5 mmol) and potassium hydroxide (5 g, 89.3 mmol) were combined in ethylene glycol (70 mL), and the reaction was stirred at 180° C. for 4 hours. The mixture was poured into $H_2O$, acidified, and filtered to give the title compound.

Step 8: 1-(4-Bromo-phenyl)-cyclopropanecarboxylic acid ethyl ester: 1-(4-Bromo-phenyl)-cyclopropanecarboxylic acid (5 g, 20.7 mmol) in EtOH (50 mL) was treated with sulfuric acid (2 mL), and the reaction was stirred at 75° C. for 1 hour. The mixture was worked up to give the title compound.

Step 9: 1-[4-(4,4,5,5-Tetramethyl-[1,3,2]dioxaborolan-2-yl)-phenyl]-cyclopropanecarboxylic acid ethyl ester: 1-(4-Bromo-phenyl)-cyclopropanecarboxylic acid ethyl ester (3.6 g, 13.4 mmol), bis(pinacolato)diboron (3.37 g, 16.1 mmol), and potassium acetate (2.8 g, 29.0 mmol) were combined in 1,4-dioxane (30 mL) under $N_2$ atmosphere. The solution was purged with $N_2$ (g) for 10 minutes, and then (1,1'-bis(diphenylphosphino)ferrocene)-dichloropalladium (II) (0.50 g, 0.65 mmol) was added and the reaction was heated to 80° C. for 2 hours. After aqueous workup, the crude material was purified by silica gel chromatography (0-30% EtOAc in hexanes) to give the title compound.

Step 10: 1-[4'-(4-tert-Butoxycarbonylamino-3-methyl-isoxazol-5-yl)-biphenyl-4-yl]-cyclopropanecarboxylic acid ethyl ester: [5-(4-Bromo-phenyl)-3-methyl-isoxazol-4-yl]-carbamic acid tert-butyl ester (2.0 g, 5.6 mmol), 1-[4-(4,4,5,5-tetramethyl-[1,3,2]dioxaborolan-2-yl)-phenyl]-cyclopropanecarboxylic acid ethyl ester (1.78 g, 5.6 mmol), tetrakis(triphenylphosphine)palladium(0) (0.65 g, 0.56 mmol), and sodium bicarbonate (1.4 g, 16.8 mmol) were combined in DME (30 mL) and $H_2O$ (10 mL), and the mixture was purged with $N_2$ (g). The reaction was stirred at 80° C. overnight, and after aqueous workup, the crude material was purified by silica gel chromatography (0-40% EtOAc in hexanes) to give the title compound.

Step 11: 1-[4'-(4-Amino-3-methyl-isoxazol-5-yl)-biphenyl-4-yl]-cyclopropanecarboxylic acid ethyl ester: 1-[4'-(4-tert-Butoxycarbonylamino-3-methyl-isoxazol-5-yl)-biphenyl-4-yl]-cyclopropanecarboxylic acid ethyl ester (1.5 g, 3.2 mmol) in $CH_2Cl_2$ (10 mL) was treated with trifluoroacetic acid (4 mL), and the reaction was stirred for 1 hour. The mixture was neutralized and worked up to give the title compound.

Example 2

Reductive Amination Procedure

Amine containing compound (1 equivalent) and ketone compound or aldehyde compound (1-1.5 equivalents) were combined in toluene and stirred at 110° C. for 1 hour. After cooling to room temperature, THF was added, followed by excess sodium cyanoborohydride (2-3 equivalents), and the reaction was stirred at room temperature for 2 hours to overnight. The mixture was purified by silica gel chromatography.

Example 3

Hydrolysis of Alkyl Esters

To cyclopropanecarboxylic acid ethyl ester compound (1 equivalent) in ~2:1:1 $THF:H_2O:MeOH$ was added lithium hydroxide (3-10 equivalents), and the reaction was stirred at 70° C. for 2 hours to overnight. After acidic workup, the crude material was purified by preparative HPLC.

Example 4

Suzuki Coupling Reaction

A 4-substituted-5-(4-bromo-phenyl)-3-methyl-isoxazole (1 equivalent), 1-[4-(4,4,5,5-tetramethyl-[1,3,2]dioxaborolan-2-yl)-phenyl]-cyclopropanecarboxylic acid ethyl ester (1.2-2.0 equivalents), tetrakis(triphenylphosphine)palladium(0) (~0.05-0.15 equivalents), and sodium bicarbonate (~2.5 equivalents) were combined in ~3:1 $DME:H_2O$, and the mixture was purged with $N_2$ (g). The reaction was stirred at 60-80° C. for at least 1 hour to overnight and then cooled and concentrated. The crude material was purified by silica gel chromatography (0-40% EtOAc in hexanes).

Example 5

Synthesis of [5-(4-Bromo-phenyl)-3-methyl-isoxazol-4-yl]-methanol and 5-(4-Bromo-phenyl)-3-methyl-isoxazole-4-carbaldehyde Step 1: [5-(4-Bromo-phenyl)-3-methyl-isoxazol-4-yl]-methanol: 5-(4-Bromo-phenyl)-3-methyl-isoxazole-4-carboxylic acid methyl ester (5 g, 16.8 mmol) and lithium borohydride (1.85 g, 84.1 mmol) were combined in EtOH and stirred at 60° C. After aqueous workup, the crude material was purified by silica gel chromatography to give the title compound.

Step 2: 5-(4-Bromo-phenyl)-3-methyl-isoxazole-4-carbaldehyde: [5-(4-Bromo-phenyl)-3-methyl-isoxazol-4-yl]-methanol (1.2 g, 4.5 mmol) was treated with 4-methylmorpholine N-oxide (0.786 g, 6.7 mmol) and tetrapropylammonium perruthenate (catalytic) in $CH_2Cl_2$. The reaction was monitored by analytical LCMS and when complete it was filtered through CELITE® then submitted to silica gel chromatography to give the title compound.

Example 6

Synthesis of 1-{4'-[3-Methyl-4-(3-phenyl-pyrazol-1-ylmethyl)-isoxazol-5-yl]-biphenyl-4-yl}-cyclopropanecarboxylic acid (Compound 1)

Step 1: 1-[4'-(4-Hydroxymethyl-3-methyl-isoxazol-5-yl)-biphenyl-4-yl]-cyclopropanecarboxylic acid ethyl ester: Prepared according to the procedure described in Example 4, using [5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 2: 1-[4'-(4-Bromomethyl-3-methyl-isoxazol-5-yl)-biphenyl-4-yl]-cyclopropanecarboxylic acid ethyl ester: Phosphorus tribromide (0.43 mL, 4.53 mmol) was added to a solution of 1-[4'-(4-hydroxymethyl-3-methyl-isoxazol-5-yl)-biphenyl-4-yl]-cyclopropanecarboxylic acid ethyl ester (1.14 g, 3.02 mmol) in DME (30 mL) at 0° C. The reaction was stirred overnight at room temperature, and then cooled to 0° C. and neutralized with saturated aqueous $NaHCO_3$ to pH 7. The mixture was partitioned between $CH_2Cl_2$ and $H_2O$, and the aqueous layer was extracted with $CH_2Cl_2$. The combined organic layers were dried over $MgSO_4$, filtered, and concentrated, and the residue was purified by silica gel chromatography to give the title compound.

Step 3: 1-{4'-[3-Methyl-4-(3-phenyl-pyrazol-1-ylmethyl)-isoxazol-5-yl]-biphenyl-4-yl}-cyclopropanecarboxylic acid: 1-[4'-(4-Bromomethyl-3-methyl-isoxazol-5-yl)-biphenyl-4-yl]-cyclopropanecarboxylic acid ethyl ester (0.132 g, 0.3 mmol) and 3-phenyl-1H-pyrazole (0.043 g, 0.3 mmol) were combined in DMF. Sodium hydride (60% in mineral oil; 0.014 g, 0.35 mmol) was added, and the reaction was stirred at room temperature for 1.5 hours. Once no starting material was seen by analytical LCMS, the mixture was diluted with EtOAc and 1N aqueous HCl. The aqueous layer was extracted with EtOAc, and the combined organic layers were washed with $H_2O$ and brine, and then dried over $Na_2SO_4$, filtered, and concentrated. The residue was purified by preparative HPLC to give the title compound.

Example 7

Synthesis of 1-{4'-[3-Methyl-4-(4-phenyl-[1,2,3]triazol-1-ylmethyl)-isoxazol-5-yl]-biphenyl-4-yl}-cyclopropanecarboxylic acid (Compound 2)

Step 1: 1-{4'-[3-Methyl-4-(4-phenyl-[1,2,3]triazol-1-ylmethyl)-isoxazol-5-yl]-biphenyl-4-yl}-cyclopropanecarboxylic acid ethyl ester: Prepared according to the procedure described in Example 6, Step 3, using 1-[4'-(4-bromomethyl-3-methyl-isoxazol-5-yl)-biphenyl-4-yl]-cyclopropanecarboxylic acid ethyl ester and 4-phenyl-1H-1,2,3-triazole.

Step 2: The ester from Step 1 was hydrolyzed to the acid according to the procedure described in Example 3.

Example 8

Synthesis of 1-{4'-[3-Methyl-4-(5-phenyl-[1,3,4]oxadiazol-2-ylmethyl)-isoxazol-5-yl]-biphenyl-4-yl}-cyclopropanecarboxylic acid (Compound 3)

Step 1: 4-Bromomethyl-5-(4-bromo-phenyl)-3-methyl-isoxazole: [5-(4-Bromo-phenyl)-3-methyl-isoxazol-4-yl]-methanol (2.88 g, 10.74 mmol) in DME (23 mL) was treated with phosphorus tribromide (1.5 mL, 16.11 mmol), and the reaction was stirred at room temperature for 1 hour. Aqueous workup provided the title compound.

Step 2: [5-(4-Bromo-phenyl)-3-methyl-isoxazol-4-yl]-acetonitrile: To 4-bromomethyl-5-(4-bromo-phenyl)-3-methyl-isoxazole (10.74 mmol) in DMF (30 mL) was added potassium cyanide (0.729 g, 10.74 mmol), and the reaction was stirred at 65° C. overnight. After aqueous workup, the crude material was purified by silica gel chromatography (0-70% EtOAc in hexanes) to give the title compound.

Step 3: [5-(4-Bromo-phenyl)-3-methyl-isoxazol-4-yl]-acetic acid: [5-(4-Bromo-phenyl)-3-methyl-isoxazol-4-yl]-acetonitrile (1.652 g, 5.96 mmol) in EtOH (9 mL) was treated with 4N aqueous NaOH (6 mL, 23.85 mmol), and the reaction was stirred at 75° C. for 3 hours. The mixture was acidified with 2N aqueous HCl (12 mL) and a precipitate formed as the solution cooled to room temperature. The mixture was filtered, and the solid material was dried to give the title compound.

Step 4: [5-(4-Bromo-phenyl)-3-methyl-isoxazol-4-yl]-acetic acid ethyl ester: To [5-(4-bromo-phenyl)-3-methyl-isoxazol-4-yl]-acetic acid (0.200 g, 0.68 mmol) in EtOH (3 mL) was added thionyl chloride (0.10 mL, 1.35 mmol), and the reaction was stirred for 1 hour. The mixture was quenched with saturated aqueous $NH_4Cl$ and diluted with EtOAc and $H_2O$. After standard aqueous workup, the crude material was purified by silica gel chromatography to give the title compound.

Step 5: [5-(4-Bromo-phenyl)-3-methyl-isoxazol-4-yl]-acetic acid hydrazide: To [5-(4-bromo-phenyl)-3-methyl-isoxazol-4-yl]-acetic acid ethyl ester (0.114 g, 0.37 mmol) in EtOH (4 mL) was added hydrazine (1M in THF; 2 mL), and the reaction was sealed and stirred at 80° C. overnight. The mixture was poured into brine and extracted with EtOAc. The combined organic layers were washed with $H_2O$ and brine, and then dried over $MgSO_4$, filtered, and concentrated to give the title compound.

Step 6: 2-[5-(4-Bromo-phenyl)-3-methyl-isoxazol-4-ylmethyl]-5-phenyl-[1,3,4]oxadiazole: To [5-(4-bromo-phenyl)-3-methyl-isoxazol-4-yl]-acetic acid hydrazide (0.142 g, 0.46 mmol) in $CH_2Cl_2$ (2.3 mL) at 0° C. was added triethylamine (0.19 mL, 1.37 mmol) and benzoyl chloride (0.05 mL, 0.46 mmol), and the reaction was stirred at room temperature for 3 hours. Toluenesulfonyl chloride (0.088 g, 0.46 mmol) was added, and the reaction was stirred overnight. After aqueous workup, the crude material was purified by silica gel chromatography to give the title compound.

Step 7: Synthesis of 1-{4'-[3-Methyl-4-(5-phenyl-[1,3,4]oxadiazol-2-ylmethyl)-isoxazol-5-yl]-biphenyl-4-yl}-cyclopropanecarboxylic acid ethyl ester: Prepared according to the procedure described in Example 4, using 2-[5-(4-bromo-phenyl)-3-methyl-isoxazol-4-ylmethyl]-5-phenyl-[1,3,4]oxadiazole and 1-[4-(4,4,5,5-tetramethyl-[1,3,2]dioxaborolan-2-yl)-phenyl]-cyclopropanecarboxylic acid ethyl ester.

Step 8: The ester from Step 7 was hydrolyzed to the acid according to the procedure described in Example 3.

Example 9

Synthesis of 1-{4'-[4-(4-Benzyl-[1,2,3]triazol-1-ylmethyl)-3-methyl-isoxazol-5-yl]-biphenyl-4-yl}-cyclopropanecarboxylic acid (Compound 4)

Step 1: 1-[4'-(4-Azidomethyl-3-methyl-isoxazol-5-yl)-biphenyl-4-yl]-cyclopropanecarboxylic acid ethyl ester: Sodium nitrile (0.060 g, 0.91 mmol) was dissolved in $H_2O$ (0.5 mL). DMF (2 mL) was added, followed by 1-[4'-(4-Bromomethyl-3-methyl-isoxazol-5-yl)-biphenyl-4-yl]-cyclopropanecarboxylic acid ethyl ester (0.200 g, 0.45 mmol), and the reaction was stirred overnight. The mixture was diluted with $H_2O$ and extracted with EtOAc. The combined organic layers were dried over $Na_2SO_4$, filtered, and concentrated to give the title compound.

Step 2: 1-{4'-[4-(4-Benzyl-[1,2,3]triazol-1-ylmethyl)-3-methyl-isoxazol-5-yl]-biphenyl-4-yl}-cyclopropanecarboxylic acid ethyl ester: To a solution of 1-[4'-(4-azidomethyl-3-methyl-isoxazol-5-yl)-biphenyl-4-yl]-cyclopropanecarboxylic acid ethyl ester (0.183 g, 0.45 mmol) in tBuOH (1.5 mL) and $H_2O$ (1.5 mL) was added 3-phenyl-1-propyne (0.053 g, 0.45 mmol), followed by sodium ascorbate (0.009 g, 0.045 mmol) and copper(II) sulfate pentahydrate (0.001 g, 0.005 mmol), and the reaction was stirred overnight. After aqueous workup, the crude material was purified by silica gel chromatography to give the title compound.

Step 3: The ester from Step 2 was hydrolyzed to the acid according to the procedure described in Example 3.

Example 10

Synthesis of 1-(4'-{4-[3-(4-Bromo-phenyl)-pyrazol-1-ylmethyl]-3-methyl-isoxazol-5-yl}-biphenyl-4-yl)-cyclopropanecarboxylic acid (Compound 5)

Step 1: 1-(4'-{4-[3-(4-Bromo-phenyl)-pyrazol-1-ylmethyl]-3-methyl-isoxazol-5-yl}-biphenyl-4-yl)-cyclopropanecarboxylic acid ethyl ester: Prepared according to the procedure described in Example 6, Step 3, using 1-[4'-(4-bromomethyl-3-methyl-isoxazol-5-yl)-biphenyl-4-yl]-cyclopropanecarboxylic acid ethyl ester and 3-(4-bromo-phenyl)-1H-pyrazole.

Step 2: The ester from Step 1 was hydrolyzed to the acid according to the procedure described in Example 3.

Example 11

Synthesis of 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid (Compound 6)

Step 1: [5-(4-Bromo-phenyl)-3-methyl-isoxazol-4-ylmethyl]-(5-phenyl-[1,3,4]oxadiazol-2-yl)-amine: Prepared according to the procedure described in Example 2, using 5-(4-bromo-phenyl)-3-methyl-isoxazole-4-carbaldehyde and 5-phenyl-[1,3,4]oxadiazol-2-ylamine.

Step 2: 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid ethyl ester: Prepared according to the procedure described in Example 1, Step 10, using [5-(4-bromo-phenyl)-3-methyl-isoxazol-4-ylmethyl]-(5-phenyl-

[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 12

Synthesis of 1-{4'-[3-Methyl-4-(5-phenyl-[1,2,3]triazol-1-ylmethyl)-isoxazol-5-yl]-biphenyl-4-yl}-cyclopropanecarboxylic acid (Compound 7)

Step 1: 1-{4'-[3-Methyl-4-(5-phenyl-[1,2,3]triazol-1-ylmethyl)-isoxazol-5-yl]-biphenyl-4-yl}-cyclopropanecarboxylic acid ethyl ester: Prepared according to the procedure described in Example 6, Step 3, using 1-[4'-(4-bromomethyl-3-methyl-isoxazol-5-yl)-biphenyl-4-yl]-cyclopropanecarboxylic acid ethyl ester and 5-phenyl-1H-[1,2,3]triazole.

Step 2: The ester from Step 1 was hydrolyzed to the acid according to the procedure described in Example 3.

Example 13

Synthesis of 1-{4'-[3-Methyl-4-(5-phenyl-tetrazol-2-ylmethyl)-isoxazol-5-yl]-biphenyl-4-yl}-cyclopropanecarboxylic acid (Compound 8)

Step 1: 1-{4'-[3-Methyl-4-(5-phenyl-tetrazol-2-ylmethyl)-isoxazol-5-yl]-biphenyl-4-yl}-cyclopropanecarboxylic acid ethyl ester: Prepared according to the procedure described in Example 6, Step 3, using 1-[4'-(4-bromomethyl-3-methyl-isoxazol-5-yl)-biphenyl-4-yl]-cyclopropanecarboxylic acid ethyl ester and 5-phenyl-2H-tetrazole.

Step 2: The ester from Step 1 was hydrolyzed to the acid according to the procedure described in Example 3.

Example 14

Synthesis of 1-{4'-[3-Methyl-4-(4-phenyl-pyrazol-1-ylmethyl)-isoxazol-5-yl]-biphenyl-4-yl}-cyclopropanecarboxylic acid (Compound 9)

Step 1: 1-{4'-[4-(4-Bromo-pyrazol-1-ylmethyl)-3-methyl-isoxazol-5-yl]-biphenyl-4-yl}-cyclopropanecarboxylic acid ethyl ester: Prepared according to the procedure described in Example 6, Step 3, using 1-[4'-(4-bromomethyl-3-methyl-isoxazol-5-yl)-biphenyl-4-yl]-cyclopropanecarboxylic acid ethyl ester and 4-Bromo-1H-pyrazole.

Step 2: 1-{4'-[3-Methyl-4-(4-phenyl-pyrazol-1-ylmethyl)-isoxazol-5-yl]-biphenyl-4-yl}-cyclopropanecarboxylic acid ethyl ester: 1-{4'-[4-(4-Bromo-pyrazol-1-ylmethyl)-3-methyl-isoxazol-5-yl]-biphenyl-4-yl}-cyclopropanecarboxylic acid ethyl ester (0.062 g, 0.122 mmol), phenylboronic acid (0.018 g, 0.146 mmol), tri(o-tolyl)phosphine (0.004 g, 0.0122 mmol) and sodium bicarbonate (0.041 g, 0.488 mmol) were dissolved in DME (1.5 mL) and H$_2$O (0.5 mL) and N$_2$ (g) was bubbled through the mixture for 10 minutes. Palladium(II) acetate (1 mg, 0.002 mmol) was added and the reaction was heated to 90° C. for 1 hour. The reaction was cooled and purified via silica gel chromatography to afford the title compound.

Step 3: 1-{4'-[3-Methyl-4-(4-phenyl-pyrazol-1-ylmethyl)-isoxazol-5-yl]-biphenyl-4-yl}-cyclopropanecarboxylic acid: 1-{4'-[3-Methyl-4-(4-phenyl-pyrazol-1-ylmethyl)-isoxazol-5-yl]-biphenyl-4-yl}-cyclopropanecarboxylic acid ethyl ester (0.051 g, 0.101 mmol) was dissolved in THF (1 mL) then MeOH (0.5 mL) and NaOH (3N aq., 0.5 mL) was added and the reaction stirred at room temperature. After 8 hours the reaction was acidified with 1N aq. HCl then submitted to standard workup procedures to give the title compound.

Example 15

Synthesis of 1-{4'-[4-(5-Benzyl-[1,3,4]oxadiazol-2-yl)-3-methyl-isoxazol-5-yl]-biphenyl-4-yl}-cyclopropanecarboxylic acid (Compound 10)

Step 1: 5-(4-Bromo-phenyl)-3-methyl-isoxazole-4-carboxylic acid hydrazide: 5-(4-Bromo-phenyl)-3-methyl-isoxazole-4-carboxylic acid (0.061 g, 2.16 mmol) was dissolved in THF (5 mL) then 1,1'-carbonyldiimidazole (0.390 g, 2.38 mmol) was added and the reaction was heated to 70° C. for 40 minutes. The reaction was then cooled to 0° C. and hydrazine monohydrate (0.220 mL, 4.32 mmol) was added. The reaction was then allowed to slowly warm to room temperature and stirred overnight. Standard aqueous workup afforded the title compound, which was brought to the next step without further purification.

Step 2: 2-Benzyl-5-[5-(4-bromo-phenyl)-3-methyl-isoxazol-4-yl]-[1,3,4]oxadiazole: Prepared according to the procedure described in Example 8, Step 6, using 5-(4-bromo-phenyl)-3-methyl-isoxazole-4-carboxylic acid hydrazide and phenylacetyl chloride.

Step 3: 1-{4'-[4-(5-Benzyl-[1,3,4]oxadiazol-2-yl)-3-methyl-isoxazol-5-yl]-biphenyl-4-yl}-cyclopropanecarboxylic acid ethyl ester: Prepared according to the procedure described in Example 1, Step 10, using 2-benzyl-5-[5-(4-bromo-phenyl)-3-methyl-isoxazol-4-yl]-[1,3,4]oxadiazole and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 14, Step 3.

Example 16

Synthesis of 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Compound 11)

Step 1: 1-[5-(4-Bromo-phenyl)-3-methyl-isoxazol-4-yl]-prop-2-yn-1-ol: 5-(4-Bromo-phenyl)-3-methyl-isoxazole-4-carbaldehyde (0.285 g, 1.07 mmol) was dissolved in THF (8 mL) and the solution was cooled to −78° C. Ethynylmagnesium bromide (0.5M in THF, 2.6 mL, 1.28 mmol) was added dropwise and the reaction was allowed to warm to room temperature. After 1 hour the reaction was quenched with aqueous ammonium chloride the submitted to standard workup to yield the title compound.

Step 2: (1-Benzyl-1H-[1,2,3]triazol-4-yl)-[5-(4-bromo-phenyl)-3-methyl-isoxazol-4-yl]-methanol: Prepared according to the procedure described in Example 9, Step 2, using 1-[5-(4-bromo-phenyl)-3-methyl-isoxazol-4-yl]-prop-2-yn-1-ol and azidomethyl-benzene.

Step 3: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester: Prepared according to the procedure described in Example 1, Step 10, using (1-benzyl-1H-[1,2,3]triazol-4-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 14, Step 3.

Example 17

Synthesis of 1-[4'-(4-Formyl-3-methyl-isoxazol-5-yl)-biphenyl-4-yl]-cyclopropanecarboxylic acid ethyl ester Step 1: 5-(4-Bromo-phenyl)-3-methyl-isoxazole-4-carbaldehyde (0.5 g, 1.88 mmol) was mixed with 1-[4-(4,4,5,5-Tetramethyl-[1,3,2]dioxaborolan-2-yl)-phenyl]-cyclopropanecarboxylic acid ethyl ester (0.72 g, 2.07 mmol) and sodium bicarbonate (0.553 g, 6.58 mmol) in DME (5 mL) and $H_2O$ (2.5 mL). The reaction was purged with $N_2$ (g) then bis(triphenylphosphine)palladium(II) dichloride (0.066 g, 0.094 mmol) was added and the reaction was heated to 85° C. overnight. After cooling to room temperature the reaction was submitted to standard aqueous workup the purified by silica gel chromatograph (0-20% EtOAc in hexanes) to give the title compound.

Example 18

Synthesis of 1-{4'-[4-(5-Benzyl-[1,3,4]oxadiazol-2-ylmethyl)-3-methyl-isoxazol-5-yl]-biphenyl-4-yl}-cyclopropanecarboxylic acid (Compound 12)

Step 1: 2-Benzyl-5-[5-(4-bromo-phenyl)-3-methyl-isoxazol-4-ylmethyl]-[1,3,4]oxadiazole: Prepared according to the procedure described in Example 8, Step 6, using [5-(4-bromo-phenyl)-3-methyl-isoxazol-4-yl]-acetic acid hydrazide and phenylacetyl chloride.

Step 2: 1-{4'-[4-(5-Benzyl-[1,3,4]oxadiazol-2-ylmethyl)-3-methyl-isoxazol-5-yl]-biphenyl-4-yl}-cyclopropanecarboxylic acid ethyl ester: Prepared according to the procedure described in Example 1, Step 10, using 2-benzyl-5-[5-(4-bromo-phenyl)-3-methyl-isoxazol-4-ylmethyl]-[1,3,4]oxadiazole and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 14, Step 3.

Example 19

Synthesis of 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Compound 13)

Step 1: (5-Benzyl-[1,3,4]oxadiazol-2-yl)-[5-(4-bromo-phenyl)-3-methyl-isoxazol-4-yl]-methanol: 2-Benzyl-[1,3,4]oxadiazole (0.500 g, 3.12 mmol) was dissolved in THF and cooled to −70° C. then n-butyllithium (1.5M in THF, 2.1 mL, 3.12 mmol) was added and the reaction stirred for 1.5 hours. Magnesium bromide ethyl etherate (0.631 g, 3.43 mmol) was added and the reaction was allowed to warm to −45° C. After 45 minutes 5-(4-bromo-phenyl)-3-methyl-isoxazole-4-carbaldehyde (0.415 g, 1.56 mmol) in THF (2 mL) was added and the reaction was allowed to stir overnight. The reaction was quenched with aqueous ammonium chloride then submitted to standard workup and purification via silica gel chromatography (0-60% EtOAc in hexanes) to give the title compound.

Step 2: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester: Prepared according to the procedure described in Example 1, Step 10, using (5-benzyl-[1,3,4]oxadiazol-2-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 14, Step 3.

Example 20

Synthesis of 1-{4'-[4-(1-Benzyl-1H-[1,2,3]triazol-4-ylmethyl)-3-methyl-isoxazol-5-yl]-biphenyl-4-yl}-cyclopropanecarboxylic acid (Compound 14)

Step 1: 1-{4'-[4-(1-Benzyl-1H-[1,2,3]triazol-4-ylmethyl)-3-methyl-isoxazol-5-yl]-biphenyl-4-yl}-cyclopropanecarboxylic acid ethyl ester: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (0.123 g, 0.230 mmol) and triethylsilane (0.044 mL, 0.276 mmol) were dissolved in $CH_2Cl_2$ (0.5 mL) then trifluoromethanesulfonic acid (0.5 mL) was slowly added. After stirring for 1 hour at room temperature, an additional portion of triethylsilane (0.050 mL) was added and the reaction was heated to 50° C. for 3.5 hours. An additional portion of triethylsilane (1 mL) was added and the reaction continued to stir at 50° C. for 1 hour. The reaction mixture was concentrated, dissolved in $CH_2Cl_2$, and filtered through a plug of silica gel. The crude material was then purified via preparatory HPLC to afford the title compound.

Step 2: The ester from Step 1 was hydrolyzed to the acid according to the procedure described in Example 14, Step 3.

Example 21

Synthesis of 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer A) (Compound 15)

Step 1: (5-Benzyl-[1,3,4]oxadiazol-2-yl)-[5-(4-bromo-phenyl)-3-methyl-isoxazol-4-yl]-methanol: Prepared according to the procedure described in Example 19, Step 1, using 5-(4-Bromo-phenyl)-3-methyl-isoxazole-4-carbaldehyde and 2-benzyl-[1,3,4]oxadiazole.

The recovered material was purified by silica gel chromatography (0-60% EtOAc in hexanes) then the by preparatory chiral HPLC(CHIRALPAK® AD column, 95:5 hexanes:EtOH) to give enantiomer A (first to elute) and enantiomer B (second to elute) with undetermined absolute stereochemistry.

Step 2: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer A): Prepared according to the procedure described in Example 1, Step 10, using (5-benzyl-[1,3,4]oxadiazol-2-yl)-[5-(4-bromo-phenyl)-3-methyl-isoxazol-4-yl]-methanol (Enantiomer A) and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 14, Step 3.

Example 22

Synthesis of 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer B) (Compound 16)

Step 1: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer B): Prepared according to the procedure described in Example 1, Step 10, using (5-benzyl-[1,3,4]oxadiazol-2-yl)-[5-(4-bromo-phenyl)-3-methyl-isoxazol-4-yl]-methanol (Enantiomer B) and 1-[4-(4,4,5,5-tetramethyl-[1,3,2]dioxaborolan-2-yl)-phenyl]-cyclopropanecarboxylic acid ethyl ester.

Step 2: The ester from Step 1 was hydrolyzed to the acid according to the procedure described in Example 14, Step 3.

Example 23

Synthesis of 5-(4-Bromo-phenyl)-3-methyl-isoxazol-4-ylamine

Step 1: 5-(4-Bromo-phenyl)-3-methyl-isoxazol-4-ylamine: Prepared according to the procedure described in Example 1, Step 11, using [5-(4-bromo-phenyl)-3-methyl-isoxazol-4-yl]-carbamic acid tert-butyl ester.

Example 24

Synthesis of 1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid (Compound 17)

Step 1: 2-Phenyl-[1,3,4]oxadiazole: Benzoic acid methyl ester (1.01 g, 7.34 mmol) and hydrazine monohydrate (10 mL) were dissolved in EtOH (20 mL) then heated in a sealed tube to 80° C. for 23 hours. The reaction was allowed to cool and then triethylorthoformate (25 mL) and p-toluenesulfonic acid (0.100 g, 0.526 mmol) were added, the tube was re-sealed, and the reaction was heated to 120° C. for 26 hours. The reaction mixture was then submitted to standard aqueous workup and purified on silica gel (0-70% EtOAc in hexanes) to afford the title compound.

Step 2: [5-(4-Bromo-phenyl)-3-methyl-isoxazol-4-yl]-(5-phenyl-[1,3,4]oxadiazol-2-yl)-methanol: Prepared according to the procedure described in Example 19, Step 1, using 5-(4-Bromo-phenyl)-3-methyl-isoxazole-4-carbaldehyde and 2-phenyl-[1,3,4]oxadiazole.

Step 3: 1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid ethyl ester: Prepared according to the procedure described in Example 17, Step 1, using [5-(4-bromo-phenyl)-3-methyl-isoxazol-4-yl]-(5-phenyl-[1,3,4]oxadiazol-2-yl)-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 14, Step 3.

Example 25

Synthesis of 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer A) (Compound 18)

Step 1: 1-[5-(4-Bromo-phenyl)-3-methyl-isoxazol-4-yl]-prop-2-yn-1-ol: Prepared according to the procedure described in Example 16, Step 1, and after the reaction the material was purified via preparatory chiral HPLC(CHIRALCEL® AD column, 85:15 hexanes:EtOH) to give enantiomer A (first to elute) and enantiomer B (second to elute) with undetermined absolute stereochemistry.

Step 2: (1-Benzyl-1H-[1,2,3]triazol-4-yl)-[5-(4-bromo-phenyl)-3-methyl-isoxazol-4-yl]-methanol (Enantiomer A): To a solution of 1-[5-(4-Bromo-phenyl)-3-methyl-isoxazol-4-yl]-prop-2-yn-1-ol (Enantiomer A) (0.530 g, 1.81 mmol) in DMSO (4 mL) and $H_2O$ (4 mL) was added azidomethylbenzene (0.242 g, 1.81 mmol), followed by sodium ascorbate (0.036 g, 0.181 mmol) and copper(II) sulfate pentahydrate (0.005 g, 0.018 mmol), and the reaction was stirred overnight. After aqueous workup the crude material was purified by silica gel chromatography (15-100% EtOAc in hexanes) to give the title compound.

Step 3: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer A): Prepared according to the procedure described in Example 1, Step 10, using (1-benzyl-1H-[1,2,3]triazol-4-yl)-[5-(4-bromo-phenyl)-3-methyl-isoxazol-4-yl]-methanol (Enantiomer A) and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 14, Step 3.

Example 26

Synthesis of 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer B) (Compound 19)

Step 1: (1-Benzyl-1H-[1,2,3]triazol-4-yl)-[5-(4-bromo-phenyl)-3-methyl-isoxazol-4-yl]-methanol (Enantiomer B): Prepared according to the procedure described in Example 25, Step 2, using 1-[5-(4-Bromo-phenyl)-3-methyl-isoxazol-4-yl]-prop-2-yn-1-ol (Enantiomer B) and azidomethylbenzene.

Step 2: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer B): Prepared according to the procedure described in Example 1, Step 10, using (1-benzyl-1H-[1,2,3]triazol-4-yl)-[5-(4-bromo-phenyl)-3-methyl-isoxazol-4-yl]-methanol (Enantiomer B) and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 14, Step 3.

Example 27

Synthesis of [5-(4-Bromo-phenyl)-3-methyl-isoxazol-4-yl]-[1-(3-phenyl-isoxazol-5-yl)-ethyl]-amine Step 1: Prepared according to the procedure described in Example 2, using 5-(4-bromo-phenyl)-3-methyl-isoxazol-4-ylamine and 1-(3-phenyl-isoxazol-5-yl)-ethanone.

Example 28

Synthesis of 1-[4'-(4-{Hydroxy-[5-(3-trifluoromethyl-benzyl)-[1,3,4]oxadiazol-2-yl]-methyl}-3-methyl-isoxazol-5-yl)-biphenyl-4-yl]-cyclopropanecarboxylic acid (Compound 20)

Step 1: 2-(3-Trifluoromethyl-benzyl)-[1,3,4]oxadiazole: (3-Trifluoromethyl-phenyl)-acetic acid methyl ester (0.720 g, 3.30 mmol) was dissolved in hydrazine (7 mL) and EtOH (15 mL) and heated to 90° C. overnight. Analytical LCMS indicated complete reaction so the mixture was concentrated and azeotroped twice with toluene. The crude material was dissolved in triethylorthoformate and heated to 135° C. for 20 hours then allowed to cool. The reaction mixture was concentrated to afford the title compound.

Step 2: [5-(4-Bromo-phenyl)-3-methyl-isoxazol-4-yl]-[5-(3-trifluoromethyl-benzyl)-[1,3,4]oxadiazol-2-yl]-methanol: Prepared according to the procedure described in Example 19, Step 1, using 5-(4-Bromo-phenyl)-3-methyl-isoxazole-4-carbaldehyde and 2-(3-trifluoromethyl-benzyl)-[1,3,4]oxadiazole.

Step 3: 1-[4'-(4-{Hydroxy-[5-(3-trifluoromethyl-benzyl)-[1,3,4]oxadiazol-2-yl]-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[5-(3-trifluoromethyl-benzyl)-[1,3,4]oxadiazol-2-yl]-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 14, Step 3.

Example 29

Synthesis of 1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 21)

Step 1: [5-(4-Bromo-phenyl)-3-methyl-isoxazol-4-yl]-[1-(3-trifluoromethyl-benzyl)-1H-[1,2,3]triazol-4-yl]-methanol: 1-Bromomethyl-3-trifluoromethyl-benzene (0.0491 g, 0.205 mmol) and sodium azide (0.0222 g, 0.342 mmol) were combined in DMSO and stirred at room temperature for 2 hours. Then, 1-[5-(4-bromo-phenyl)-3-methyl-isoxazol-4-yl]-prop-2-yn-1-ol (0.500 g, 0.171 mmol), copper(II)sulfate pentahydrate (0.0043 g, 0.017 mmol) and sodium ascorbate (0.0034 g, 0.017 mmol) were added and the reaction stirred at room temperature for 2 days. The reaction was submitted to standard aqueous workup and purified on silica gel to afford the title compound.

Step 2: 1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(3-trifluoromethyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 30

Synthesis of 1-{4'-[4-(Biphenyl-3-yl-hydroxy-methyl)-3-methyl-isoxazol-5-yl]-biphenyl-4-yl}-cyclopropanecarboxylic acid (Compound 22)

Step 1: Biphenyl-3-yl-[5-(4-bromo-phenyl)-3-methyl-isoxazol-4-yl]-methanol: Prepared according to the procedure described in Example 16, Step 1, using 5-(4-bromo-phenyl)-3-methyl-isoxazole-4-carbaldehyde and 3-(biphenyl)magnesium bromide.

Step 2: 1-{4'-[4-(Biphenyl-3-yl-hydroxy-methyl)-3-methyl-isoxazol-5-yl]-biphenyl-4-yl}-cyclopropanecarboxylic acid ethyl ester: Prepared according to the procedure described in Example 1, Step 10, using biphenyl-3-yl-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester. Additionally, (1,1'-bis(diphenylphosphino)ferrocene)-dichloropalladium(II) was used as the catalyst in place of tetrakis(triphenylphosphine) palladium(0)

Step 3: 1-{4'-[4-(Biphenyl-3-yl-hydroxy-methyl)-3-methyl-isoxazol-5-yl]-biphenyl-4-yl}-cyclopropanecarboxylic acid: 1-{4'-[4-(Biphenyl-3-yl-hydroxy-methyl)-3-methyl-isoxazol-5-yl]-biphenyl-4-yl}-cyclopropanecarboxylic acid ethyl ester (1 equivalent) was dissolved in THF then EtOH and NaOH (3N aq., 3 equivalents) was added and the reaction stirred at 60° C. overnight. The reaction was worked up and purified via preparatory HPLC (0.1% TFA/H$_2$O/ACN).

Example 31

Synthesis of 1-[4'-(4-{Hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid (Compound 23)

Step 1: [5-(4-Bromo-phenyl)-3-methyl-isoxazol-4-yl]-[1-(1-phenyl-ethyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and (1-bromo-ethyl)-benzene.

Step 2: 1-[4'-(4-{Hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(1-phenyl-ethyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 32

Synthesis of 1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 24)

Step 1: [5-(4-Bromo-phenyl)-3-methyl-isoxazol-4-yl]-[1-(2-trifluoromethyl-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 1-bromomethyl-2-trifluoromethyl-benzene.

Step 2: 1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(2-trifluoromethyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 33

Synthesis of 1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 25)

Step 1: [5-(4-Bromo-phenyl)-3-methyl-isoxazol-4-yl]-[1-(3-chloro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 1-bromomethyl-3-chloro-benzene.

Step 2: 1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(3-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 34

Synthesis of 1-(4'-{4-[(3-Benzyl-phenyl)-hydroxy-methyl]-3-methyl-isoxazol-5-yl}-biphenyl-4-yl)-cyclopropanecarboxylic acid (Compound 26)

Step 1: (3-Bromo-phenyl)-phenyl-methanol: Prepared according to the procedure described in Example 16, Step 1, using 3-bromobenzaldehyde and phenylmagnesium bromide.

Step 2: 1-Benzyl-3-bromo-benzene: (3-Bromo-phenyl)-phenyl-methanol (from previous step) was dissolved in diethyl ether (10 mL) and the solution was added dropwise to a suspension of lithium aluminum hydride (0.607 g, 16 mmol) and aluminum chloride (2.11 g, 16 mmol) stirring in THF (15 mL). The reaction was heated to 40° C. for 1 hour then cooled to 0° C., quenched with $H_2O$, and submitted to standard aqueous workup. The crude product was purified via silica gel chromatography (0-5% EtOAc in hexanes) to afford the title compound.

Step 3: (3-Benzyl-phenyl)-[5-(4-bromo-phenyl)-3-methyl-isoxazol-4-yl]-methanol: 1-Benzyl-3-bromo-benzene (0.811 g, 3.3 mmol) was dissolved in THF (2 mL), cooled to −78° C. and then n-butyllithium (2.0 M in THF, 1.65 mL, 3.3 mmol) was added dropwise. The reaction was stirred for 15 minutes then warmed to 0° C. and 5-(4-bromo-phenyl)-3-methyl-isoxazole-4-carbaldehyde (1.05 g, 3.96 mmol) was added. The reaction was allowed to warm to room temperature while stirring for 1 hour. The reaction was quenched with aqueous ammonium chloride then submitted to standard aqueous workup and silica gel chromatography to give the title compound.

Step 4: 1-(4'-{4-[(3-Benzyl-phenyl)-hydroxy-methyl]-3-methyl-isoxazol-5-yl}-biphenyl-4-yl)-cyclopropanecarboxylic acid ethyl ester: Prepared according to the procedure described in Example 17, Step 1, using (3-benzyl-phenyl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 5: The ester from Step 4 was hydrolyzed to the acid according to the procedure described in Example 3.

Example 35

Synthesis of 1-(4'-{4-[(5-Benzyl-pyridin-3-yl)-hydroxy-methyl]-3-methyl-isoxazol-5-yl}-biphenyl-4-yl)-cyclopropanecarboxylic acid (Compound 27)

Step 1: 3-Benzyl-5-bromo-pyridine: Benzylmagnesium bromide (1.0 M in THF, 20 mL, 20 mmol) was added to a solution of zinc chloride (2.73 g, 20 mmol) in THF (20 mL) and the reaction was heated to 50° C. for 2.5 hours. The solution was then added by cannula to a solution of 3,5-dibromo-pyridine (3.07 g, 13 mmol), copper(I) iodide (0.0148 g, 0.78 mmol), and (1,1'-bis(diphenylphosphino)ferrocene)-dichloropalladium(II) (0.048 g, 0.65 mmol) in THF (20 mL). The reaction was heated to 50° C. for 48 hours then quenched with $H_2O$, submitted to standard aqueous workup, and purified via silica gel chromatography (0-50% EtOAc in hexanes) to give the title compound.

Step 2: (5-Benzyl-pyridin-3-yl)-[5-(4-bromo-phenyl)-3-methyl-isoxazol-4-yl]-methanol: 3-Benzyl-5-bromo-pyridine (0.474 g, 1.91 mmol) was dissolved in THF (10 mL) and cooled to 0° C. Isopropylmagnesium chloride (2 M in THF, 0.96 mL, 1.91 mmol) was added dropwise and the reaction was allowed to warm to room temperature and stirred for 1 hour. Analytical LCMS indicated no reaction so an additional portion of isopropylmagnesium chloride (1.91 mmol) was added and the reaction stirred for 1 hour at room temperature. Analytical LCMS still indicated no progress so the reaction was cooled to −78° C. and n-butyllithium (2.5 M in hexanes, 0.764 mL, 1.91 mL) was added. The reaction was allowed to slowly warm to 0° C. then 5-(4-bromo-phenyl)-3-methyl-isoxazole-4-carbaldehyde (0.610 g, 2.29 mmol) was added and the reaction was allowed to warm to room temperature. The reaction was quenched with $H_2O$, submitted to standard aqueous workup and then purified via silica gel chromatography to yield the title compound.

Step 3: 1-(4'-{4-[(5-Benzyl-pyridin-3-yl)-hydroxy-methyl]-3-methyl-isoxazol-5-yl}-biphenyl-4-yl)-cyclopropanecarboxylic acid ethyl ester: Prepared according to the procedure described in Example 17, Step 1, using (5-benzyl-pyridin-3-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 3.

Example 36

Synthesis of 1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 28)

Step 1: [5-(4-Bromo-phenyl)-3-methyl-isoxazol-4-yl]-[1-(2-chloro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 1-bromomethyl-2-chloro-benzene.

Step 2: 1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-Bromo-phenyl)-3-methyl-isoxazol-4-yl]-[1-(2-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 37

Synthesis of 1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 29)

Step 1: [5-(4-Bromo-phenyl)-3-methyl-isoxazol-4-yl]-[1-(4-chloro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 1-bromomethyl-4-chloro-benzene.

Step 2: 1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-Bromo-phenyl)-3-methyl-isoxazol-4-yl]-[1-(4-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 38

Synthesis of 1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 30)

Step 1: (S)-1-[5-(4-Bromo-phenyl)-3-methyl-isoxazol-4-yl]-prop-2-yn-1-ol: Zinc triflate (0.75 g, 2.1 mmol), (1S,2R)-(+)-N-methylephedrine (0.41 g, 2.3 mmol) and triethylamine (0.23 g, 2.3 mmol) were stirred in toluene (10 mL) at room temperature for 2 hours. (Trimethylsilyl)acetylene (0.32 g, 2.3 mmol) was added and the reaction stirred for 15 minute then 5-(4-bromo-phenyl)-3-methyl-isoxazole-4-carbaldehyde (0.5 g, 1.9 mmol) was added and the reaction stirred at room temperature for 2 weeks. The reaction mixture was purified on by silica gel chromatography (0-20% EtOAc in hexanes) to afford the title product with 97.5% ee as measured by analytical chiral HPLC.

Step 2: (R)-[5-(4-Bromo-phenyl)-3-methyl-isoxazol-4-yl]-[1-(2-chloro-benzyl)-1H-[1,2,3]triazol-4-yl]-methanol: Prepared according to the procedure described in Example 29, Step 1, using (S)-1-[5-(4-bromo-phenyl)-3-methyl-isoxazol-4-yl]-prop-2-yn-1-ol and 1-bromomethyl-2-chloro-benzene.

Step 3: 1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using (R)-[5-(4-bromo-phenyl)-3-methyl-isoxazol-4-yl]-[1-(2-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 3.

Example 39

Synthesis of 1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 31)

Step 1: [5-(4-Bromo-phenyl)-3-methyl-isoxazol-4-yl]-[1-(3,4-dichloro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 4-bromomethyl-1,2-dichloro-benzene.

Step 2: 1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(3,4-dichloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 40

Synthesis of 1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid (Compound 32)

Step 1: ((S)-1-Bromo-ethyl)-benzene: Bromine (3.2 g, 20.0 mmol) was added to a suspension of triphenylphosphine (5.2 g, 19.8 mmol) stirring in ACN at −15° C. The reaction was warmed to room temperature and stirred for 50 minutes then cooled to −35° C. and (R)-(+)-1-phenylethanol (1.6 g, 13.1 mmol) was added. The reaction was allowed to warm to −10° C. over 70 minutes and was then quenched with $H_2O$ and submitted to standard aqueous workup to afford the title compound which was used without further purification.

Step 2: (R)-[5-(4-Bromo-phenyl)-3-methyl-isoxazol-4-yl]-[1-((R)-1-phenyl-ethyl)-1H-[1,2,3]triazol-4-yl]-methanol: Prepared according to the procedure described in Example 29, Step 1, using (S)-1-[5-(4-bromo-phenyl)-3-methyl-isoxazol-4-yl]-prop-2-yn-1-ol and ((R)-1-bromo-ethyl)-benzene.

Step 3: 1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid ethyl ester: Prepared according to the procedure described in Example 1, Step 10, using (R)-[5-(4-Bromo-phenyl)-3-methyl-isoxazol-4-yl]-[1-((R)-1-phenyl-ethyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 4: The ester from Step 3 was hydrolyzed to the acid according to the procedure described in Example 3.

Example 41

Synthesis of 1-{4'-[3-Methyl-4-(6-phenyl-pyridin-2-ylamino)-isoxazol-5-yl]-biphenyl-4-yl}-cyclopropanecarboxylic acid (Compound 33)

Step 1: 2-Bromo-6-phenyl-pyridine: 2,6-Dibromo-pyridine (1.2 g, 0.508 mmol), phenylboronic acid (0.620 g, 0.508 mmol) and sodium carbonate (2 M aq., 30 mL) were dissolved in MeOH (10 mL) and toluene (30 mL) and the solution was degassed with bubbling $N_2$ (g). Tetrakis(triphenylphosphine)palladium(0) (0.172 g, 0.149 mmol) was added and the reaction was heated to 100° C. overnight. After cooling the reaction was submitted to standard aqueous workup and purified by silica gel chromatography to give the title compound.

Step 2: 1-{4'-[3-Methyl-4-(6-phenyl-pyridin-2-ylamino)-isoxazol-5-yl]-biphenyl-4-yl}-cyclopropanecarboxylic acid ethyl ester: 1-[4'-(4-Amino-3-methyl-isoxazol-5-yl)-biphenyl-4-yl]-cyclopropanecarboxylic acid ethyl ester (0.250 g, 0.689 mmol), 2-bromo-6-phenyl-pyridine (0.1457 g, 0.62 mmol), cesium carbonate (0.2694 g, 0.826 mmol) and (±)-2,2'-bis(diphenylphosphino)-1,1'-binaphthyl (0.032 g, 0.052 mmol) were dissolved in toluene (3 mL) and the solution was degassed with bubbling $N_2$ (g). Tris(dibenzylideneacetone)dipalladium(0) (0.0158 g, 0.017 mmol) was added and the reaction was heated to 110° C. for 24 hours. After cooling the reaction was submitted to standard aqueous workup and silica gel chromatography to afford the title compound.

Step 3: The ester from Step 2 was hydrolyzed to the acid according to the procedure described in Example 3.

Example 42

Synthesis of 1-(4'-{4-[(6-Benzyl-pyridin-2-yl)-hydroxy-methyl]-3-methyl-isoxazol-5-yl}-biphenyl-4-yl)-cyclopropanecarboxylic acid (Compound 34)

Step 1: 2-Benzyl-6-bromo-pyridine: 2,6-Dibromopyridine (2.36 g, 1 mmol), benzylzinc bromide (0.9 M in THF, 1.05 mL, 0.95 mmol) and tetrakis(triphenylphosphine)palladium(0) (0.012 g, 0.01 mmol) were placed in THF (75 mL) and heated to 60° C. for 20 hours. The reaction mixture was cooled, submitted to standard aqueous workup and purified on silica gel to afford the title compound.

Step 2: (6-Benzyl-pyridin-2-yl)-[5-(4-bromo-phenyl)-3-methyl-isoxazol-4-yl]-methanol: Prepared according to the procedure described in Example 34, Step 3, using 5-(4-bromo-phenyl)-3-methyl-isoxazole-4-carbaldehyde and 2-benzyl-6-bromo-pyridine.

Step 3: 1-(4'-{4-[(6-Benzyl-pyridin-2-yl)-hydroxymethyl]-3-methyl-isoxazol-5-yl}-biphenyl-4-yl)-cyclopropanecarboxylic acid ethyl ester: Prepared according to the procedure described in Example 1, Step 10, using (6-benzyl-pyridin-2-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester. Additionally, (1,1'-bis(diphenylphosphino)ferrocene)-dichloropalladium(II) was used as the catalyst in place of tetrakis(triphenylphosphine)palladium(0).

Step 4: The ester from Step 3 was hydrolyzed to the acid according to the procedure described in Example 3.

Example 43

Synthesis of 1-[4'-(4-{Hydroxy-[1-(2-methyl-benzyl)-1H-[1,2,3]triazol-4-yl]-methyl}-3-methyl-isoxazol-5-yl)-biphenyl-4-yl]-cyclopropanecarboxylic acid (Compound 35)

Step 1: [5-(4-Bromo-phenyl)-3-methyl-isoxazol-4-yl]-[1-(2-methyl-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 1-bromomethyl-2-methyl-benzene.

Step 2: 1-[4'-(4-{Hydroxy-[1-(2-methyl-benzyl)-1H-[1,2,3]triazol-4-yl]-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(2-methyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 44

Synthesis of 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid (Compound 36)

Step 1: [5-(4-Bromo-phenyl)-3-methyl-isoxazol-4-yl]-[1-(2-chloro-6-fluoro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 2-bromomethyl-1-chloro-3-fluoro-benzene.

Step 2: 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(2-chloro-6-fluoro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 45

Synthesis of 1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 37)

Step 1: [5-(4-Bromo-phenyl)-3-methyl-isoxazol-4-yl]-[1-(2,6-dichloro-benzyl)-1H-[1,2,3]triazol-4-yl]-methanol: Prepared according to the procedure described in Example 29, Step 1, using 1-[5-(4-bromo-phenyl)-3-methyl-isoxazol-4-yl]-prop-2-yn-1-ol and 2-bromomethyl-1,3-dichloro-benzene.

Step 2: 1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester: Prepared according to the procedure described in Example 1, Step 10, using [5-(4-bromo-phenyl)-3-methyl-isoxazol-4-yl]-[1-(2,6-dichloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

Step 3: The ester from Step 2 was hydrolyzed to the acid according to the procedure described in Example 3.

Example 46

Synthesis of 1-{4'-[4-(6-Benzyl-pyridin-2-ylamino)-3-methyl-isoxazol-5-yl]-biphenyl-4-yl}-cyclopropanecarboxylic acid (Compound 38)

Step 1: 1-{4'-[4-(6-Benzyl-pyridin-2-ylamino)-3-methyl-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-benzyl-6-bromo-pyridine.

Step 2: The ester from Step 1 was hydrolyzed to the acid according to the procedure described in Example 3.

Example 47

Synthesis of 1-{4'-[4-(Biphenyl-3-ylamino)-3-methyl-isoxazol-5-yl]-biphenyl-4-yl}-cyclopropanecarboxylic acid (Compound 39)

Step 1: 1-{4'-[4-(Biphenyl-3-ylamino)-3-methyl-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-biphenyl.

Step 2: The ester from Step 1 was hydrolyzed to the acid according to the procedure described in Example 3.

Example 48

Synthesis of 1-{4'-[4-(Biphenyl-4-ylamino)-3-methyl-isoxazol-5-yl]-biphenyl-4-yl}-cyclopropanecarboxylic acid (Compound 40)

Step 1: 1-{4'-[4-(Biphenyl-4-ylamino)-3-methyl-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 4-bromo-biphenyl.

Step 2: The ester from Step 1 was hydrolyzed to the acid according to the procedure described in Example 3.

Example 49

Synthesis of 1-(4'-{3-Methyl-4-[6-(3-trifluoromethyl-phenyl)-pyridin-2-ylamino]-isoxazol-5-yl}-biphenyl-4-yl)-cyclopropanecarboxylic acid (Compound 41)

Step 1: 4,4,5,5-Tetramethyl-2-(3-trifluoromethyl-phenyl)-[1,3,2]dioxaborolane: Prepared according to the procedure described in Example 1, Step 9, using 1-bromo-3-trifluoromethyl-benzene and bis(pinacolato)diboron.

Step 2: 2-Bromo-6-(3-trifluoromethyl-phenyl)-pyridine: Prepared according to the procedure described in Example 1, Step 10, using 4,4,5,5-tetramethyl-2-(3-trifluoromethyl-phenyl)-[1,3,2]dioxaborolane and 2,6-dibromo-pyridine. Additionally, (1,1'-bis(diphenylphosphino)ferrocene)-dichloropalladium(II) was used as the catalyst in place of tetrakis(triphenylphosphine)palladium(0).

Step 3: 1-(4'-{3-Methyl-4-[6-(3-trifluoromethyl-phenyl)-pyridin-2-ylamino]-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-6-(3-trifluoromethyl-phenyl)-pyridine.

Step 4: The ester from Step 3 was hydrolyzed to the acid according to the procedure described in Example 3.

Example 50

Synthesis of 1-{4'-[3-Methyl-4-(6-phenyl-pyrazin-2-ylamino)-isoxazol-5-yl]-biphenyl-4-yl}-cyclopropanecarboxylic acid (Compound 42)

Step 1: 2-Bromo-6-phenyl-pyrazine: Prepared according to the procedure described in Example 1, Step 10, using 2,6-dibromo-pyrazine and phenylboronic acid. Additionally, (1,1'-bis(diphenylphosphino)ferrocene)-dichloropalladium (II) was used as the catalyst in place of tetrakis(triphenylphosphine)palladium(0).

Step 2: 1-{4'-[3-Methyl-4-(6-phenyl-pyrazin-2-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-6-phenyl-pyrazine.

Step 3: The ester from Step 2 was hydrolyzed to the acid according to the procedure described in Example 3.

Example 51

Synthesis of 1-{4'-[3-Methyl-4-(5-phenyl-[1,3,4]oxadiazol-2-ylamino)-isoxazol-5-yl]-biphenyl-4-yl}-cyclopropanecarboxylic acid (Compound 43)

Step 1: [5-(4-Bromo-phenyl)-3-methyl-isoxazol-4-yl]-(5-phenyl-[1,3,4]oxadiazol-2-yl)-amine: 5-(4-Bromo-phenyl)-3-methyl-isoxazole-4-carboxylic acid (1 g, 3.6 mmol), triethylamine (1 mL, 7.2 mmol) and diphenylphosphoryl azide (1.98 g, 7.2 mmol) were placed in toluene (20 mL) and heated to 60° C. for 20 minutes. Benzoic acid hydrazide (0.98 g, 7.2 mmol) was added in a single portion and the reaction was heated and stirred for 2 hours. The reaction was cooled and submitted to aqueous workup. The crude material was dissolved in dioxane (100 mL), phosphorous(V) oxychloride was added and the reaction was heated to 100° C. overnight. The reaction was cooled and worked up and the residue was purified on silica gel (0-80% EtOAc in hexanes) to yield the title compound.

Step 2: 1-{4'-[3-Methyl-4-(5-phenyl-[1,3,4]oxadiazol-2-ylamino)-isoxazol-5-yl]-biphenyl-4-yl}-cyclopropanecarboxylic acid ethyl ester: Prepared according to the procedure described in Example 1, Step 10, using [5-(4-bromo-phenyl)-3-methyl-isoxazol-4-yl]-(5-phenyl-[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester. Additionally, (1,1'-bis(diphenylphosphino)ferrocene)-dichloropalladium(II) was used as the catalyst in place of tetrakis(triphenylphosphine)palladium(0).

Step 3: The ester from Step 2 was hydrolyzed to the acid according to the procedure described in Example 3.

Example 52

Synthesis of 1-{4'-[4-(5-Benzyl-[1,3,4]oxadiazol-2-ylamino)-3-methyl-isoxazol-5-yl]-biphenyl-4-yl}-cyclopropanecarboxylic acid (Compound 44)

Step 1: Phenyl-acetic acid hydrazide: Phenyl-acetic acid methyl ester (5 g, 33.3 mmol) was dissolved in hydrazine hydrate (25 mL) and EtOH (50 mL) and the reaction was heated in a sealed tube to 80° C. overnight. After cooling the reaction was concentrated to afford the title compound.

Step 2: (5-Benzyl-[1,3,4]oxadiazol-2-yl)-[5-(4-bromo-phenyl)-3-methyl-isoxazol-4-yl]-amine: Prepared according to the procedure described in Example 51, Step 1, using 5-(4-bromo-phenyl)-3-methyl-isoxazole-4-carboxylic acid and phenyl-acetic acid hydrazide.

Step 3: 1-{4'-[4-(5-Benzyl-[1,3,4]oxadiazol-2-ylamino)-3-methyl-isoxazol-5-yl]-biphenyl-4-yl}-cyclopropanecarboxylic acid ethyl ester: Prepared according to the procedure described in Example 1, Step 10, using (5-benzyl-[1,3,4]oxadiazol-2-yl)-[5-(4-bromo-phenyl)-3-methyl-isoxazol-4-yl]-amine and 1-[4-(4,4,5,5-tetramethyl-[1,3,2]dioxaborolan-2-yl)-phenyl]-cyclopropanecarboxylic acid ethyl ester. Additionally, (1,1'-bis(diphenylphosphino)ferrocene)-dichloropalladium(II) was used as the catalyst in place of tetrakis(triphenylphosphine)palladium(0).

Step 4: The ester from Step 4 was hydrolyzed to the acid according to the procedure described in Example 3.

Example 53

Synthesis of 1-(4'-{4-[6-(2-Fluoro-benzyl)-pyridin-2-ylamino]-3-methyl-isoxazol-5-yl}-biphenyl-4-yl)-cyclopropanecarboxylic acid (Compound 45)

Step 1: 2-Fluoro-benzylzinc bromide: 2-Fluoro-benzyl bromide (1 g, 5.29 mmol), zinc (0.380 g, 5.82 mmol) and 1,2-dibromoethane (0.050 mL, 0.58 mmol) were mixed in THF (10 mL) and heated to reflux overnight. After cooling a solution of the title compound was obtained that was used directly and immediately in the next step.

Step 2: 2-Bromo-6-(2-fluoro-benzyl)-pyridine: A solution of 2-fluoro-benzylzinc bromide was added to 2,6-dibromo-pyridine (1.25 g, 5.27 mmol) then tetrakis(triphenylphosphine)palladium(0) (0.122 g, 0.106 mmol) was added and the reaction was heated to 68° C. for 4 hours. After cooling, silica gel was added to the reaction and it was concentrated to near-dryness. The silica gel was loaded onto a column of silica gel for purification to afford the title compound.

Step 3: 1-(4'-{4-[6-(2-Fluoro-benzyl)-pyridin-2-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-6-(2-fluoro-benzyl)-pyridine.

Step 4: The ester from Step 3 was hydrolyzed to the acid according to the procedure described in Example 3.

Example 54

Synthesis of 1-(4'-{4-[6-(3-Fluoro-benzyl)-pyridin-2-ylamino]-3-methyl-isoxazol-5-yl}-biphenyl-4-yl)-cyclopropanecarboxylic acid (Compound 46)

Step 1: 3-Fluoro-benzylzinc bromide: Prepared according to the procedure described in Example 53, Step 1, using 3-fluoro-benzyl bromide.

Step 2: 2-Bromo-6-(3-fluoro-benzyl)-pyridine: Prepared according to the procedure described in Example 53, Step 2, using 2,6-dibromo-pyridine and 3-fluoro-benzylzinc bromide.

Step 3: 1-(4'-{4-[6-(3-Fluoro-benzyl)-pyridin-2-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-6-(3-fluoro-benzyl)-pyridine.

Step 4: The ester from Step 3 was hydrolyzed to the acid according to the procedure described in Example 3.

Example 55

Synthesis of 1-(4'-{4-[6-(4-Fluoro-benzyl)-pyridin-2-ylamino]-3-methyl-isoxazol-5-yl}-biphenyl-4-yl)-cyclopropanecarboxylic acid (Compound 47)

Step 1: 4-Fluoro-benzylzinc bromide: Prepared according to the procedure described in Example 53, Step 1, using 4-fluoro-benzyl bromide.

Step 2: 2-Bromo-6-(4-fluoro-benzyl)-pyridine: Prepared according to the procedure described in Example 53, Step 2, using 2,6-dibromo-pyridine and 4-fluoro-benzylzinc bromide.

Step 3: 1-(4'-{4-[6-(4-Fluoro-benzyl)-pyridin-2-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-6-(4-fluoro-benzyl)-pyridine.

Step 4: The ester from Step 3 was hydrolyzed to the acid according to the procedure described in Example 3.

Example 56

Synthesis of 1-(4'-{4-[6-(3-Methoxy-phenyl)-pyridin-2-ylamino]-3-methyl-isoxazol-5-yl}-biphenyl-4-yl)-cyclopropanecarboxylic acid (Compound 48)

Step 1: 1-(4'-{4-[6-(3-Methoxy-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-methoxyphenylboronic acid.

Step 2: The ester from Step 1 was hydrolyzed to the acid according to the procedure described in Example 3.

Example 57

Synthesis of 1-{4'-[4-(3-Benzyl-phenylamino)-3-methyl-isoxazol-5-yl]-biphenyl-4-yl}-cyclopropanecarboxylic acid (Compound 49)

Step 1: 1-{4'-[4-(3-Benzyl-phenylamino)-3-methyl-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 1-benzyl-3-bromo-benzene.

Step 2: The ester from Step 1 was hydrolyzed to the acid according to the procedure described in Example 3.

Example 58

Synthesis of 1-(4'-{4-[6-(2-Cyano-phenyl)-pyridin-2-ylamino]-3-methyl-isoxazol-5-yl}-biphenyl-4-yl)-cyclopropanecarboxylic acid (Compound 50)

Step 1: 1-(4'-{4-[6-(2-Cyano-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-cyanophenylboronic acid.

Step 2: The ester from Step 1 was hydrolyzed to the acid according to the procedure described in Example 3.

Example 59

Synthesis of 1-(4'-{4-[6-(4-Methoxy-phenyl)-pyridin-2-ylamino]-3-methyl-isoxazol-5-yl}-biphenyl-4-yl)-cyclopropanecarboxylic acid (Compound 51)

Step 1: 1-(4'-{4-[6-(4-Methoxy-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 4-methoxyphenylboronic acid.

Step 2: The ester from Step 1 was hydrolyzed to the acid according to the procedure described in Example 3.

Example 60

Synthesis of 1-(4'-{4-[6-(3-Fluoro-phenyl)-pyridin-2-ylamino]-3-methyl-isoxazol-5-yl}-biphenyl-4-yl)-cyclopropanecarboxylic acid (Compound 52)

Step 1: 1-(4'-{4-[6-(3-Fluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-fluorophenylboronic acid.

Step 2: The ester from Step 1 was hydrolyzed to the acid according to the procedure described in Example 3.

Example 61

Synthesis of 1-(4'-{4-[6-(2-Methoxy-phenyl)-pyridin-2-ylamino]-3-methyl-isoxazol-5-yl}-biphenyl-4-yl)-cyclopropanecarboxylic acid (Compound 53)

Step 1: 1-(4'-{4-[6-(2-Methoxy-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-[4'-(4-amino-3-methyl-isoxazol-5-yl)-biphenyl-4-yl]-cyclopropanecarboxylic acid ethyl ester and 3-(3-bromo-phenyl)-2-methoxy-pyridine.

Step 2: The ester from Step 1 was hydrolyzed to the acid according to the procedure described in Example 3.

Example 62

Synthesis of 1-(4'-{4-[6-(2-Fluoro-phenyl)-pyridin-2-ylamino]-3-methyl-isoxazol-5-yl}-biphenyl-4-yl)-cyclopropanecarboxylic acid (Compound 54)

Step 1: 1-(4'-{4-[6-(2-Fluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-(2-fluoro-phenyl)-4,4,5,5-tetramethyl-[1,3,2]dioxaborolane.

Step 2: The ester from Step 1 was hydrolyzed to the acid according to the procedure described in Example 3.

Example 63

Synthesis of 1-(4'-{3-Methyl-4-[6-(2-trifluoromethyl-phenyl)-pyridin-2-ylamino]-isoxazol-5-yl}-biphenyl-4-yl)-cyclopropanecarboxylic acid (Compound 55)

Step 1: 1-(4'-{3-Methyl-4-[6-(2-trifluoromethyl-phenyl)-pyridin-2-ylamino]-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 4,4,5,5-tetramethyl-2-(2-trifluoromethyl-phenyl)-[1,3,2]dioxaborolane.

Step 2: The ester from Step 1 was hydrolyzed to the acid according to the procedure described in Example 3.

Example 64

Synthesis of 1-(4'-{3-Methyl-4-[(2-phenyl-thiazol-5-ylmethyl)-amino]-isoxazol-5-yl}-biphenyl-4-yl)-cyclopropanecarboxylic acid (Compound 56)

Step 1: 1-(4'-{3-Methyl-4-[(2-phenyl-thiazol-5-ylmethyl)-amino]-isoxazol-5-yl}-biphenyl-4-yl)-cyclopropanecarboxylic acid ethyl ester: Prepared according to the procedure described in Example 1, Step 12, using 1-[4'-(4-amino-3-methyl-isoxazol-5-yl)-biphenyl-4-yl]-cyclopropanecarboxylic acid ethyl ester and 2-phenyl-thiazole-5-carbaldehyde.

Step 2: The ester from Step 1 was hydrolyzed to the acid according to the procedure described in Example 3.

Example 65

Synthesis of 1-{4'-[3-Methyl-4-(2'-trifluoromethyl-biphenyl-3-ylamino)-isoxazol-5-yl]-biphenyl-4-yl}-cyclopropanecarboxylic acid (Compound 57)

Step 1: 1-{4'-[4-(3-Bromo-phenylamino)-3-methyl-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 1,3-dibromo-benzene.

Step 2: 1-{4'-[3-Methyl-4-(2'-trifluoromethyl-biphenyl-3-ylamino)-isoxazol-5-yl]-biphenyl-4-yl}-cyclopropanecarboxylic acid ethyl ester: Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and 2-(trifluoromethyl)phenylboronic acid.

Step 3: The ester from Step 2 was hydrolyzed to the acid according to the procedure described in Example 3.

Example 66

Synthesis of 1-{4'-[3-Methyl-4-(5-phenyl-pyridin-3-ylamino)-isoxazol-5-yl]-biphenyl-4-yl}-cyclopropanecarboxylic acid (Compound 58)

Step 1: 3-Bromo-5-phenyl-pyridine: Prepared according to the procedure described in Example 1, Step 10, using 3,5-dibromo-pyridine and phenylboronic acid.

Step 2: 1-{4'-[3-Methyl-4-(5-phenyl-pyridin-3-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-phenyl-pyridine.

Step 3: The ester from Step 2 was hydrolyzed to the acid according to the procedure described in Example 3.

Example 67

Synthesis of 1-(4'-{4-[5-(3-Fluoro-phenyl)-pyridin-3-ylamino]-3-methyl-isoxazol-5-yl}-biphenyl-4-yl)-cyclopropanecarboxylic acid (Compound 59)

Step 1: 3-Bromo-5-(3-fluoro-phenyl)-pyridine: Prepared according to the procedure described in Example 1, Step 10, using 3,5-dibromo-pyridine and 3-fluorophenylboronic acid.

Step 2: 1-(4'-{4-[5-(3-Fluoro-phenyl)-pyridin-3-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(3-fluoro-phenyl)-pyridine.

Step 3: The ester from Step 2 was hydrolyzed to the acid according to the procedure described in Example 3.

Example 68

Synthesis of 1-(4'-{4-[6-(2-Chloro-phenyl)-pyridin-2-ylamino]-3-methyl-isoxazol-5-yl}-biphenyl-4-yl)-cyclopropanecarboxylic acid (Compound 60)

Step 1: 1-(4'-{4-[6-(2-Chloro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-chlorophenylboronic acid.

Step 2: The ester from Step 1 was hydrolyzed to the acid according to the procedure described in Example 3.

Example 69

Synthesis of 1-(4'-{4-[Hydroxy-(6-phenyl-pyridin-2-yl)-methyl]-3-methyl-isoxazol-5-yl}-biphenyl-4-yl)-cyclopropanecarboxylic acid (Compound 61)

Step 1: 1-(4'-{4-[Hydroxy-(6-phenyl-pyridin-2-yl)-methyl]-3-methyl-isoxazol-5-yl}-biphenyl-4-yl)-cyclopropanecarboxylic acid ethyl ester: Prepared according to the procedure described in Example 34, Step 3, using 1-[4'-(4-formyl-3-methyl-isoxazol-5-yl)-biphenyl-4-yl]-cyclopropanecarboxylic acid ethyl ester and 2-bromo-6-phenyl-pyridine.

Step 2: The ester from Step 1 was hydrolyzed to the acid according to the procedure described in Example 3.

Example 70

Synthesis of 1-{4'-[3-Methyl-4-(2-phenyl-pyridin-4-ylamino)-isoxazol-5-yl]-biphenyl-4-yl}-cyclopropanecarboxylic acid (Compound 62)

Step 1: 1-{4'-[3-Methyl-4-(2-phenyl-pyridin-4-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 4-bromo-2-phenyl-pyridine.

Step 2: The ester from Step 1 was hydrolyzed to the acid according to the procedure described in Example 3.

Example 71

Synthesis of 1-(4'-{4-[2-(3-Fluoro-phenyl)-pyridin-4-ylamino]-3-methyl-isoxazol-5-yl}-biphenyl-4-yl)-cyclopropanecarboxylic acid (Compound 63)

Step 1: 1-(4'-{4-[2-(3-Fluoro-phenyl)-pyridin-4-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 4-bromo-2-(3-fluoro-phenyl)-pyridine.

Step 2: The ester from Step 1 was hydrolyzed to the acid according to the procedure described in Example 3.

Example 72

Synthesis of 1-(4'-{4-[5-(2-Chloro-phenyl)-pyridin-3-ylamino]-3-methyl-isoxazol-5-yl}-biphenyl-4-yl)-cyclopropanecarboxylic acid (Compound 64)

Step 1: 3-Bromo-5-(2-chloro-phenyl)-pyridine: Prepared according to the procedure described in Example 1, Step 10, using 3,5-dibromo-pyridine and 2-chlorophenylboronic acid.

Step 2: 1-(4'-{4-[5-(2-Chloro-phenyl)-pyridin-3-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(2-chloro-phenyl)-pyridine.

Step 3: The ester from Step 2 was hydrolyzed to the acid according to the procedure described in Example 3.

Example 73

Synthesis of 1-(4'-{4-[2-(2-Chloro-phenyl)-pyridin-4-ylamino]-3-methyl-isoxazol-5-yl}-biphenyl-4-yl)-cyclopropanecarboxylic acid (Compound 65)

Step 1: 4-Bromo-2-(2-chloro-phenyl)-pyridine: Prepared according to the procedure described in Example 1, Step 10, using 2,4-dibromo-pyridine and 2-chlorophenylboronic acid.
Step 2: 1-(4'-{4-[2-(2-Chloro-phenyl)-pyridin-4-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 4-bromo-2-(2-chloro-phenyl)-pyridine.
Step 3: The ester from Step 2 was hydrolyzed to the acid according to the procedure described in Example 3.

Example 74

Synthesis of 1-{4'-[3-Methyl-4-(4-phenyl-pyrimidin-2-ylamino)-isoxazol-5-yl]-biphenyl-4-yl}-cyclopropanecarboxylic acid (Compound 66)

Step 1: 1-{4'-[3-Methyl-4-(4-phenyl-pyrimidin-2-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-4-phenyl-pyrimidine.
Step 2: The ester from Step 1 was hydrolyzed to the acid according to the procedure described in Example 3.

Example 75

Synthesis of 1-{4'-[3-Methyl-4-(4-phenyl-pyridin-2-ylamino)-isoxazol-5-yl]-biphenyl-4-yl}-cyclopropanecarboxylic acid (Compound 67)

Step 1: 1-{4'-[3-Methyl-4-(4-phenyl-pyridin-2-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 2-bromo-4-phenyl-pyridine.
Step 2: The ester from Step 1 was hydrolyzed to the acid according to the procedure described in Example 3.

Example 76

Synthesis of 1-(4'-{3-Methyl-4-[5-(3-trifluoromethyl-phenyl)-pyridin-3-ylamino]-isoxazol-5-yl}-biphenyl-4-yl)-cyclopropanecarboxylic acid (Compound 68)

Step 1: 3-Bromo-5-(3-trifluoromethyl-phenyl)-pyridine: Prepared according to the procedure described in Example 1, Step 10, using 3,5-dibromo-pyridine and 3-(trifluoromethyl)-phenylboronic acid.
Step 2: 1-(4'-{3-Methyl-4-[5-(3-trifluoromethyl-phenyl)-pyridin-3-ylamino]-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(3-trifluoromethyl-phenyl)-pyridine.
Step 3: The ester from Step 2 was hydrolyzed to the acid according to the procedure described in Example 3.

Example 77

Synthesis of 1-(4'-{3-Methyl-4-[5-(4-trifluoromethyl-phenyl)-pyridin-3-ylamino]-isoxazol-5-yl}-biphenyl-4-yl)-cyclopropanecarboxylic acid (Compound 69)

Step 1: 3-Bromo-5-(4-trifluoromethyl-phenyl)-pyridine: Prepared according to the procedure described in Example 1, Step 10, using 3,5-dibromo-pyridine and 4-(trifluoromethyl)-phenylboronic acid.
Step 2: 1-(4'-{3-Methyl-4-[5-(4-trifluoromethyl-phenyl)-pyridin-3-ylamino]-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(4-trifluoromethyl-phenyl)-pyridine.
Step 3: The ester from Step 2 was hydrolyzed to the acid according to the procedure described in Example 3.

Example 78

Synthesis of 1-{4'-[3-Methyl-4-(6-phenyl-pyridin-2-ylamino)-isoxazol-5-yl]-biphenyl-4-yl}-cyclobutanecarboxylic acid (Compound 70)

Step 1: 1-(4-Bromo-phenyl)-cyclobutanecarboxylic acid ethyl ester: Ethyl 4-bromophenyl acetate (2 g, 8.2 mmol) was dissolved in DMF (20 mL) and cooled to 0° C. under $N_2$ atmosphere. Sodium hydride (60% in mineral oil, 0.72 g, 18.1 mmol) was added and the reaction was allowed to warm to room temperature. After 10 minutes the ice bath was replaced and 1,3-dibromopropane (0.92 mL, 9.0 mmol) was added, and the reaction was again allowed to warm to room temperature. After 30 minutes the reaction was submitted to aqueous workup and purified on silica gel to give the title compound.
Step 2: 1-[4-(4,4,5,5-Tetramethyl-[1,3,2]dioxaborolan-2-yl)-phenyl]-cyclobutanecarboxylic acid ethyl ester: Prepared according to the procedure described in Example 1, Step 9, using 1-(4-bromo-phenyl)-cyclobutanecarboxylic acid ethyl ester and bis(pinacolato)diboron.
Step 3: 1-[4'-(4-tert-Butoxycarbonylamino-3-methyl-isoxazol-5-yl)-biphenyl-4-yl]-cyclobutanecarboxylic acid ethyl ester: Prepared according to the procedure described in Example 1, Step 10, using [5-(4-bromo-phenyl)-3-methyl-isoxazol-4-yl]-carbamic acid tert-butyl ester and 1-[4-(4,4,5,5-tetramethyl-[1,3,2]dioxaborolan-2-yl)-phenyl]-cyclobutanecarboxylic acid ethyl ester. Additionally, (1,1'-bis(diphenylphosphino)ferrocene)-dichloropalladium(II) was used as the catalyst in place of tetrakis(triphenylphosphine)palladium(0).
Step 4: 1-[4'-(4-Amino-3-methyl-isoxazol-5-yl)-biphenyl-4-yl]-cyclobutanecarboxylic acid ethyl ester: Prepared according to the procedure described in Example 1, Step 9, using 1-[4'-(4-tert-butoxycarbonylamino-3-methyl-isoxazol-5-yl)-biphenyl-4-yl]-cyclobutanecarboxylic acid ethyl ester.

Step 5: 1-{4'-[3-Methyl-4-(6-phenyl-pyridin-2-ylamino)-isoxazol-5-yl]-biphenyl-4-yl}-cyclobutanecarboxylic acid ethyl ester: Prepared according to the procedure described in Example 41, Step 2, using 1-[4'-(4-amino-3-methyl-isoxazol-5-yl)-biphenyl-4-yl]-cyclobutanecarboxylic acid ethyl ester and 2-bromo-6-phenyl-pyridine.

Step 6: The ester from Step 5 was hydrolyzed to the acid according to the procedure described in Example 3.

Example 79

Synthesis of 1-(4'-{4-[Hydroxy-(5-phenyl-pyridin-3-yl)-methyl]-3-methyl-isoxazol-5-yl}-biphenyl-4-yl)-cyclopropanecarboxylic acid (Compound 71)

Step 1: 1-(4'-{4-[Hydroxy-(5-phenyl-pyridin-3-yl)-methyl]-3-methyl-isoxazol-5-yl}-biphenyl-4-yl)-cyclopropanecarboxylic acid ethyl ester: Prepared according to the procedure described in Example 19, Step 1, using 1-[4'-(4-formyl-3-methyl-isoxazol-5-yl)-biphenyl-4-yl]-cyclopropanecarboxylic acid ethyl ester and 3-bromo-5-phenyl-pyridine.

Step 2: The ester from Step 1 was hydrolyzed to the acid according to the procedure described in Example 3.

Example 80

Synthesis of 1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid (Compound 72)

Step 1: 1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid ethyl ester: Prepared according to the procedure described in Example 19, Step 1, using 1-[4'-(4-formyl-3-methyl-isoxazol-5-yl)-biphenyl-4-yl]-cyclopropanecarboxylic acid ethyl ester and 3-bromo-5-(3-trifluoromethyl-phenyl)-pyridine.

Step 2: The ester from Step 1 was hydrolyzed to the acid according to the procedure described in Example 3.

Example 81

Synthesis of 1-{4'-[3-Methyl-4-(6-phenylethynyl-pyridin-2-ylamino)-isoxazol-5-yl]-biphenyl-4-yl}-cyclopropanecarboxylic acid (Compound 73)

Step 1: 1-{4'-[3-Methyl-4-(6-phenylethynyl-pyridin-2-ylamino)-isoxazol-5-yl]-biphenyl-4-yl}-cyclopropanecarboxylic acid ethyl ester: 1-{4'-[4-(6-Bromo-pyridin-2-ylamino)-3-methyl-isoxazol-5-yl]-biphenyl-4-yl}-cyclopropanecarboxylic acid ethyl ester (0.200 g, 0.386 mmol) was dissolved in toluene along with phenylacetylene (0.051 mL, 0.46 mmol), copper(I) iodide (0.367 g, 1.93 mmol), triethylamine (0.269 mL, 1.93 mmol) and bis(triphenylphosphine)palladium(II) dichloride (0.032 g, 0.039 mmol). The reaction was heated to 40° C. for 3 days then cooled, diluted with EtOAc and filtered through a plug of silica gel. The crude material was purified on silica gel to yield the title compound.

Step 2: The ester from Step 1 was hydrolyzed to the acid according to the procedure described in Example 3.

Example 82

Synthesis of 1-(4'-{4-[6-(3-Cyano-phenyl)-pyridin-2-ylamino]-3-methyl-isoxazol-5-yl}-biphenyl-4-yl)-cyclopropanecarboxylic acid (Compound 74)

Step 1: 1-(4'-{4-[6-(3-Cyano-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-cyano-phenylboronic acid.

Step 2: The ester from Step 1 was hydrolyzed to the acid according to the procedure described in Example 3.

Example 83

Synthesis of 1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid (Compound 75)

Step 1: 1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 5-fluoro-2-methoxy-phenylboronic acid.

Step 2: The ester from Step 1 was hydrolyzed to the acid according to the procedure described in Example 3.

Example 84

Synthesis of 1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid (Compound 76)

Step 1: 1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-chloro-5-fluorophenylboronic acid.

Step 2: The ester from Step 1 was hydrolyzed to the acid according to the procedure described in Example 3.

Example 85

Synthesis of 1-(4'-{4-[6-(2,5-Difluoro-phenyl)-pyridin-2-ylamino]-3-methyl-isoxazol-5-yl}-biphenyl-4-yl)-cyclopropanecarboxylic acid (Compound 77)

Step 1: 1-(4'-{4-[6-(2,5-Difluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2,5-difluoro-phenylboronic acid.

Step 2: The ester from Step 1 was hydrolyzed to the acid according to the procedure described in Example 3.

Example 86

Synthesis of 1-(4'-{4-[6-(2,6-Dichloro-phenyl)-pyridin-2-ylamino]-3-methyl-isoxazol-5-yl}-biphenyl-4-yl)-cyclopropanecarboxylic acid (Compound 78)

Step 1: 1-(4'-{4-[6-(2,6-Dichloro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2,6-dichloro-phenylboronic acid. Additionally, (1,1'-bis(diphenylphosphino)ferrocene)-dichloropalladium(II) was used as the catalyst in place of tetrakis(triphenylphosphine)palladium(0).
Step 2: The ester from Step 1 was hydrolyzed to the acid according to the procedure described in Example 3.

Example 87

Synthesis of 1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid (Compound 79)

Step 1: 1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-5-fluoro-phenylboronic acid. Additionally, (1,1'-bis(diphenylphosphino)ferrocene)-dichloropalladium(II) was used as the catalyst in place of tetrakis(triphenylphosphine)palladium(0).
Step 2: The ester from Step 1 was hydrolyzed to the acid according to the procedure described in Example 3.

Example 88

Synthesis of 1-(4'-{4-[6-(2,3-Difluoro-phenyl)-pyridin-2-ylamino]-3-methyl-isoxazol-5-yl}-biphenyl-4-yl)-cyclopropanecarboxylic acid (Compound 80)

Step 1: 1-(4'-{4-[6-(2,3-Difluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2,3-difluoro-phenylboronic acid. Additionally, (1,1'-bis(diphenylphosphino)ferrocene)-dichloropalladium(II) was used as the catalyst in place of tetrakis(triphenylphosphine)palladium(0).
Step 2: The ester from Step 1 was hydrolyzed to the acid according to the procedure described in Example 3.

Example 89

Synthesis of 1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid (Compound 81)

Step 1: 1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-3-fluoro-phenylboronic acid. (1,1'-Bis(diphenylphosphino)ferrocene)-dichloropalladium(II) was used in place of tetrakis(triphenylphosphine)palladium(0).
Step 2: The ester from Step 1 was hydrolyzed to the acid according to the procedure described in Example 3.

Example 90

Synthesis of 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid (Compound 82)

Step 1: 3-Bromo-5-(2-chloro-3-fluoro-phenyl)-pyridine: Prepared according to the procedure described in Example 1, Step 10, using 3,5-dibromo-pyridine and 2-chloro-3-fluoro-phenylboronic acid. (1,1'-bis(diphenylphosphino)ferrocene)-dichloropalladium(II) was used in place of tetrakis(triphenylphosphine)palladium(0).
Step 2: 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(2-chloro-3-fluoro-phenyl)-pyridine.
Step 3: The ester from Step 2 was hydrolyzed to the acid according to the procedure described in Example 3.

Example 91

Synthesis of 1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid (Compound 83)

Step 1: 1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-fluoro-2-methyl-phenylboronic acid. Additionally, (1,1'-bis(diphenylphosphino)ferrocene)-dichloropalladium(II) was used as the catalyst in place of tetrakis(triphenylphosphine)palladium(0).
Step 2: The ester from Step 1 was hydrolyzed to the acid according to the procedure described in Example 3.

Example 92

Synthesis of 1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid (Compound 84)

Step 1: 1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-3-(trifluoromethyl)phenylboronic acid. Additionally, (1,1'-bis(diphenylphosphino)ferrocene)-dichloropalladium(II) was used as the catalyst in place of tetrakis(triphenylphosphine)palladium(0).

Step 2: The ester from Step 1 was hydrolyzed to the acid according to the procedure described in Example 3.

Example 93

Synthesis of N-[1-(4'-{4-[(1-Benzyl-1H-[1,2,3]triazol-4-yl)-hydroxy-methyl]-3-methyl-isoxazol-5-yl}-biphenyl-4-yl)-cyclopropanecarbonyl]-methanesulfonamide (Enantiomer B) (Compound 91)

A solution of 1-(4'-{4-[(1-benzyl-1H-[1,2,3]triazol-4-yl)-hydroxy-methyl]-3-methyl-isoxazol-5-yl}-biphenyl-4-yl)-cyclopropanecarboxylic acid (Enantiomer B) (0.100 g, 0.197 mmol), carbonyldiimidazole (0.080 g, 0.5 mmol), N,N-dimethylamino pyridine (0.002 g, 0.02 mmol) in THF (2 mL) was stirred at room temperature overnight. Added MeSO$_2$NH$_2$ (0.050 g, 0.5 mmol) and DBU (0.100 mL, 0.65 mmol) and the mixture heated to 100° C. in a capped vial for 4.5 hours. The solution was poured into sat. aqueous NH$_4$Cl, then water and EtOAc was added. The organic layer was separated, dried (Na$_2$SO$_4$), concentrated and the resulting reside purified by preparative HPLC to yield the title compound.

Example 94

Synthesis of N-[1-(4'-{4-[(5-Benzyl-[1,3,4]oxadiazol-2-yl)-hydroxy-methyl]-3-methyl-isoxazol-5-yl}-biphenyl-4-yl)-cyclopropanecarbonyl]-methanesulfonamide (Enantiomer A) (Compound 92)

Step 1: N-[1-(4-Bromo-phenyl)-cyclopropanecarbonyl]-methanesulfonamide: 1-(4-Bromo-phenyl)-cyclopropanecarboxylic acid (22 g, 91.3 mmol) and SOCl$_2$ (13.6 mL, 183 mmol) in CH$_2$Cl$_2$ were heated together for 1.5 hours then evaporated to afford a dark oil. This oil was added via syringe over 30 minutes to a mixture of MeSO$_2$NH$_2$ (19 g, 200 mmol) in THF (250 mL) that was pre-treated at room temperature with NaH (60% in oil; 8.0 g, 200 mmol) for 1.5 hours. After a further 20 minutes, the mixture was poured into water, acidified and extracted with CH$_2$Cl$_2$, washed with water (2×) and evaporated to ~100 mL. Hexane (300 mL) was added and the product collected by filtration to yield the title compound (25 g).

Step 2: N-{1-[4-(4,4,5,5-Tetramethyl-[1,3,2]dioxaborolan-2-yl)-phenyl]-cyclopropanecarbonyl}-methanesulfonamide: N-[1-(4-Bromo-phenyl)-cyclopropanecarbonyl]-methanesulfonamide (22 g, 69 mmol), bis(pinacolato)diborane (21.1 g, 83 mmol), KOAc (21.6 g, 220 mmol) in dioxane (300 mL) were degassed with N$_2$ for 30 minutes and then (1,1'-bis(diphenylphosphino)ferrocene)-dichloropalladium(II) (1.0 g, 1.4 mmol) was added. The mixture was heated at reflux for 2 hours then at 70° C. for 16 hours. Then solution was poured into EtOAc/H$_2$O, acidified and the organic layer concentrated to give the boronate which was used in the next step without further purification.

Step 3: N-[1-(4'-{4-[(5-Benzyl-[1,3,4]oxadiazol-2-yl)-hydroxy-methyl]-3-methyl-isoxazol-5-yl}-biphenyl-4-yl)-cyclopropanecarbonyl]-methanesulfonamide (Enantiomer A): A solution of N-{1-[4-(4,4,5,5-tetramethyl-[1,3,2]dioxaborolan-2-yl)-phenyl]-cyclopropanecarbonyl}-methanesulfonamide (0.045 g, 0.124 mmol), 5-benzyl-[1,3,4]oxadiazol-2-yl)-[5-(4-bromo-phenyl)-3-methyl-isoxazol-4-yl]-methanol (Enantiomer A) (0.053 g, 0.124 mmol), NaHCO$_3$ (0.031 g, 0.372 mmol), DME (1.5 mL) and H$_2$O (1 mL) was degassed by bubbling with N$_2$ for 10 minutes. Tetrakis(triphenylphosphine)palladium(0) (0.007 g, 0.006 mmol) was added and the sealed reaction vial was stirred at 80° C. for 16 hours. The mixture was poured into EtOAc/H$_2$O, washed with 1N HCl then aqueous Na$_2$SO$_4$ and concentrated. The resulting reside purified by preparative HPLC to yield the title compound.

Example 95

Synthesis of N-{1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarbonyl}-methanesulfonamide (Compound 93)

Step 1: Prepared according to the procedure described in Example 94, Step 3, using [5-(4-bromo-phenyl)-3-methyl-isoxazol-4-yl]-[1-(3-trifluoromethyl-benzyl)-1H-[1,2,3]triazol-4-yl]-methanol and N-{1-[4-(4,4,5,5-tetramethyl-[1,3,2]dioxaborolan-2-yl)-phenyl]-cyclopropanecarbonyl}-methanesulfonamide.

Example 96

Synthesis of N-(1-{4'-[3-Methyl-4-(5-phenyl-[1,3,4]oxadiazol-2-ylamino)-isoxazol-5-yl]-biphenyl-4-yl}-cyclopropanecarbonyl)-methanesulfonamide (Compound 94)

Step 1: Prepared according to the procedure described in Example 94, Step 3, using [5-(4-bromo-phenyl)-3-methyl-isoxazol-4-yl]-(5-phenyl-[1,3,4]oxadiazol-2-yl)-amine and N-{1-[4-(4,4,5,5-tetramethyl-[1,3,2]dioxaborolan-2-yl)-phenyl]-cyclopropanecarbonyl}-methanesulfonamide.

Example 97

Synthesis of N-(1-{4'-[4-(6-Benzyl-pyridin-2-ylamino)-3-methyl-isoxazol-5-yl]-biphenyl-4-yl}-cyclopropanecarbonyl)-methanesulfonamide (Compound 95)

Step 1: N-(1-{4'-[4-(6-Benzyl-pyridin-2-ylamino)-3-methyl-isoxazol-5-yl]-biphenyl-4-yl}-cyclopropanecarbonyl)-methanesulfonamide: 1-{4'-[4-(6-benzyl-pyridin-2-ylamino)-3-methyl-isoxazol-5-yl]-biphenyl-4-yl}-cyclopropanecarboxylic acid (sodium salt; 0.050 g, 0.083 mmol), carbonyldiimidazole (0.0676 g, 0.417 mmol), MeSO$_2$NH$_2$ (0.0789 g, 0.83 mmol) and DBU (0.0248 mL, 0.166 mmol) were combined in THF (1 mL) and the mixture was heated to 70° C. in a capped vial for 25 hours. The mixture was purified by preparative HPLC to yield the title compound.

Example 98

Synthesis of N-(1-{4'-[3-Methyl-4-(6-phenyl-pyridin-2-ylamino)-isoxazol-5-yl]-biphenyl-4-yl}-cyclopropanecarbonyl)-methanesulfonamide (Compound 96)

Step 1: {5-[4'-(1-Methanesulfonylaminocarbonyl-cyclopropyl)-biphenyl-4-yl]-3-methyl-isoxazol-4-yl}-carbamic acid tert-butyl ester: Prepared according to the procedure described in Example 94, Step 3, using [5-(4-Bromo-phenyl)-3-methyl-isoxazol-4-yl]-carbamic acid tert-butyl ester and N-{1-[4-(4,4,5,5-tetramethyl-[1,3,2]dioxaborolan-2-yl)-phenyl]-cyclopropanecarbonyl}-methanesulfonamide.

Step 2: N-{1-[4'-(4-Amino-3-methyl-isoxazol-5-yl)-biphenyl-4-yl]-cyclopropanecarbonyl}-methanesulfonamide: {5-[4'-(1-Methanesulfonylaminocarbonyl-cyclopropyl)-biphenyl-4-yl]-3-methyl-isoxazol-4-yl}-carbamic acid tert-butyl ester (0.25 g, 0.49 mmol)) in $CH_2Cl_2$ (2 mL) and TFA (2 mL) was stirred overnight then poured into EtOAc/$NaHCO_3$ (aq). The organic layer was concentrated to yield the title compound that was used directly in the next step.

Step 3: N-(1-{4'-[3-Methyl-4-(6-phenyl-pyridin-2-ylamino)-isoxazol-5-yl]-biphenyl-4-yl}-cyclopropanecarbonyl)-methanesulfonamide: N-{1-[4'-(4-Amino-3-methyl-isoxazol-5-yl)-biphenyl-4-yl]-cyclopropanecarbonyl}-methanesulfonamide (0.103 g, 0.25 mmol), 2-bromo-6-phenylpyridine (0.059 g, 0.25 mmol), potassium carbonate (0.243 g, 0.75 mmol), and BINAP (15 mg, 0.025 mmol) were combined in THF (10 mL) and the solution was degassed with $N_2$ for 10 minutes. Palladium(II)acetate (0.003 g, 0.0125 mmol) was added and degassing was continued for 10 minutes. The reaction mixture was sealed and heated at 65° C. overnight then poured into EtOAc/water. The organic layer was concentrated and purified by silica gel chromatography to give the title compound.

Example 99

1-{4'-[4-(2'-Dimethylaminomethyl-biphenyl-3-ylamino)-3-methyl-isoxazol-5-yl]-biphenyl-4-yl}-cyclopropanecarboxylic acid (Compound 85)

Step 1: 1-{4'-[4-(2'-Dimethylaminomethyl-biphenyl-3-ylamino)-3-methyl-isoxazol-5-yl]-biphenyl-4-yl}-cyclopropanecarboxylic acid ethyl ester: Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and 2-(N,N-dimethylaminomethyl)-phenylboronic acid. (1,1'-Bis(diphenylphosphino)ferrocene)-dichloropalladium(II) was used in place of tetrakis(triphenylphosphine)palladium(0).

Step 2: The ester from Step 1 was hydrolyzed to the acid according to the procedure described in Example 3.

Example 100

Synthesis of 1-(4'-{4-[6-(2,3-Dichloro-phenyl)-pyridin-2-ylamino]-3-methyl-isoxazol-5-yl}-biphenyl-4-yl)-cyclopropanecarboxylic acid (Compound 86)

Step 1: 1-(4'-{4-[6-(2,3-Dichloro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2,3-dichlorophenylboronic acid. (1,1'-bis(diphenylphosphino)ferrocene)-dichloropalladium(II) was used in place of tetrakis(triphenylphosphine)palladium(0).

Step 2: The ester from Step 1 was hydrolyzed to the acid according to the procedure described in Example 3.

Example 101

Synthesis of 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid (Compound 87)

Step 1: 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-fluoro-2-methoxyphenylboronic acid. (1,1'-Bis(diphenylphosphino)ferrocene)-dichloropalladium(II) was used in place of tetrakis(triphenylphosphine)palladium(0).

Step 2: The ester from Step 1 was hydrolyzed to the acid according to the procedure described in Example 3.

Example 102

Synthesis of 1-(4'-{4-[5-(3-Chloro-phenyl)-pyridin-3-ylamino]-3-methyl-isoxazol-5-yl}-biphenyl-4-yl)-cyclopropanecarboxylic acid (Compound 88)

Step 1: 3-Bromo-5-(3-chloro-phenyl)-pyridine: Prepared according to the procedure described in Example 1, Step 10, using the following starting materials: 3,5-dibromo-pyridine and 3-chlorophenylboronic acid.

Step 2: 1-(4'-{4-[5-(3-Chloro-phenyl)-pyridin-3-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(3-chloro-phenyl)-pyridine.

Step 3: The ester from Step 2 was hydrolyzed to the acid according to the procedure described in Example 3.

Example 103

Synthesis of 1-(4'-{4-[5-(2,5-Difluoro-phenyl)-pyridin-3-ylamino]-3-methyl-isoxazol-5-yl}-biphenyl-4-yl)-cyclopropanecarboxylic acid (Compound 89)

Step 1: 3-Bromo-5-(2,5-difluoro-phenyl)-pyridine: Prepared according to the procedure described in Example 41, Step 1, using 3,5-dibromo-pyridine and 2,5-difluorophenylboronic acid.

Step 2: 1-(4'-{4-[5-(2,5-Difluoro-phenyl)-pyridin-3-ylamino]-3-methyl-isoxazol-5-yl}-biphenyl-4-yl)-cyclopropanecarboxylic acid ethyl ester: Prepared according to the procedure described in Example 41, Step 2, using 1-[4'-(4-amino-3-methyl-isoxazol-5-yl)-biphenyl-4-yl]-cyclopropanecarboxylic acid ethyl ester and 3-bromo-5-(2,5-difluoro-phenyl)-pyridine.

Step 3: The ester from Step 2 was hydrolyzed to the acid according to the procedure described in Example 3.

Example 104

Synthesis of 1-(4'-{4-[6-(3-Chloro-phenyl)-pyridin-2-ylamino]-3-methyl-isoxazol-5-yl}-biphenyl-4-yl)-cyclopropanecarboxylic acid (Compound 90)

Step 1: 1-(4'-{4-[6-(3-Chloro-phenyl)-pyridin-2-ylamino]-3-methyl-isoxazol-5-yl}-biphenyl-4-yl)-cyclopropanecarboxylic acid ethyl ester: Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-chlorophenylboronic acid. (1,1'-bis(diphenylphosphino)ferrocene)-dichloropalladium(II) was used in place of tetrakis(triphenylphosphine)palladium(0).

Step 2: The ester from Step 1 was hydrolyzed to the acid according to the procedure described in Example 3.

Example 105

Synthesis of 1-{4'-[3-Ethyl-4-(6-phenyl-pyridin-2-ylamino)-isoxazol-5-yl]-biphenyl-4-yl}-cyclopropanecarboxylic acid (Compound 97)

Step 1: 3-Methylamino-pent-2-enoic acid methyl ester: Prepared according to the procedure described in Example 1, Step 1, using the following starting materials: 3-oxo-pentanoic acid methyl ester and methylamine.

Step 2: 2-(4-Bromo-benzoyl)-3-oxo-pentanoic acid methyl ester: Prepared according to the procedure described in Example 1, Step 2, using the following starting materials: 3-methylamino-pent-2-enoic acid methyl ester and 4-bromobenzoyl chloride.

Step 3: 5-(4-Bromo-phenyl)-3-ethyl-isoxazole-4-carboxylic acid methyl ester: Prepared according to the procedure described in Example 1, Step 3, using the following starting material: 2-(4-bromo-benzoyl)-3-oxo-pentanoic acid methyl ester.

Step 4: 5-(4-Bromo-phenyl)-3-ethyl-isoxazole-4-carboxylic acid: Prepared according to the procedure described in Example 1, Step 4, using the following starting material: 5-(4-bromo-phenyl)-3-ethyl-isoxazole-4-carboxylic acid methyl ester.

Step 5: [5-(4-Bromo-phenyl)-3-ethyl-isoxazol-4-yl]-carbamic acid tert-butyl ester: Prepared according to the procedure described in Example 1, Step 5, using the following starting material: 5-(4-bromo-phenyl)-3-ethyl-isoxazole-4-carboxylic acid.

Step 6: 1-[4'-(4-tert-Butoxycarbonylamino-3-ethyl-isoxazol-5-yl)-biphenyl-4-yl]-cyclopropanecarboxylic acid ethyl ester: Prepared according to the procedure described in Example 1, Step 10, using the following starting materials: [5-(4-bromo-phenyl)-3-ethyl-isoxazol-4-yl]-carbamic acid tert-butyl ester and 1-[4-(4,4,5,5-tetramethyl-[1,3,2]dioxaborolan-2-yl)-phenyl]-cyclopropanecarboxylic acid ethyl ester. (1,1'-bis(diphenylphosphino)ferrocene)-dichloropalladium(II) was used in place of tetrakis(triphenylphosphine)palladium(0).

Step 7: 1-[4'-(4-Amino-3-ethyl-isoxazol-5-yl)-biphenyl-4-yl]-cyclopropanecarboxylic acid ethyl ester: Prepared according to the procedure described in Example 1, Step 11, using 1-[4'-(4-tert-butoxycarbonylamino-3-ethyl-isoxazol-5-yl)-biphenyl-4-yl]-cyclopropanecarboxylic acid ethyl ester.

Step 8: 1-{4'-[3-Ethyl-4-(6-phenyl-pyridin-2-ylamino)-isoxazol-5-yl]-biphenyl-4-yl}-cyclopropanecarboxylic acid ethyl ester: Prepared according to the procedure described in Example 41, Step 2, using 1-[4'-(4-amino-3-ethyl-isoxazol-5-yl)-biphenyl-4-yl]-cyclopropanecarboxylic acid ethyl ester and 2-bromo-6-phenyl-pyridine.

Step 9: The ester from Step 8 was hydrolyzed to the acid according to the procedure described in Example 3.

Example 106

Synthesis of 1-{4'-[3-Ethyl-4-(5-phenyl-[1,3,4]oxadiazol-2-ylamino)-isoxazol-5-yl]-biphenyl-4-yl}-cyclopropanecarboxylic acid (Compound 98)

Step 1: [5-(4-Bromo-phenyl)-3-ethyl-isoxazol-4-yl]-(5-phenyl-[1,3,4]oxadiazol-2-yl)-amine: Prepared according to the procedure described in Example 51, Step 1, using 5-(4-bromo-phenyl)-3-ethyl-isoxazole-4-carboxylic acid and benzoic acid hydrazide.

Step 2: 1-{4'-[3-Ethyl-4-(5-phenyl-[1,3,4]oxadiazol-2-ylamino)-isoxazol-5-yl]-biphenyl-4-yl}-cyclopropanecarboxylic acid ethyl ester: Prepared according to the procedure described in Example 1, Step 10, using [5-(4-bromo-phenyl)-3-ethyl-isoxazol-4-yl]-(5-phenyl-[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester. (1,1'-bis(diphenylphosphino)ferrocene)-dichloropalladium(II) was used in place of tetrakis(triphenylphosphine)palladium(0).

Step 3: The ester from Step 2 was hydrolyzed to the acid according to the procedure described in Example 3.

In some embodiments, mass spectrometric data (mass spec. data) is obtained with a Shimadzu LCMS 2010A.

Example 107

Establishment of a CHO Cell Line Stably Expressing Human LPA$_1$

A 1.1 kb cDNA encoding the human LPA$_1$ receptor was cloned from human lung. Human lung RNA (Clontech Laboratories, Inc. USA) was reverse transcribed using the RETROSCRIPT® kit (Ambion, Inc.) and the full-length cDNA for human LPA$_1$ was obtained by PCR of the reverse transcription reaction. The nucleotide sequence of the cloned human LPA$_1$ was determined by sequencing and confirmed to be identical to the published human LPA$_1$ sequence (An et al., *Biochem. Biophys. Res. Commun.*, 231:619 (1997). The cDNA was cloned into the pcDNA5/FRT expression plasmid and transfected in CHO cells using Lipofectamine 2000 (Invitrogen Corp., USA). Clones stably expressing human LPA$_1$ were selected using hygromycin and identified as cells that show Ca-influx in response to LPA.

Example 108

Generation of Cells Transiently Expressing Human LPA$_2$

A vector containing the human LPA$_2$ receptor cDNA was obtained from the Missouri S&T cDNA Resource Center (www.cdna.org). The full-length cDNA fragment for human LPA$_2$ was obtained by PCR from the vector. The nucleotide sequence of the cloned human LPA$_2$ was determined by sequencing and confirmed to be identical to the published human LPA$_2$ sequence (NCBI accession number NM_004720). The cDNA was cloned into the pcDNA3.1 expression plasmid and transfected into B103 cells (Invitrogen Corp., USA) by seeding cells in a 96-well poly-D-lysine coated plate at 30,000-35,000 cells per well together with 0.2 µl Lipofectamine 2000 and 0.2 g of the LPA$_2$ expression vector. Cells were cultured overnight in complete media before being assayed for LPA-induced Ca-influx.

Example 109

Establishment of a CHO Cell Line Stably Expressing Human LPA$_3$

A vector containing the human LPA$_3$ receptor cDNA was obtained from the Missouri S&T cDNA Resource Center (www.cdna.org). The full-length cDNA fragment for human LPA$_3$ was obtained by PCR from the vector. The nucleotide sequence of the cloned human LPA$_3$ was determined by sequencing and confirmed to be identical to the published human LPA$_3$ sequence (NCBI accession number NM_012152). The cDNA was cloned into the pcDNA5/FRT expression plasmid and transfected in CHO cells using Lipofectamine 2000 (Invitrogen Corp., USA). Clones stably expressing human LPA$_3$ were selected using hygromycin and identified as cells that show Ca-influx in response to LPA.

Example 110

LPA1 and LPA3 Calcium Flux Assays

Human LPA$_1$ or LPA$_3$ expressing CHO cells are seeded at 20,000-45,000 cells per well in a 96-well poly-D-lysine coated plate one or two days before the assay. Prior to the assay, the cells are washed once with PBS and then cultured in serum-free media overnight. On the day of the assay, a calcium indicator dye (Calcium 4, Molecular Devices) in assay buffer (HBSS with Ca$^{2+}$ and Mg$^{2+}$ and containing 20 mM Hepes and 0.3% fatty-acid free human serum albumin) is added to each well and incubation continued for 1 hour at 37° C. 10 µl of test compounds in 2.5% DMSO are added to the cells and incubation continued at room temperature for 30 minutes. Cells are the stimulated by the addition of 10 nM LPA and intracellular Ca$^{2+}$ measured using the FLEXSTATION® 3 (Molecular Devices). IC$_{50}$s are determined using GraphPad prism analysis of drug titration curves.

Example 111

LPA2 Calcium Flux Assay

Following an overnight culture with Lipofectamine 2000 and the LPA$_2$ expression vector, the B103 cells are washed once with PBS then serum starved for 4 hours. A calcium indicator dye (Calcium 4, Molecular Devices) in assay buffer (HBSS with Ca and Mg$^2$ and containing 20 mM Hepes and 0.3% fatty-acid free human serum albumin) is added to each well and incubation continued for 1 hour at 37° C. 10l of test compounds in 2.5% DMSO are added to the cells and incubation continued at room temperature for 30 minutes. Cells are the stimulated by the addition of 10 nM LPA and intracellular Ca$^{2+}$ measured using the FLEXSTATION® 3 (Molecular Devices). IC$_{50}$s are determined using GraphPad Prism analysis of drug titration curves.

Example 112

GTPγS Binding Assay

The ability of a compound to inhibit binding of GTP to LPA$_1$ is assessed via a membrane GTPγS assay. CHO cells stably expressing the recombinant human LPA$_1$ receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~25 g per well) are incubated in 96-well plates with 0.1 nM [$^{35}$S]-GTPγS, 900 nM LPA, 5 M GDP, and test compound in Assay Buffer (50 mM Hepes, pH 7.4, 100 mM NaCl, 10 mM MgCl$_2$, 50 g/ml saponin and 0.2% fatty-acid free human serum albumin) for 30 minutes at 30° C. The reactions are terminated by rapid filtration through Whatman GF/B glass fiber filter plates. The filter plates are washed 3 times with 1 ml cold Wash Buffer (50 mM Hepes, 7.5, 100 mM NaCl and 10 mM MgCl$_2$) and dried. Scintillant is then added to the plates and the radioactivity retained on the filters is determined on a Packard TOPCOUNT® (Perkin Elmer). Specific binding is determined as total radioactive binding minus non-specific binding in the absence of the ligand (900 nM LPA). IC$_{50}$s were determined using GraphPad Prism analysis of drug titration curves.

Illustrative in vitro biological data for representative compounds of Formula (I) is presented in the Table below. Unless otherwise noted, all the compounds in Table 4 that were tested in this assay had IC$_{50}$ values of less than 50 M.

TABLE 4

| Compound No. | HLPA1 Ca Flux IC$_{50}$ |
|---|---|
| 1 | A |
| 2 | A |
| 3 | A |
| 4 | A |
| 5 | C |
| 6 | A |
| 7 | B |
| 8 | A |
| 9 | A |
| 10 | C |
| 11 | A |
| 12 | A |
| 13 | A |
| 14 | A |
| 15 | A |
| 16 | A |
| 17 | A |
| 18 | A |
| 19 | A |
| 20 | B |
| 21 | C |
| 22 | A |
| 23 | A |
| 24 | C |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | B |
| 38 | A |
| 39 | A |
| 40 | B |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |

TABLE 4-continued

| Compound No. | HLPA1 Ca Flux IC$_{50}$ |
|---|---|
| 62 | B |
| 63 | C |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | B |
| 85 | A |
| 86 | A |
| 87 | A |
| 88 | A |
| 89 | A |
| 90 | A |
| 91 | A |
| 92 | A |
| 93 | C |
| 94 | A |
| 95 | A |
| 96 | A |
| 97 | A |
| 98 | A |

A = less than 0.3 µM;
B = greater than 0.3 µM and less than 1 µM;
C = greater than 1 µM and less than 50 µM.

Example 113

LPA1 Chemotaxis Assay

Chemotaxis of the A2058 human melanoma cells was measured using the Neuroprobe CHEMOTX® System plates (8 m pore size, 5.7 mm diameter sites). The filter sites were coated with 0.001% fibronectin (Sigma) in 20 mM Hepes, pH 7.4 and allowed to dry. A2058 cells were serum-starved for 24 hours, then harvested with Cell Stripper and resuspended in DMEM containing 0.1% fatty-acid-free bovine serum albumin (BSA) to a concentration of $1 \times 10^6$/ml. Cells were mixed with an equal volume of test compound (2×) in DMEM containing 0.1% fatty-acid-free BSA and incubated at 37° C. for 15 minutes. LPA (100 nM in DMEM containing 0.1% fatty-acid-free BSA) or vehicle was added to each well of the lower chamber and 50 µl of the cell suspension/test compound mix was applied to the upper portion of the CHEMOTX® plate. Plates were incubated at 37° C. for three hours and then the cells removed from the upper portion by rinsing with PBS and scraping. The filter was dried then stained with HEMA 3® Staining System (Fisher Scientific). The absorbance of the filter was read at 590 nM and IC$_{50}$s were determined using SYMYX® Assay Explorer.

In this experiment, compounds 11, 13, 19, 23, 26, 27, 32, 33, 38, 39 41, 44, 45, 46, 47, 49, 52, 58, 59, 60, 64, 66, 67, 68, 75, 79, 81, 82, 83, 91, 92, and 95 inhibited LPA-driven chemotaxis (IC$_{50}$ less than 100 nM) of human A2058 melanoma cells.

Example 114

Bleomycin-Induced Lung Fibrosis Model in Mice

Female C57Bl/6 mice (Harlan, 25-30 g) are housed 4 per cage, given free access to food and water and allowed to acclimate for at least 7 days prior to test initiation. After the habituation phase, mice are lightly anesthetized with isoflurane (5% in 100% O$_2$) and administered with bleomycin sulfate (0.01-5 U/kg, Henry Schein) via intratracheal instillation (Cuzzocrea, S. et al., *Am. J. Physiol. Lung. Cell. Mol. Physiol.*, 292(5):L1095-L1104 (Epub Jan. 12, 2007)). Mice are returned to their cages and monitored daily for the duration of the experiment. Test compound or vehicle is delivered p.o., i.p. or s.c. daily. The route and frequency of dosing is based on previously determined pharmacokinetic properties. All animals are sacrificed using inhaled isoflurane 3, 7, 14, 21 or 28 days after bleomycin instillation. Following sacrifice, mice are intubated with a 20 gauge angiocatheter attached to a 1 ml syringe. Lungs are lavaged with saline to obtain bronchoalveolar lavage fluid (BALF) and then removed and fixed in 10% neutral buffered formalin for subsequent histopathological analysis. BALF is centrifuged for 10 min at 800×g to pellet the cells and the cell supernatant removed and frozen at −80° C. for subsequent protein analysis using the DC protein assay kit (Bio-Rad, Hercules, Calif.) and soluble collagen analysis using Sircol (Biocolor Ltd, UK). BALF is analyzed for concentrations of inflammatory, pro-fibrotic and tissue injury biomarkers including transforming growth factor 131, hyaluronic acid, tissue inhibitor of metalloproteinase-1, matrix matelloproteinase-7, connective tissue growth factor and lactate dehydrogenase activity, using commercially available ELISA. The cell pellet is resuspended in PBS. Total cell counts are then obtained using a HEMAVET® hematology system (Drew Scientific, Wayne, Pa.) and differential cells counts are determined using Shandon cytospin (Thermo Scientific, Waltham, Mass.). Lung tissue is stained using hematoxylin and eosin (H&E) and trichrome and lung fibrosis is determined by semiquantitative histopathological scoring (Ashcroft, T. et al., *J. Clin. Path.* 41(4):467-470 (1988)) using light microscopy (O$_1$× magnification) and quantitative, computer-assisted densitometry of collagen in lung tissue sections using light microscopy. The data are plotted using GraphPad Prism and statistical differences between groups determined.

In the acute setting (3 day), Compound 19 significantly reduced total protein and collagen concentrations in broncheoalveolar lavage fluid (BALF).

Example 115

Mouse Carbon Tetrachloride (CCl$_4$)-Induced Liver Fibrosis Model

Female C57BL/6 mice (Harlan, 20-25 g) housed 4/cage are given free access to food and water and allowed to acclimate for at least 7 days prior to test initiation. After the habituation phase, mice receive CCl$_4$ (1.0 ml/kg body weight) diluted in corn oil vehicle (100 L volume) via i.p. injection twice a week for 8 weeks. (Higazi, A. A. et al., *Clin. Exp. Immunol.*, 2008 April; 152(1):163-173, Epub Feb. 14, 2008). Control mice receive an equivalent volume of corn oil vehicle only. Test compound or vehicle is delivered p.o., i.p. or s.c. daily. At the end of the study (8 weeks after first i.p. injection of CCl$_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using GraphPad Prism and statistical differences between groups determined.

Example 116

Mouse Intravenous LPA-Induced Histamine Release

A mouse intravenous LPA-induced histamine release model is utilized to determine the in vivo potency of LPA$_1$ and LPA$_3$ receptor antagonists. Female CD-1 mice (weighing 25-35 grams) are administered compound (i.p., s.c. or p.o.) in a volume of 10 ml/kg 30 minutes to 24 hours prior to intravenous LPA challenge (300 g/mouse in 0.1% FAF BSA). Immediately following LPA challenge mice are placed into an enclosed PLEXIGLAS® chamber and exposed to an isoflurane for a period of 2 minutes. They are removed, decapitated and trunk blood collected into tubes containing EDTA. Blood is then centrifuged at 10,000×g for 10 minutes at 4° C. Histamine concentrations in the plasma are determined by EIA. Drug concentrations in plasma are determined by mass spectrometry. The dose to achieve 50% inhibition of blood histamine release is calculated by non-linear regression (GraphPad Prism) and plotted as the ED$_{50}$. The plasma concentration associated with this dose is plotted as the EC$_{50}$.

Example 117

Mouse Unilateral Ureteral Obstruction Kidney Fibrosis Model

Female C57BL/6 mice (Harlan, 20-25 g) housed 4/cage will be given free access to food and water and allowed to acclimate for at least 7 days prior to test initiation. After the habituation phase, mice undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. Mice are returned to their cages and monitored daily for the duration of the experiment. Test compound or vehicle is delivered p.o., i.p. or s.c. daily. The route and frequency of dosing is based on previously determined pharmacokinetic properties. All animals are sacrificed using inhaled isoflurane 4, 8 or 14 days after UUO surgery. Following sacrifice blood is drawn via cardiac puncture, the kidneys are harvested and one half of the kidney is frozen at −80° C. and the other half is fixed in 10% neutral buffered formalin for histological assessment of kidney fibrosis using light microscopy (10× magnification). Kidney tissue homogenates are analyzed for collagen levels using Sircol (Biocolor Ltd, UK). Fixed kidney tissue is also stained using hematoxylin and eosin (H&E) and trichrome and kidney fibrosis is determined by quantitative, computer-assisted densitometry of collagen in liver tissue sections using light microscopy and collagen content in kidney lysate. Plasma and kidney tissue lysates are also analyzed for concentrations of inflammatory, pro-fibrotic and tissue injury biomarkers including transforming growth factor β1, hyaluronic acid, tissue inhibitor of metalloproteinase-1, and plasminogen activator inhibitor-1, using commercially available ELISA. The resulting data are plotted using GraphPad Prism and statistical differences between groups determined.

Example 118

Clinical Trial in Humans with Idiopathic Pulmonary Fibrosis (IPF)

Purpose

The purposes of this study is to assess the efficacy of treatment with a compound of Formula (I) compared with placebo in patients with idiopathic pulmonary fibrosis (IPF) and to assess the safety of treatment with a compound of Formula (I) compared with placebo in patients with IPF.

The primary outcome variable is the absolute change in percent predicted forced vital capacity (FVC) from baseline to Week 72.

Secondary outcome measures include: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6MWT) from baseline to Week 72; change in high-resolution computed tomography (HRCT) assessment from baseline to Week 72; change in distance walked in the 6MWT from baseline to Week 72.

Criteria

Patients eligible for this study include those patients that satisfy the following inclusion criteria: diagnosis of IPF; 40 to 80 years of age; FVC≥50% predicted value; DLco≥35% predicted value; either FVC or DLco≤90% predicted value; no improvement in past year; able to walk 150 meters in 6 minutes and maintain saturation ≥83% while on no more than 6 L/min supplemental oxygen.

Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials.

Patients are orally dosed with either placebo or an amount of compound of Formula (I) (1 mg/day-1000 mg/day). The primary outcome variable will be the absolute change in percent predicted FVC from Baseline to Week 72. Patients will receive blinded study treatment from the time of randomization until the last patient randomized has been treated for 72 weeks. A Data Monitoring Committee (DMC) will periodically review safety and efficacy data to ensure patient safety.

After week 72, patients who meet the Progression of Disease (POD) definition, which is a ≥10% absolute decrease in percent predicted FVC or a ≥15% absolute decrease in percent predicted DLco, will be eligible to receive permitted IPF therapies in addition to their blinded study drug. Permitted IPF therapies include corticosteroids, azathioprine, cyclophosphamide and N-acetyl-cysteine.

Example 119

Parenteral Pharmaceutical Composition

To prepare a parenteral pharmaceutical composition suitable for administration by injection (subcutaneous, intravenous, and the like), 100 mg of a water-soluble salt of a compound of Formula (I) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formulas (I), 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 120

Oral Pharmaceutical Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example 121

Sublingual (Hard Lozenge) Pharmaceutical Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 122

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 m), and 2% by weight of magnesium stearate. Tablets are prepared by direct compression (*AAPS PharmSciTech*, 7(2):E41 (2006)). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (Inversina, Bioengineering AG, Switzerland) for 4.5 minutes. All of the magnesium stearate (MS) and the remaining one-third of the quantity of L-HPC are added 30 seconds before the end of mixing.

Example 123

Inhalation Pharmaceutical Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 124

Rectal Gel Pharmaceutical Composition

To prepare a pharmaceutical composition for rectal delivery, 100 mg of a compound of Formula (I) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 125

Topical Gel Pharmaceutical Composition

To prepare a pharmaceutical topical gel composition, 100 mg of a compound of Formula (I) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 126

Ophthalmic Solution

To prepare a pharmaceutical ophthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 127

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100l of spray for each application.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), or a pharmaceutically acceptable salt thereof:

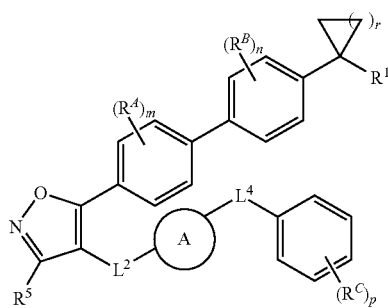

Formula (I)

wherein,
$R^1$ is —$CO_2R^D$, —C(=O)NHSO$_2R^E$, —C(=O)N($R^D$)$_2$, —CN, or tetrazolyl;
$R^D$ is H or $C_1$-$C_6$ alkyl;
$R^E$ is $C_1$-$C_6$ alkyl or phenyl;
$L^2$ is absent, —C(=O)—, —N($R^D$)—, substituted or unsubstituted $C_1$-$C_4$ alkylene, or substituted or unsubstituted $C_1$-$C_4$heteroalkylene, where if $L^2$ is substituted, then $L^2$ is substituted with $R^{12}$, where $R^{12}$ is F, $C_1$-$C_4$alkyl, —OH, or —$OR^D$;
ring A is a substituted or unsubstituted phenyl, a substituted or unsubstituted furanyl, a substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, or substituted or unsubstituted pyridazinyl, where if ring A is substituted, then ring A is substituted with 1 or 2 $R^{14}$, each $R^{14}$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
$L^4$ is absent, or a substituted or unsubstituted $C_1$-$C_4$ alkylene, where if $L^4$ is substituted then $L^4$ is substituted with $R^{13}$, where $R^{13}$ is F, $C_1$-$C_4$alkyl, —OH, or —$OR^D$;
$R^5$ is H or $C_1$-$C_4$alkyl;
each $R^A$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each $R^B$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
each $R^C$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
m is 0, 1 or 2;
n is 0, 1 or 2;
p is 0, 1 or 2;
r is 1, 2, 3, or 4.

2. The compound of claim 1, or a pharmaceutically acceptable salt thereof, wherein:
$R^1$ is —$CO_2R^D$, or —C(=O)NHSO$_2R^E$;
$L^2$ is absent, —C(=O)—, —NH—, —N(CH$_3$)—, —CH$_2$—, —CH$_2$CH$_2$—, —CH(CH$_3$)—, —CH$_2$CH(CH$_3$)—, —CH(CH$_3$)CH$_2$—, —CH(OH)—, —CH(OR$^D$)—, —CH$_2$CH(OH)—, —CH$_2$CH(OR$^D$)—, —CH(OH)CH$_2$—, —CH(OR$^D$)CH$_2$—, —CH$_2$NH—, —CH(CH$_3$)NH—, —NHCH$_2$— or —NHCH(CH$_3$)—;
$L^4$ is absent, —CH$_2$—, —CH(CH$_3$)—, —CH(OH)—, —CH$_2$CH$_2$—, —CH$_2$CH(CH$_3$)—, —CH(CH$_3$)CH$_2$—, —CH$_2$CH(OH)—, or —CH(OH)CH$_2$—;
$R^5$ is —H, —CH$_3$ or —CH$_2$CH$_3$;
m is 0 or 1;
n is 0 or 1;
r is 1, 2, or 3.

3. The compound of claim 2, or a pharmaceutically acceptable salt thereof, wherein:
$L^2$ is —NH—, —CH$_2$—, —CH$_2$CH$_2$—, —CH(CH$_3$)—, —CH$_2$CH(CH$_3$)—, —CH(CH$_3$)CH$_2$—, —CH(OH)—, —CH$_2$CH(OH)—, —CH(OH)CH$_2$—, —CH$_2$NH—, —CH(CH$_3$)NH—, —NHCH$_2$— or —NHCH(CH$_3$)—;
$L^4$ is absent, —CH$_2$—, or —CH(CH$_3$)—;
$R^5$ is —CH$_3$;
r is 1.

4. The compound of claim 3, or a pharmaceutically acceptable salt thereof, wherein:
ring A is a substituted or unsubstituted phenyl, where if ring A is substituted, then ring A is substituted with 1 or 2 $R^{14}$.

5. The compound of claim 1 or a pharmaceutically acceptable salt thereof, wherein:
ring A is

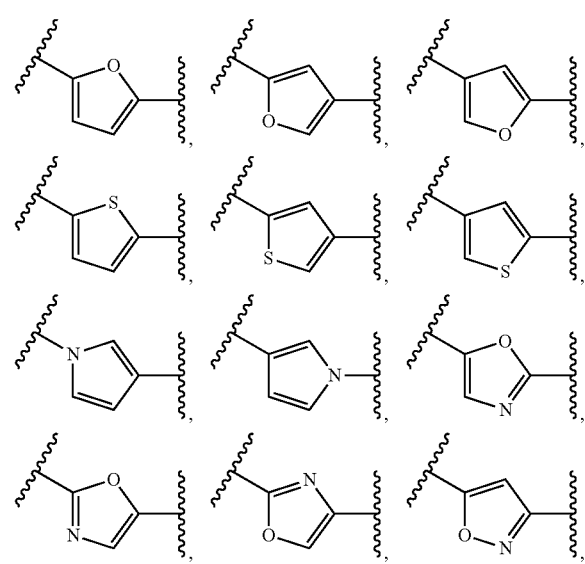

-continued
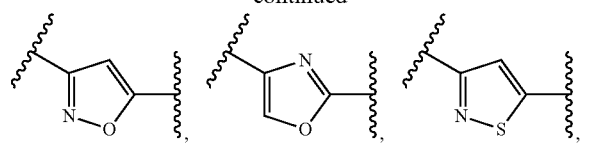
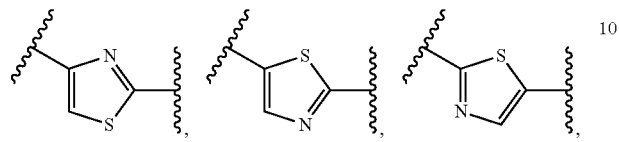
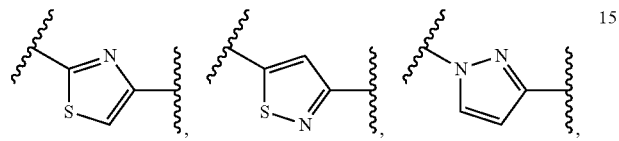
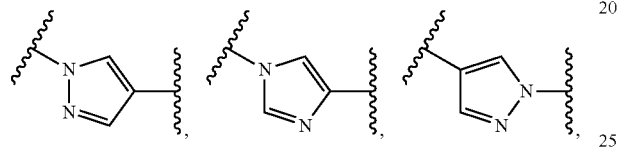
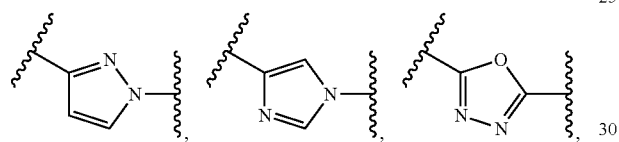
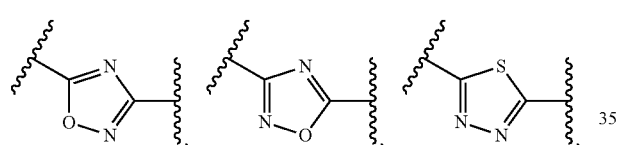
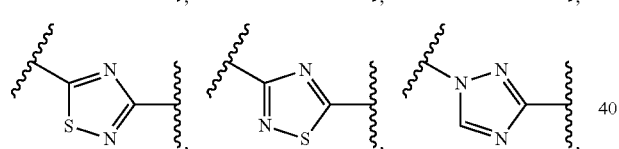
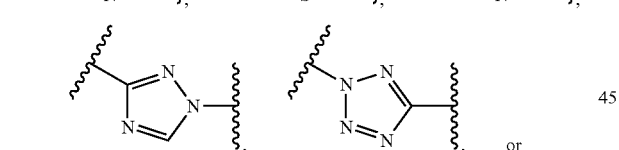
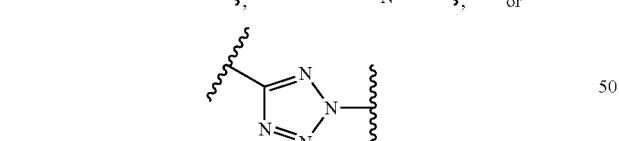
, or
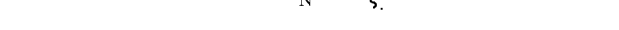
6. The compound of claim 1 or a pharmaceutically acceptable salt thereof, wherein:
ring A is
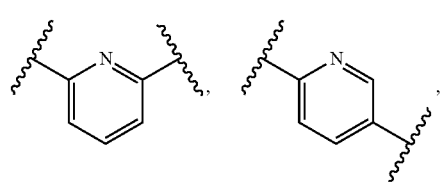
-continued
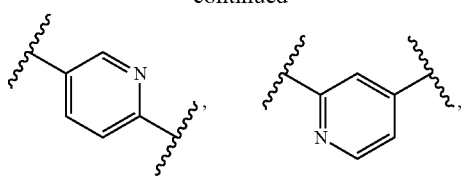
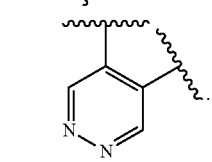
7. The compound of claim 1, or a pharmaceutically acceptable salt thereof, wherein the compound of Formula (I) has the structure of Formula (II):

Formula (II)

[chemical structure]

8. The compound of claim 7, or a pharmaceutically acceptable salt thereof, wherein:
$R^1$ is —CO$_2$R$^D$, or —C(=O)NHSO$_2$R$^E$;
$R^D$ is H or C$_1$-C$_4$ alkyl;
$R^E$ is C$_1$-C$_4$ alkyl;
$L^2$ is —CH$_2$—, —CH(CH$_3$)—, or —CH(OH)—;
ring A is a substituted or unsubstituted furanyl, substituted or unsubstituted pyrrolyl, substituted or unsubstituted oxazolyl, substituted or unsubstituted imidazolyl, substituted or unsubstituted pyrazolyl, substituted or unsubstituted tetrazolyl, substituted or unsubstituted isoxazolyl, substituted or unsubstituted oxadiazolyl, substituted or unsubstituted pyridinyl, substituted or unsubstituted pyrimidinyl, substituted or unsubstituted pyrazinyl, or substituted or unsubstituted pyridazinyl, where if ring A is substituted, then ring A is substituted with R$^{14}$;
$L^4$ is —CH$_2$— or —CH(CH$_3$)—;
p is 0 or 1.

9. The compound of claim 7, or a pharmaceutically acceptable salt thereof, wherein:
$R^1$ is —CO$_2$R$^D$, or —C(=O)NHSO$_2$R$^E$;
$R^D$ is H or C$_1$-C$_4$alkyl;
$R^E$ is C$_1$-C$_4$alkyl;
$L^2$ is —NH—, —CH$_2$—, —CH(CH$_3$)—, —CH(OH)—, —NHCH$_2$— or —NHCH(CH$_3$)—;
ring A is a substituted or unsubstituted pyridinylene, where if ring A is substituted, then ring A is substituted with R$^{14}$;
$L^4$ is absent, —CH$_2$—, or —CH(CH$_3$)—;
p is 0 or 1.

10. The compound of claim 1, wherein the compound is:
1-{4'-[3-Methyl-4-(3-phenyl-pyrazol-1-ylmethyl)-isoxazol-5-yl]-biphenyl-4-yl}-cyclopropanecarboxylic acid (Compound 1); 1-{4'-[3-Methyl-4-(5-phenyl-[1,3,4]oxadiazol-2-ylmethyl)-isoxazol-5-yl]-b-iphenyl-4-yl}-cyclopropanecarboxylic acid (Compound 3); 1-(4'-{4-[3-(4-Bromo-phenyl)-pyrazol-1-ylmethyl]-3-methyl-isoxazol-5-yl}-biphenyl-4-yl)-cyclopropanecarboxylic acid (Compound 5); 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid (Compound 6); 1-{4'-[3-Methyl-4-(5-phenyl-tetrazol-2-ylmethyl)-isoxazol-5-yl]-biphenyl-4-yl}-cyclopropanecarboxylic acid (Compound 8); 1-{4'-[3-Methyl-4-(4-phenyl-pyrazol-1-ylmethyl)-isoxazol-5-yl]-biphenyl-4-yl}-cyclopropanecarboxylic acid (Compound 9); 1-{4'-[4-(5-Benzyl-[1,3,4]oxadiazol-2-yl)-3-methyl-isoxazol-5-yl]-bipheny-1-4-yl}-cyclopropanecarboxylic acid (Compound 10); 1-{4'-[4-(5-Benzyl-[1,3,4]oxadiazol-2-ylmethyl)-3-methyl-isoxazol-5-yl]-biphenyl-4-yl}-cyclopropanecarboxylic acid (Compound 12); 1-(4'-{4-[(5-Benzyl-[1,3,4]oxadiazol-2-yl)-hydroxy-methyl]-3-methyl-isoxa-zol-5-yl}-biphenyl-4-yl)-cyclopropanecarboxylic acid (Compound 13); 1-(4'-{4-[(S)-(5-Benzyl-[1,3,4]oxadiazol-2-yl)-hydroxy-methyl]-3-methyl-i-soxazol-5-yl}-biphenyl-4-yl)-cyclopropanecarboxylic acid (Compound 15); 1-(4'-{4-[(R)-(5-Benzyl-[1,3,4]oxadiazol-2-yl)-hydroxy-methyl]-3-methyl-isoxazol-5-yl}-biphenyl-4-yl)-cyclopropanecarboxylic acid (Compound 16); 1-(4'-{4-[Hydroxy-(5-phenyl-[1,3,4]oxadiazol-2-yl)-methyl]-3-methyl-isoxa-zol-5-yl}-biphenyl-4-yl)-cyclopropanecarboxylic acid (Compound 17); 1-[4'-(4-{Hydroxy-[5-(3-trifluoromethyl-benzyl)-[1,3,4]oxadiazol-2-yl]-me-thyl}-3-methyl-isoxazol-5-yl)-biphenyl-4-yl]-cyclopropanecarboxylic acid (Compound 20); 1-{4'-[4-(Biphenyl-3-yl-hydroxy-methyl)-3-methyl-isoxazol-5-yl]-biphenyl-4-yl}-cyclopropanecarboxylic acid (Compound 22); 1-(4'-{4-[(3-Benzyl-phenyl)-hydroxy-methyl]-3-methyl-isoxazol-5-yl}-biphe-nyl-4-yl)-cyclopropanecarboxylic acid (Compound 26); 1-(4'-{4-[(5-Benzyl-pyridin-3-yl)-hydroxy-methyl]-3-methyl-isoxazol-5-yl}-biphenyl-4-yl)-cyclopropanecarboxylic acid (Compound 27); 1-{4'-[3-Methyl-4-(6-phenyl-pyridin-2-ylamino)-isoxazol-5-yl]-biphenyl-4- yl}-cyclopropanecarboxylic acid (Compound 33); 1-(4'-{4-[(6-Benzyl-pyridin-2-yl)-hydroxy-methyl]-3-methyl-isoxazol-5-yl}-biphenyl-4-yl)-cyclopropanecarboxylic acid (Compound 34); 1-{4'-[4-(6-Benzyl-pyridin-2-ylamino)-3-methyl-isoxazol-5-yl]-biphenyl-4- yl}-cyclopropanecarboxylic acid (Compound 38); 1-{4'-[4-(Biphenyl-3-ylamino)-3-methyl-isoxazol-5-yl]-biphenyl-4-yl}-cycl-opropanecarboxylic acid (Compound 39); 1-{4'-[4-(Biphenyl-4-ylamino)-3-methyl-isoxazol-5-yl]-biphenyl-4-yl}-cyclopropanecarboxylic acid (Compound 40); 1-(4'-{3-Methyl-4-[6-(3-trifluoromethyl-phenyl)-pyridin-2-ylamino]-isoxaz-ol-5-yl}-biphenyl-4-yl)-cyclopropanecarboxylic acid (Compound 41); 1-{4'-[3-Methyl-4-(6-phenyl-pyrazin-2-ylamino)-isoxazol-5-yl]-biphenyl-4- yl}-cyclopropanecarboxylic acid (Compound 42); 1-{4'-[3-Methyl-4-(5-phenyl-[1,3,4]oxadiazol-2-ylamino)-isoxazol-5-yl]-bi-phenyl-4-yl}-cyclopropanecarboxylic acid (Compound 43); 1-{4'-[4-(5-Benzyl-[1,3,4]oxadiazol-2-ylamino)-3-methyl-isoxazol-5-yl]-bi-phenyl-4-yl}-cyclopropanecarboxylic acid (Compound 44); 1-(4'-{4-[6-(2-Fluoro-benzyl)-pyridin-2-ylamino]-3-methyl-isoxazol-5-yl}-biphenyl-4-yl)-cyclopropanecarboxylic acid (Compound 45); 1-(4'-{4-[6-(3-Fluoro-benzyl)-pyridin-2-ylamino]-3-methyl-isoxazol-5-yl}-biphenyl-4-yl)-cyclopropanecarboxylic acid (Compound 46); 1-(4'-{4-[6-(4-Fluoro-benzyl)-pyridin-2-ylamino]-3-methyl-isoxazol-5-yl}-biphenyl-4-yl)-cyclopropanecarboxylic acid (Compound 47); 1-(4'-{4-[6-(3-Methoxy-phenyl)-pyridin-2-ylamino]-3-methyl-isoxazol-5-yl}-biphenyl-4-yl)-cyclopropanecarboxylic acid (Compound 48); 1-{4'-[4-(3-Benzyl-phenylamino)-3-methyl-isoxazol-5-yl]-biphenyl-4-yl}-cyclopropanecarboxylic acid (Compound 49); 1-(4'-{4-[6-(2-Cyano-phenyl)-pyridin-2-ylamino]-3-methyl-isoxazol-5-yl}-b-iphenyl-4-yl)-cyclopropanecarboxylic acid (Compound 50); 1-(4'-{4-[6-(4-Methoxy-phenyl)-pyridin-2-ylamino]-3-methyl-isoxazol-5-yl}-biphenyl-4-yl)-cyclopropanecarboxylic acid (Compound 51); 1-(4'-{4-[6-(3-Fluoro-phenyl)-pyridin-2-ylamino]-3-methyl-isoxazol-5-yl}-biphenyl- 4-yl)-cyclopropanecarboxylic acid (Compound 52); 1-(4'-{4-[6-(2-Methoxy-phenyl)-pyridin-2-ylamino]-3-methyl-isoxazol-5-yl}-biphenyl-4-yl)-cyclopropanecarboxylic acid (Compound 53); 1-(4'-{4-[6-(2-Fluoro-phenyl)-pyridin-2-ylamino]-3-methyl-isoxazol-5-yl}-biphenyl-4-yl)-cyclopropanecarboxylic acid (Compound 54); 1-(4'-{3-Methyl-4-[6-(2-trifluoromethyl-phenyl)-pyridin-2-ylamino]-isoxaz-ol-5-yl}-biphenyl-4-yl)-cyclopropanecarboxylic acid (Compound 55); 1-(4'-{3-Methyl-4-[(2-phenyl-thiazol-5-ylmethyl)-amino]-isoxazol-5-yl}-bi-phenyl-4-yl)-cyclopropanecarboxylic acid (Compound 56); 1-{4'-[3-Methyl-4-(2'-trifluoromethyl-biphenyl-3-ylamino)-isoxazol-5-yl]-biphenyl-4-yl}-cyclopropanecarboxylic acid (Compound 57); 1-{4'-[3-Methyl-4-(5-phenyl-pyridin-3-ylamino)-isoxazol-5-yl]-biphenyl-4-yl}-cyclopropanecarboxylic acid (Compound 58); 1-(4'-{4-[5-(3-Fluoro-phenyl)-pyridin-3-ylamino]-3-methyl-isoxazol-5-yl}-biphenyl-4-yl)-cyclopropanecarboxylic acid (Compound 59); 1-(4'-{4-[6-(2-Chloro-phenyl)-pyridin-2-ylamino]-3-methyl-isoxazol-5-yl}-biphenyl-4-yl)-cyclopropanecarboxylic acid (Compound 60); 1-(4'-{4-[Hydroxy-(6-phenyl-pyridin-2-yl)-methyl]-3-methyl-isoxazol-5-yl}-biphenyl-4-yl)-cyclopropanecarboxylic acid (Compound 61); 1-{4'-[3-Methyl-4-(2-phenyl-pyridin-4-ylamino)-isoxazol-5-yl]-biphenyl-4-yl}-cyclopropanecarboxylic acid (Compound 62); 1-(4'-{4-[2-(3-Fluoro-phenyl)-pyridin-4-ylamino]-3-methyl-isoxazol-5-yl}-biphenyl-4-yl)-cyclopropanecarboxylic acid (Compound 63); 1-(4'-{4-[5-(2-Chloro-phenyl)-pyridin-3-ylamino]-3-methyl-isoxazol-5-yl}-biphenyl-4-yl)-cyclopropanecarboxylic acid (Compound 64); 1-(4'-{4-[2-(2-Chloro-phenyl)-pyridin-4-ylamino]-3-methyl-isoxazol-5-yl}-biphenyl-4-yl)-cyclopropanecarboxylic acid (Compound 65); 1-{4'-[3-Methyl-4-(4-phenyl-pyrimidin-2-ylamino)-isoxazol-5-yl]-biphenyl-4-yl}-cyclopropanecarboxylic acid (Compound 66); 1-{4'-[3-Methyl-4-(4-phenyl-pyridin-2-ylamino)-isoxazol-5-yl]-biphenyl-4-yl}-cyclopropanecarboxylic acid (Compound 67); 1-(4'-{3-Methyl-4-[5-(3-trifluoromethyl-phenyl)-pyridin-3-ylamino]-isoxaz-ol-5-yl}-biphenyl-4-yl)-cyclopropanecarboxylic acid (Compound 68); 1-(4'-{3-Methyl-4-[5-(4-trifluoromethyl-phenyl)-pyridin-3-ylamino]-isoxazol-5-yl}-biphenyl-4-yl)-cyclopropanecarboxylic acid (Compound 69); 1-{4'-[3-Methyl-4-(6-phenyl-pyridin-2-ylamino)-isoxazol-5-yl]-biphenyl-4-yl}-cyclobutanecarboxylic acid (Compound 70); 1-(4'-{4-[Hydroxy-(5-phenyl-pyridin-3-yl)-methyl]-3-methyl-isoxazol-5-yl}-biphenyl-4-yl)-cyclopropanecarboxylic acid (Compound 71); 1-[4'-(4-{Hydroxy-[5-(3-trifluoromethyl-phenyl)-pyridin-3-yl]-methyl}-3-m-ethyl-isoxazol-5-yl)-biphenyl-4-yl]-cyclopropanecarboxylic acid (Compound 72); 1-{4'-[3-Methyl-4-(6-phenylethynyl-pyridin-2-ylamino)-isoxazol-5-yl]-biphenyl-4-yl}-cyclopropanecarboxylic acid (Compound 73); 1-(4'-{4-[6-(3-Cyano-phenyl)-pyridin-2-ylamino]-3-methyl-isoxazol-5-yl}-biphenyl-4-yl)-cyclopropanecarboxylic acid (Compound 74); 1-(4'-{4-[6-(5-Fluoro-2-methoxy-phenyl)-pyridin-2-ylamino]-3-methyl-isoxa-zol-5-yl}-biphenyl-4-yl)-cyclopropanecarboxylic acid (Compound 75); 1-(4'-{4-[6-(3-Chloro-5-fluoro-phenyl)-pyridin-2-ylamino]-3-methyl-isoxaz-ol-5-yl}-biphenyl-4-yl)-cyclopropanecarboxylic acid (Compound 76); 1-(4'-{4-[6-(2,5-Difluoro-phenyl)-pyridin-2-ylamino]-3-methyl-isoxazol-5-yl}-biphenyl-4-yl)-cyclopropanecarboxylic acid (Compound 77); 1-(4'-{4-[6-(2,6-Dichloro-phenyl)-pyridin-2-ylamino]-3-methyl-isoxazol-5-yl}-biphenyl-4-yl)-cyclopropanecarboxylic acid (Compound 78); 1-(4'-{4-[6-(2-Chloro-5-fluoro-phenyl)-pyridin-2-ylamino]-3-methyl-isoxaz-ol-5-yl}-biphenyl-4-yl)-cyclopropanecarboxylic acid (Compound 79); 1-(4'-{4-[6-(2,3-Difluoro-phenyl)-pyridin-2-ylamino]-3-methyl-isoxazol-5-yl}-biphenyl-4-yl)-cyclopropanecarboxylic acid (Compound 80); 1-(4'-{4-[6-(2-Chloro-3-fluoro-phenyl)-pyridin-2-ylamino]-3-methyl-isoxaz-ol-5-yl}-biphenyl-4-yl)-cyclopropanecarboxylic acid (Compound 81); 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid (Compound 82); 1-(4'-{4-[6-(3-Fluoro-2-methyl-phenyl)-pyridin-2-ylamino]-3-methyl-isoxaz-ol-5-yl}-biphenyl-4-yl)-cyclopropanecarboxylic acid (Compound 83); 1-(4'-{4-[6-(2-Chloro-3-trifluoromethyl-phenyl)-pyridin-2-ylamino]-3-meth-yl-isoxazol-5-yl}-biphenyl-4-yl)-cyclopropanecarboxylic acid (Compound 84); 1-{4'-[4-(2'-Dimethylaminomethyl-biphenyl-3-ylamino)-3-methyl-isoxaz-ol-5-yl]-biphenyl-4-yl}-cyclopropanecarboxylic acid (Compound 85); 1-(4'-{4-[6-(2,3-Dichloro-phenyl)-pyridin-2-ylamino]-3-methyl-isoxazol-5-yl}-biphenyl-4-yl)-cyclopropanecarboxylic acid (Compound 86); 1-(4'-{4-[6-(3-Fluoro-2-methoxy-phenyl)-pyridin-2-ylamino]-3-methyl-isoxa-zol-5-yl}-biphenyl-4-yl)-cyclopropanecarboxylic acid (Compound 87); 1-(4'-{4-[5-(3-Chloro-phenyl)-pyridin-3-ylamino]-3-methyl-isoxazol-5-yl}-biphenyl-4-yl)-cyclopropanecarboxylic acid (Compound 88); 1-(4'-{4-[5-(2,5-Difluoro-phenyl)-pyridin-3-ylamino]-3-methyl-isoxazol-5-yl}-biphenyl-4-yl)-cyclopropanecarboxylic acid (Compound 89); 1-(4'-{4-[6-(3-Chloro-phenyl)-pyridin-2-ylamino]-3-methyl-isoxazol-5-yl}-biphenyl-4-yl)-cyclopropanecarboxylic acid (Compound 90); N-[1-(4'-{4-[(5-Benzyl-[1,3,4]oxadiazol-2-yl)-hydroxy-methyl]-3-methyl-is-oxazol-5-yl}-biphenyl-4-yl)-cyclopropanecarbonyl]-methanesulfonamide (Enantiomer A) (Compound 92); N-(1-{4'-[3-Methyl-4-(5-phenyl-[1,3,4]oxadiazol-2-ylamino)-isoxazol-5-yl]-biphenyl-4-yl}-cyclopropanecarbonyl)-methanesulfonamide (Compound 94); N-(1-{4'-[4-(6-Benzyl-pyridin-2-ylamino)-3-methyl-isoxazol-5-yl]-biphenyl-4-yl}-cyclopropanecarbonyl)-methanesulfonamide (Compound 95); N-(1-{4'-[3-Methyl-4-(6-phenyl-pyridin-2-ylamino)-isoxazol-5-yl]-biphenyl-4-yl}-cyclopropanecarbonyl)-methanesulfonamide (Compound 96); 1-{4'-[3-Ethyl-4-(6-phenyl-pyridin-2-ylamino)-isoxazol-5-yl]-biphenyl-4-y-1}-cyclopropanecarboxylic acid (Compound 97); 1-{4'-[3-Ethyl-4-(5-phenyl-[1,3,4]oxadiazol-2-ylamino)-isoxazol-5-yl]-bip-henyl-4-yl}-cyclopropanecarboxylic acid (Compound 98); or a pharmaceutically acceptable salt thereof.

11. A pharmaceutical composition comprising a therapeutically effective amount of a compound of claim 1, or a pharmaceutically acceptable salt thereof.

12. The pharmaceutical composition of claim 11, wherein the pharmaceutical composition is formulated for intravenous injection, subcutaneous injection, oral administration, inhalation, nasal administration, topical administration, ophthalmic administration or otic administration.

13. The pharmaceutical composition of claim 11, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

\* \* \* \* \*